US012024716B2

(12) United States Patent
Good et al.

(10) Patent No.: US 12,024,716 B2
(45) Date of Patent: Jul. 2, 2024

(54) COMPOSITIONS AND METHODS OF EXPANSION OF T CELL POPULATIONS

(71) Applicant: THE BOARD OF TRUSTEES OF THE LELAND STANFORD JUNIOR UNIVERSITY, Stanford, CA (US)

(72) Inventors: Zinaida Good, Stanford, CA (US); Garry P. Nolan, Stanford, CA (US); Sean C. Bendall, Palo Alto, CA (US); Evan Weber, Stanford, CA (US); Crystal Mackall, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 605 days.

(21) Appl. No.: 16/960,504

(22) PCT Filed: Jan. 10, 2019

(86) PCT No.: PCT/US2019/013115
§ 371 (c)(1),
(2) Date: Jul. 7, 2020

(87) PCT Pub. No.: WO2019/140137
PCT Pub. Date: Jul. 18, 2019

(65) Prior Publication Data
US 2022/0186184 A1 Jun. 16, 2022

Related U.S. Application Data

(60) Provisional application No. 62/615,917, filed on Jan. 10, 2018.

(51) Int. Cl.
*C12N 5/0783* (2010.01)
*C07K 14/725* (2006.01)

(52) U.S. Cl.
CPC ........ *C12N 5/0636* (2013.01); *C07K 14/7051* (2013.01); *C12N 2503/02* (2013.01); *C12N 2510/00* (2013.01)

(58) Field of Classification Search
CPC .............. C12N 5/0636; C12N 2503/02; C12N 2510/00; C07K 14/7051
See application file for complete search history.

(56) References Cited

FOREIGN PATENT DOCUMENTS

| WO | 2014039044 A1 | 3/2014 |
|----|---------------|--------|
| WO | 2017189965 A1 | 11/2017 |

(Continued)

OTHER PUBLICATIONS

Fraietta, Joseph A., et al. "Ibrutinib enhances chimeric antigen receptor T-cell engraftment and efficacy in leukemia." Blood, The Journal of the American Society of Hematology 127.9 (2016): 1117-1127. (Year: 2016).*

(Continued)

*Primary Examiner* — Jeremy C Flinders
*Assistant Examiner* — Thomas R. Amick
(74) *Attorney, Agent, or Firm* — MINTZ, LEVIN, COHN, FERRIS, GLOVSKY AND POPEO, P.C.

(57) ABSTRACT

The present disclosure generally relates to compositions and methods useful for an adoptive cell therapy. Some embodiments of the disclosure relates to methods for producing a population of lymphocytes enriched in T stem cell memory cells ($T_{SCM}$ cells). Further provided are compositions containing a substantially pure population of $T_{SCM}$ cells that are therapeutically effective in treating various cancers, and kits containing such compositions. Methods for treating a subject having or suspected of having a cancer using the compositions and kits as disclosed herein are also provided.

19 Claims, 54 Drawing Sheets

(56) References Cited

FOREIGN PATENT DOCUMENTS

| WO | 2019014684 A1 | 1/2019 |
| WO | 2019140137 A1 | 7/2019 |

OTHER PUBLICATIONS

Long, M., Beckwith, K., Do, P., Mundy, B. L., Gordon, A., Lehman, A. M., . . . & Byrd, J. C. (2017). Ibrutinib treatment improves T cell number and function in CLL patients. The Journal of clinical investigation, 127(8), 3052-3064. (Year: 2017).*

Fraietta, J. A., Beckwith, K. A., Patel, P. R., Ruella, M., Zheng, Z., Barrett, D. M., . . . & Maus, M. V. (2016). Ibrutinib enhances chimeric antigen receptor T-cell engraftment and efficacy in leukemia. Blood, The Journal of the American Society of Hematology, 127(9), 1117-1127. (Year: 2016).*

Ruella, M., Kenderian, S. S., Shestova, O., Fraietta, J. A., Qayyum, S., Zhang, Q., . . . & Wasik, M. A. (2016). The Addition of the BTK Inhibitor Ibrutinib to Anti-CD19 Chimeric Antigen Receptor T Cells (CART19) Improves Responses agains . . . Clinical Cancer Research, 22(11), 2684-269 (Year: 2016).*

Gattinoni, L., Lugli, E., Ji, Y., Pos, Z., Paulos, C. M., Quigley, M. F., . . . & Restifo, N. P. (2011). A human memory T cell subset with stem cell-like properties. Nature medicine, 17(10), 1290-1297. (Year: 2011).*

Dubovsky, J. A., Beckwith, K. A., Natarajan, G., Woyach, J. A., Jaglowski, S., Zhong, Y., . . . & Byrd, J. C. (2013). Ibrutinib is an irreversible molecular inhibitor of ITK driving a Th1-selective pressure in T lymphocytes. Blood, The Journal of the American Society of Hematology, 122(15), 2539-2549. (Year: 2013).*

Sabatino, M., Hu, J., Sommariva, M., Gautam, S., Fellowes, V., Hocker, J. D., . . . & Gattinoni, L. (2016). Generation of clinical-grade CD19-specific CAR-modified CD8+ memory stem cells for the treatment . . . Blood, The Journal of the American Society of Hematology, 128(4), 519-528. (Year: 2016).*

Gust, T. C., Neubrandt, L., Merz, C., Asadullah, K., Zügel, U., & von Bonin, A. (2008). Correction: RNA interference-mediated gene silencing in murine T cells: in vitro and in vivo validation of proinflammatory target genes. Cell Communication and Signaling, 6(1), 1-8. (Year: 2008).*

Andreotti, A. H., Schwartzberg, P. L., Joseph, R. E., & Berg, L. J. (2010). T-cell signaling regulated by the Tec family kinase, Itk. Cold Spring Harbor perspectives in biology, 2(7), a002287. (Year: 2010).*

Marostica et al. (2015) Population Pharmacokinetic Model of Ibrutinib, a Bruton Tyrosine Kinase Inhibitor, in Patients with B Cell Malignancies, Cancer Chemother Pharmacol, 75(1):111-121.

Advani et al. (2013) "Bruton Tyrosine Kinase Inhibitor Ibrutinib (PCI-32765) has Significant Activity in Patients with Relapsed/Refractory B-cell Malignancies", Journal of Clinical Oncology, 31(1):88-94.

Angerer et al. (2016) "Destiny: Diffusion Maps for Large-scale Single-cell Data in R", Bioinformatics', 32(8): 1241-1243.

Apetoh et al. (Apr. 2015) "Consensus Nomenclature for Cds+ T Cell Phenotypes in Cancer", Oncoimmunology, 4(4):12 Pages.

Araki et al. (2009) "mTOR Regulates Memory CDS T-cell Differentiation.", Nature, 460(7251):108-112.

Bandura et al. (Aug. 2019) "Mass Cytometry: Technique for Real Time Single Cell Multitarget Immunoassay Based on Inductively Coupled Plasma Time-of-Flight Mass Spectrometry", Analytical Chemistry, 81(16):6813-6822.

Bandura et al. (May 2011) "Single-cell Mass Cytometry of Differential Immune and Drug Responses Across a Human Hematopoietic Continuum", Science, 332(6030):687-696.

Bates et al. (2015) "Fitting Linear Mixed-Effects Models Using lme4", Journal of Statistical Software, 67(1):1-48.

Battich et al. (Dec. 2015) "Control of Transcript Variability in Single Mammalian Cells", Cell, 163(7):1596-1610.

Begum et al. (2013) "A Method for Evaluating the Use of Fluorescent Dyes to Track Proliferation in Cell Lines by Dye Dilution", Cytometry Part A, 83(12):1085-1095.

Brenchet al. (Dec. 2002) "Expansion of Activated Human Naive T-838 Cells Precedes Effector Function", Clinical and Experimental Immunology, 130(3):432-440.

Chacon et al. (Apr. 2013) "Co-Stimulation through 4-1BB/CD137 Improves the Expansion and Function of CD8+ Melanoma Tumor-Infiltrating Lymphocytes for Adoptive T-Cell Therapy", PLoS One, 8(4):14 Pages.

Chang et al. (Mar. 2007) "Asymmetric T Lymphocyte Division in the Initiation of Adaptive Immune Responses", Science, 315(5819):1687-1691.

Cieri et al. (Jan. 24, 2003) "IL-7 and IL-15 Instruct the Generation of Human Memory Stem T cells from Naive Precursors", Blood, 121(4):573-584.

Coifman et al. (2005) "Geometric Diffusions as a Tool for Harmonic Analysis and Structure Definition of Data: Diffusion Maps", Proceedings of the National Academy of Sciences of the United States of America, 102(21):7426-7431.

Fienberg et al. (2012) "A Platinum Based Covalent Viability Reagent for Single-cell Mass Cytometry", Cytometry A., 81(6):467-475.

Finck R, Simonds EF, Jager A, Krishnaswamy S, Sachs K, Fantl W, Pe'er D, Nolan GP, Bendall SC. Normalization of mass cytometry data with bead standards. Cytometry A. May 2013;83(5) : 483-94.

Fleischer et al. (1996) "Differential expression and Function of CD80 (B7-1) and CD86 (B7-2) on Human Peripheral Blood Monocytes", Immunology, 89(4):592-598.

Forget et al. (2014) "Activation and Propagation of Tumor-infiltrating Lymphocytes on Clinical-grade Designer Artificial Antigen-presenting Cells for Adoptive Immunotherapy of Melanoma", Journal of immunotherapy, 3(9):448-460.

Good et al. (Feb. 11, 2019) "Proliferation Tracing with Single-Cell Mass Cytometry Optimizes Generation of Stem Cell Memory-like T Cells", Nature Biotechnology, 37(3):259-266(13 Pages).

Friedman et al. (2010) "Regularization Paths for Generalized Linear Models via Coordinate Descent.", Journal of Statistical Software, 33(1):1-22.

Gattinoni et al. (Jan. 2017) "T Memory Stem Cells in Health and Disease", Nature medicine, 23(1):18-27.

Geltink et al. (Oct. 2017) "Mitochondrial Priming by CD28", Cell, 171(2):385-397.

Gerlach et al. (May 2013) "Heterogeneous Differentiation Patterns of Individual CD8+ T Cells", Science, 340(6132):635-639.

Gerlach et al. (Jun. 2010) "One Naive T Cell, Multiple Fates in CD8+ T Cell Differentiation", Journal of Experimental Medicine, 207(6):1235-1246.

Gill et al. (May 2017) "CD19 CAR-T Cells Combined with Ibrutinib to Induce Complete Remission in CLL", Journal of Clinical Oncology, 35(15):7509-7509.

Heinzel et al. (Jan. 2017) "A Myc-Dependent Division Timer Complements a Cell-Death Timer to Regulate T Cell and B Cell Responses", Nature Immunology, 18(1):96-103.

Huang et al. (2015) "The Tyrosine Kinase Itk Suppresses CD8+ Memory T Cell Development in Response to Bacterial Infection", Scientific reports, 5(7688):8 Pages.

Jacomy et al. (2014) "ForceAtlas2, a Continuous Graph Layout Algorithm for Handy Network Visualization Designed for the Gephi Software", PLoS One, 9(6):12 Pages.

Ju et al. (2003) "A Functional anti-human 4-IBB Ligand Monoclonal Antibody that Enhances Proliferation of Monocytes by Reverse Signaling of 4-IBBL", Hybridoma hybridomics, 22(5):333-338.

Kalia et al. (2010) "Prolonged Interleukin-2Ralpha Expression on Virus-specific CDS+ T Cells Favors Terminal-Effector Differentiation in Vivo", Immunity, 32(1):91-103.

Kono, K. (2014) "Current Status of Cancer Immunotherapy", Journal of stem cells & regenerative medicine, 10(1): 8-13.

Li et al. (2010) "Comparison of anti-CD3 and anti-CD28-coated Beads with Soluble anti-CD3 for expanding human T cells: Differing Impact on CDS T Cell Phenotype and Responsiveness to Restimulation.", Journal of Translational Medicine, 8(104):15 Pages.

Lin et al. (2016) "CDS+ T Lymphocyte Self-Renewal during Effector Cell Determination", Cell reports, 17(7):1773-1782.

(56) References Cited

OTHER PUBLICATIONS

Zheng et al., "Massively Parallel Digital Transcriptional Profiling of Single Cells", Nature Communications, 2017, 8(14049):12 Pages.
Xu et al., "The Roles of Stem Cell Memory T Cells in Hematological Malignancies", Journal of Hematology & Oncology, Oct. 2015, 8(113):5 Pages.
Lyons et al. (May 1994) "Determination of Lymphocyte Division by Flow Cytometry", Journal of Immunological Methods, 171(1):131-137.
Mackall et al. (2014) "Immune-based Therapies for Childhood Cancer", Nature reviews Clinical oncology, 11(12):693-703.
Marchingo et al. (Nov. 2014) "T Cell Signaling. Antigen Affinity, Costimulation, and Cytokine Inputs Sum Linearly to Amplify T Cell Expansion", Science, 346(6213):1123-1127.
Mellman et al. (2011) "Cancer Immunotherapy Comes of Age", Nature, 480(7378):480-489.
Nestorowa et al. (2016) "A Single-cell Resolution Map of Mouse Hematopoietic Stem and Progenitor Cell Differentiation", Blood, 128(8):e20-e31(13 Pages).
Nish et al. (Jan. 2017) "CD4+ T Cell Effector Commitment Coupled to Self-renewal by Asymmetric Cell Divisions", The Journal of experimental medicine, 214(1):39-47.
Oliaro et al. (Jul. 2010) "Asymmetric Cell Division of T Cells Upon Antigen Presentation Utilizes Multiple Conserved Mechanisms", Journal of Immunology, 185(1):367-375.
Pipkin et al. (2010) "Interleukin-2 and Inflammation Induce Distinct Transcriptional Programs that Promote the Differentiation of Effector Cytolytic T Cells", Immunity, 32(1):79-90.
Quah et al. (Feb. 2012) "New and Improved Methods for Measuring Lymphocyte Proliferation in vitro and in vivo Using CFSE-like Fluorescent Dyes", Journal of Immunological Methods, 379(1-2):1-14.
Quah et al. (Oct. 2010) "The Use of Carboxyfluorescein Diacetate Succinimidyl Ester (CFSE) to Monitor Lymphocyte Proliferation", Journal of visualized experiments, 44:4 Pages.
Quah et al. (2012) "The Use of CFSE-like Dyes for Measuring Lymphocyte Proliferation: Experimental Considerations and Biological Variables", Mathematical Modelling of Natural Phenomena, 7(5):53-64.
Zunder et al. (2015) "A Continuous Molecular Roadmap to iPSC Reprogramming through Progression Analysis of Single-Cell Mass Cytometry", Cell Stem Cell, 16(3):323-337.
Rambold et al. (2018) "Mitochondrial Dynamics at the Interface of Immune Cell Metabolism and Function", Trends in immunology, 39(1):6-18.
Reiner et al. (2014) "Lymphocyte Fate Specification as a Deterministic but Highly Plastic Process", Nature Reviews Immunology, 14(10):699-704.
Rosenberg et al. (Apr. 2015) "Adoptive Cell Transfer as Personalized Immunotherapy for Human Cancer", Science, 348(6230):62-68.
Rosenberg et al. (2004) "Cancer Regression in Patients with Metastatic Melanoma after the Transfer of Autologous Antitumor Lymphocytes", Proceedings of the National Academy of Sciences of the United States of America, 101(Suppl 2):14639-14645.
Zunder et al. (2015) "Palladium-based Mass-Tag Cell Barcoding with a Doublet-Filtering Scheme and Single Cell Deconvolution Algorithm", Nature protocols, 10(2):316-333.
Salter et al. (2018) "Phosphoproteomic Analysis of Chimeric Antigen Receptor Signaling Reveals Kinetic and Quantitative Differences That Affect Cell Function", Science signaling, 11(544):35 Pages.
Samusik et al. (Jun. 2016) "Automated Mapping of Phenotype Space with Single-cell Data.", Nature methods, 13(6):493-496.
Stenton et al. (2005) "Sirolimus: The Evidence for Clinical Pharmacokinetic Monitoring", Clinical Pharmacokinetics, 44(8):769-786.
Tibshirani, Robert (1996) "Regression Shrinkage and Selection via the Lasso", Journal of the Royal Statistical Society, Series B, 58(1):267-288.
Tubo et al. (Jan. 2016) "Most Microbe-specific Naïve CD4+ T Cells Produce Memory Cells During Infection", Science, 351(6272):511-514.
Turtle et al. (2017) "Durable Molecular Remissions in Chronic Lymphocytic Leukemia Treated with CD19-Specific Chimeric Antigen Receptor-Modified T Cells After Failure off Ibrutinib", Journal of clinical oncology: official journal of the American Society of Clinical Oncology, 35(26):3010-3020.
Woodworth et al. (Jan. 2017) "Building a Lineage from Single Cells: Genetic Techniques for Cell Lineage Tracking", Nature Reviews Genetics, 18:230-244.
International Search Report and Written Opinion for PCT International Application No. PCT/US2019/013115, mailed on Apr. 5, 2019, 15 Pages.
International Preliminary Report on Patentability for PCT International Application No. PCT/US2019/013115, mailed on Jul. 23, 2020, 10 Pages.

\* cited by examiner

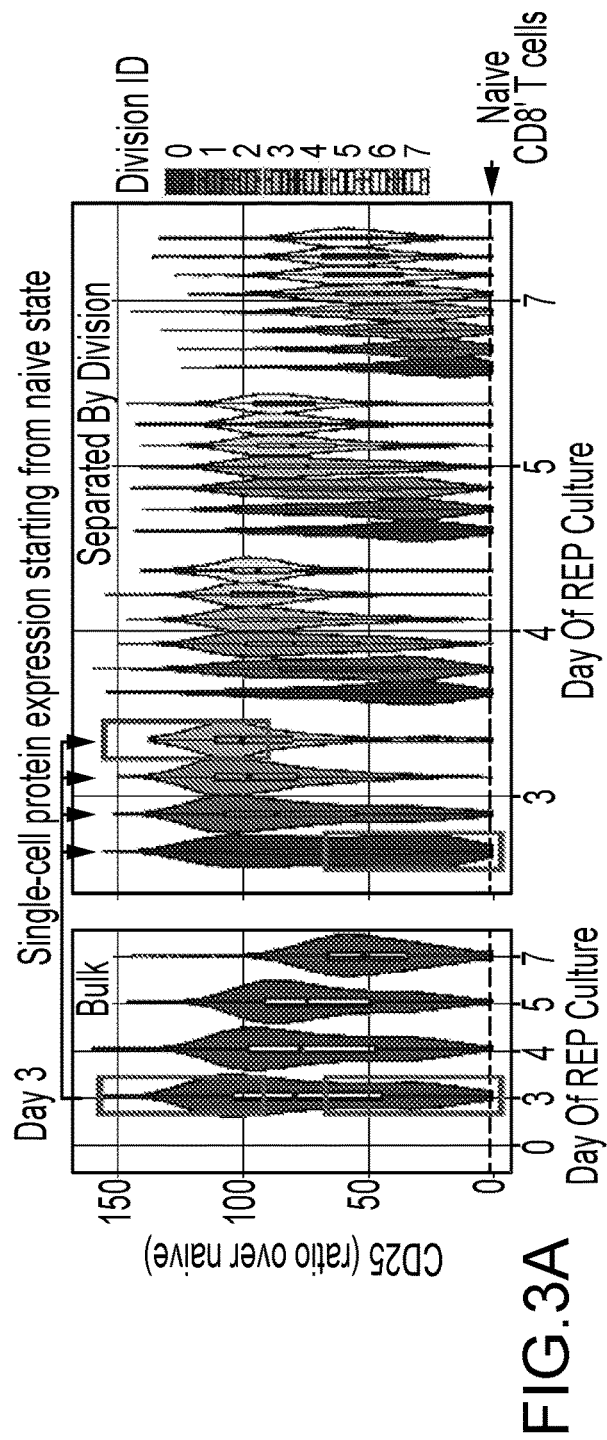
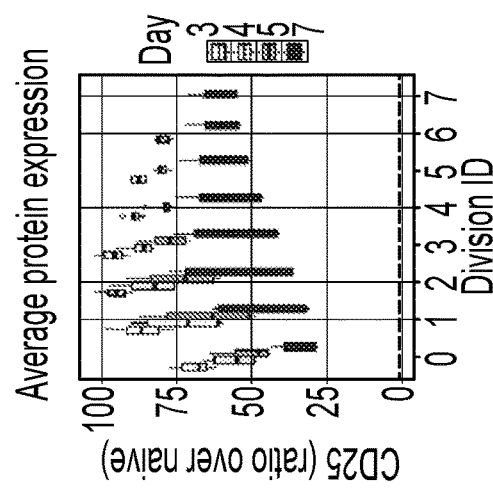
FIG. 3A
FIG. 3B

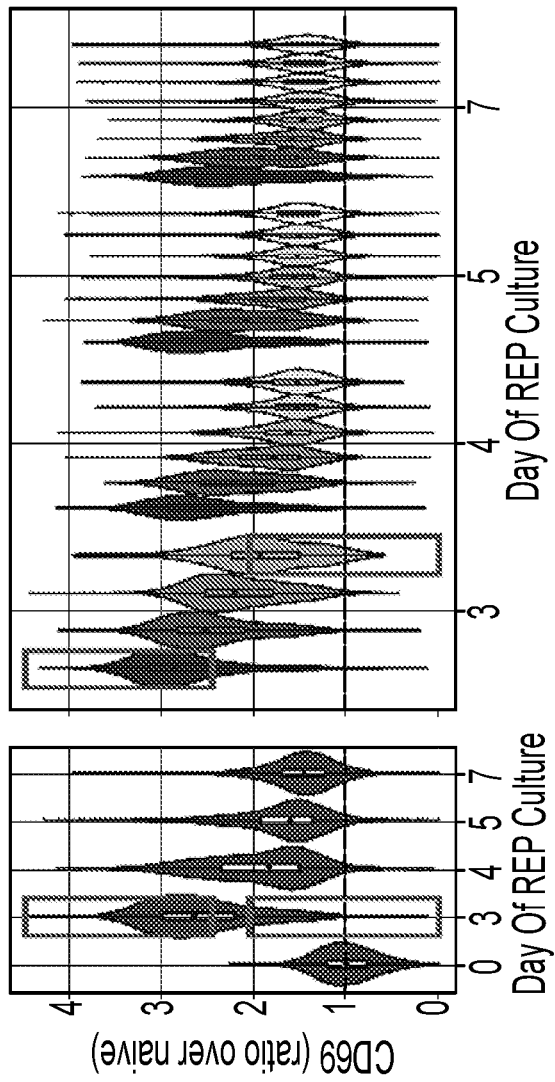
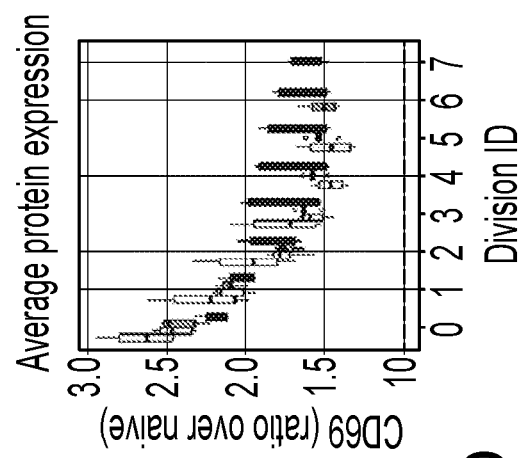
FIG. 3C
FIG. 3D

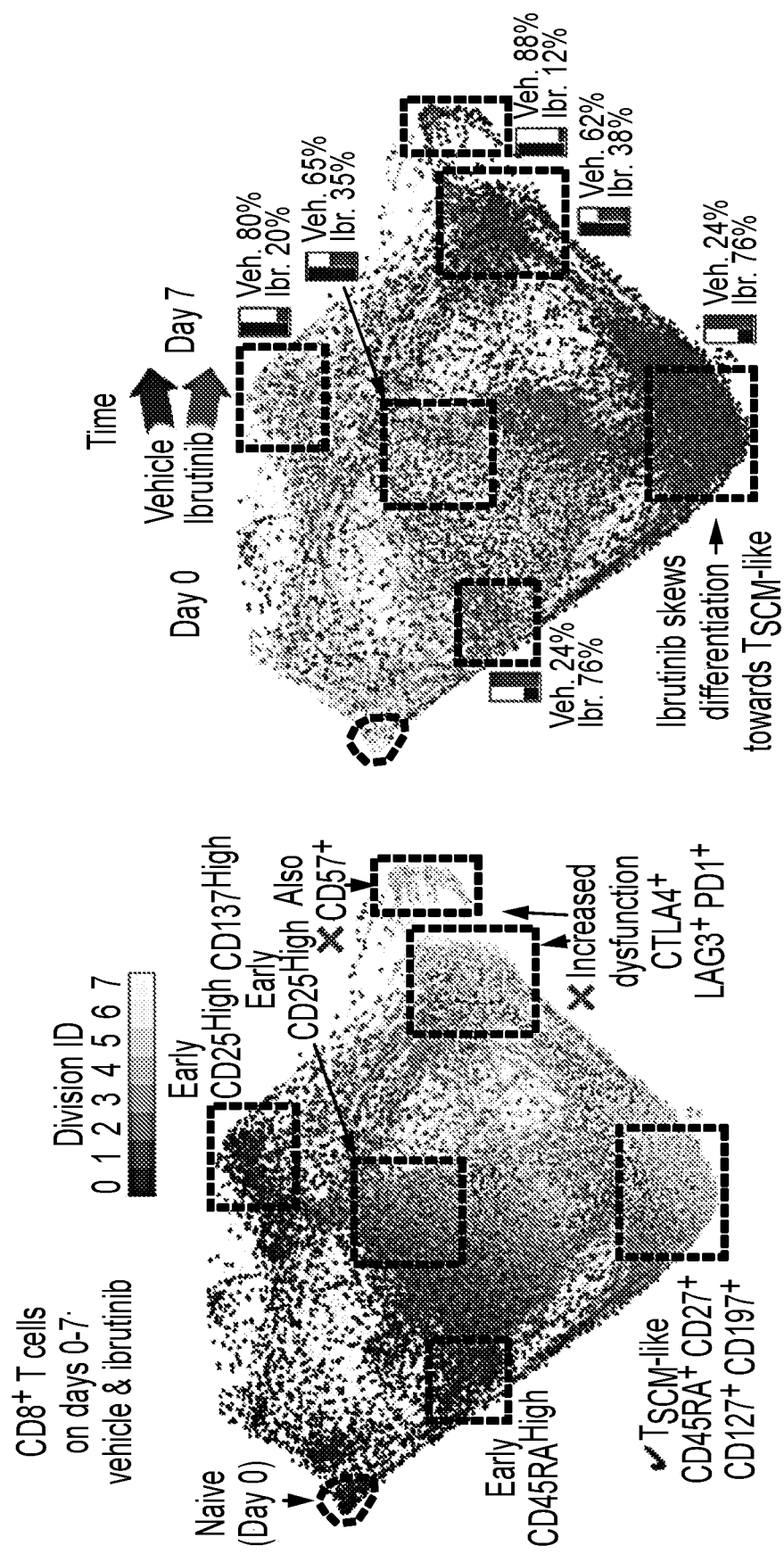

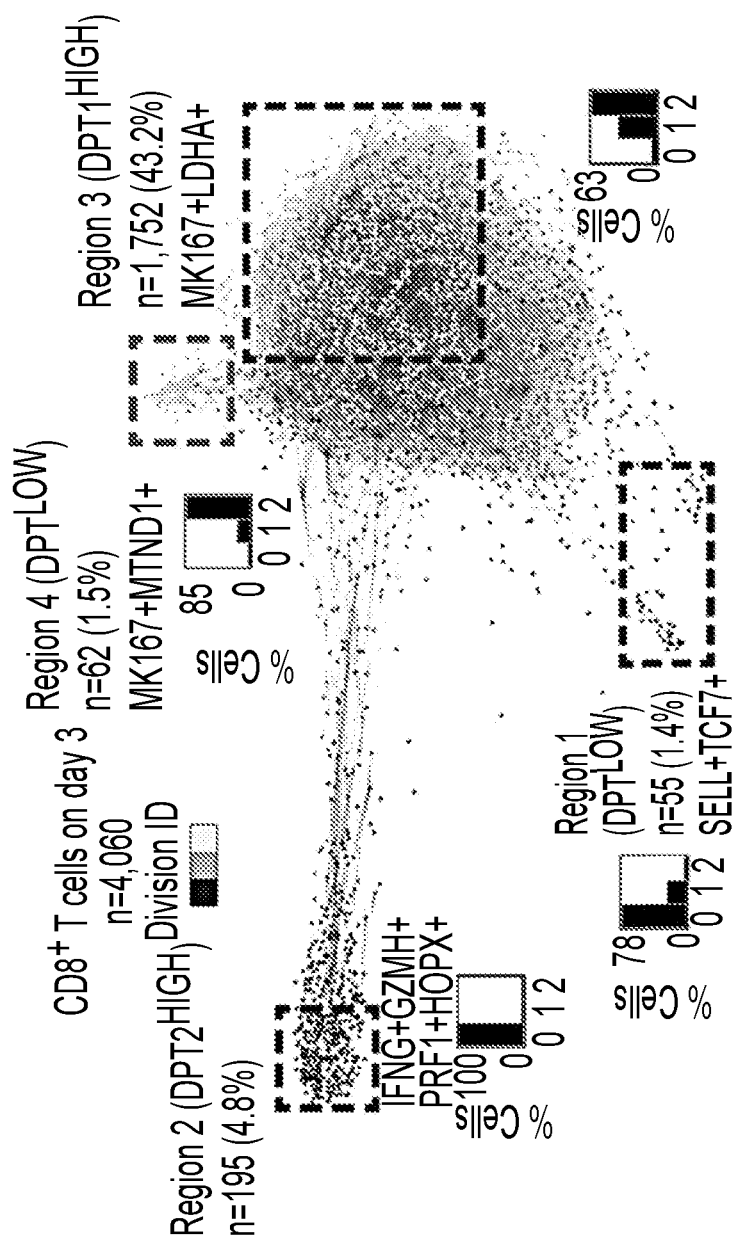

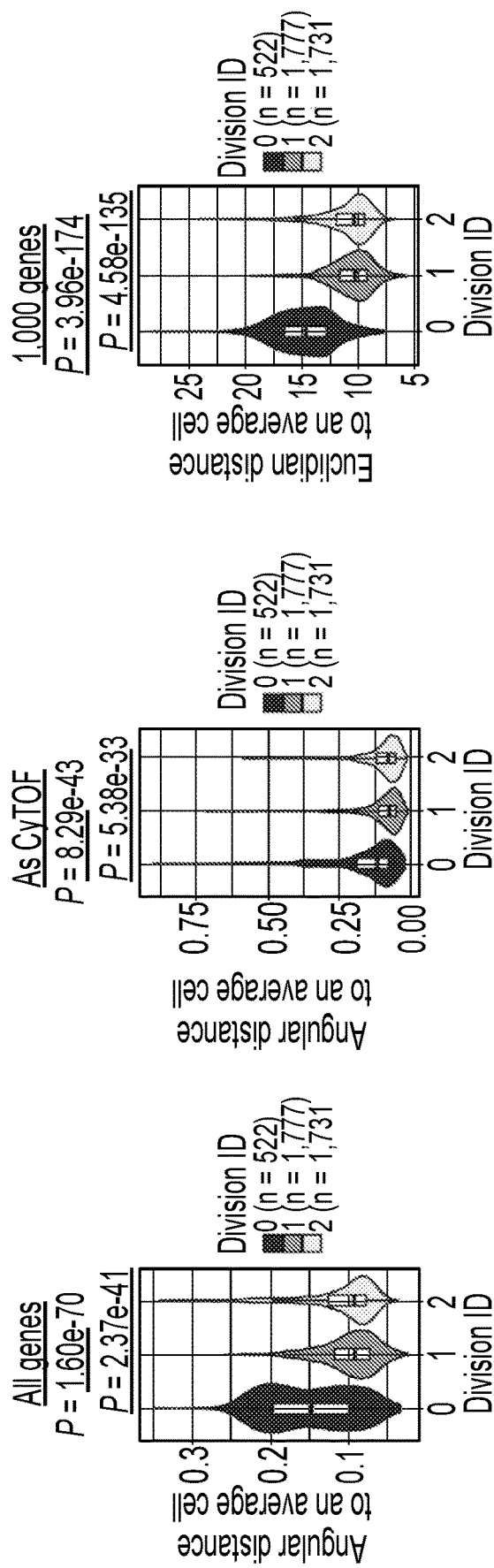

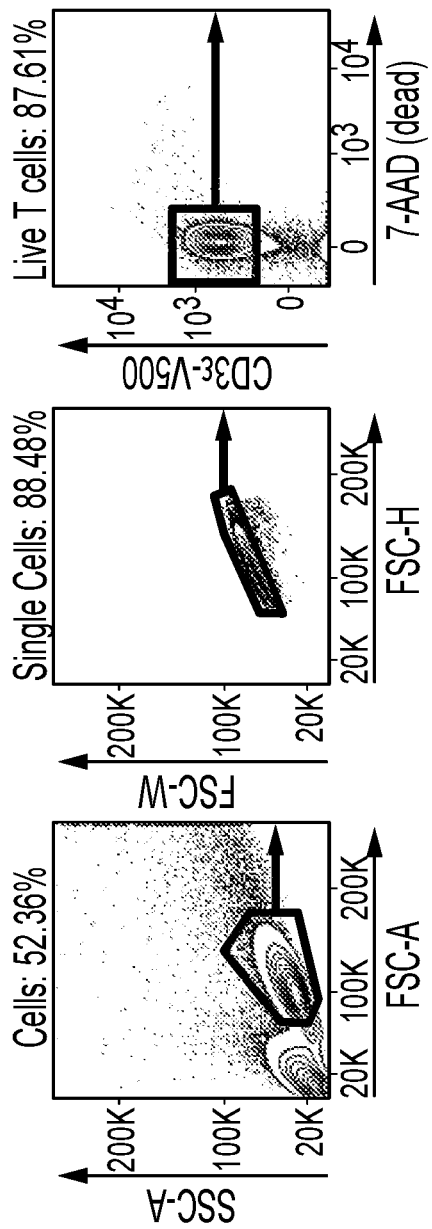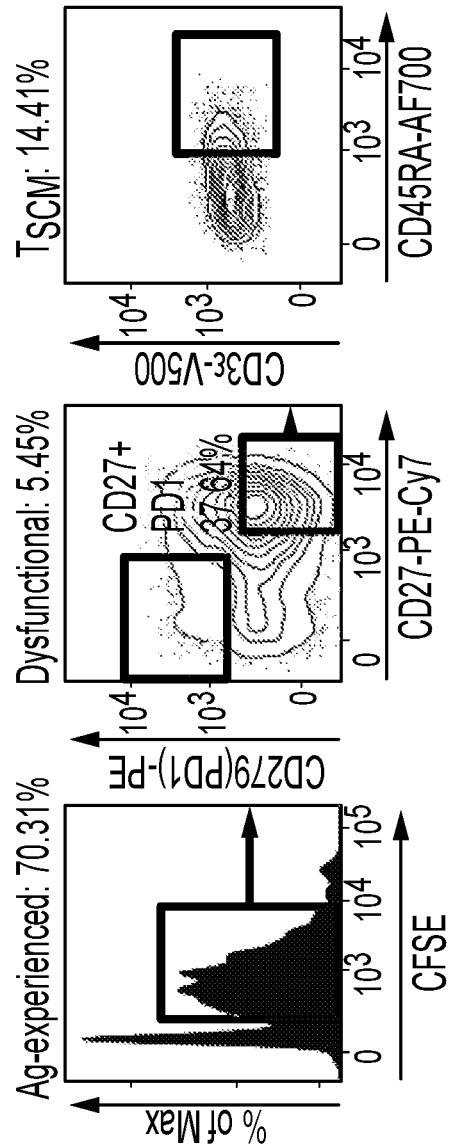
FIG. 11B

COMPOSITIONS AND METHODS OF EXPANSION OF T CELL POPULATIONS

CROSS-REFERENCE TO RELATED APPLICATIONS

The present application is a U.S. National Phase Application of PCT International Application No. PCT/US2019/013115, filed on Jan. 10, 2019, designating the United States of America, which is an International Application of and claims the benefit of priority to U.S. Provisional Patent Application Ser. No. 62/615,917, filed on Jan. 10, 2018. The disclosure of the above-referenced applications are herein expressly incorporated by reference in their entireties, including any drawings.

STATEMENT REGARDING FEDERALLY SPONSORED R&D

This invention was made with Government support under contracts AI007290, GM104148, CA149145, and EB024246 awarded by the National Institutes of Health. The Government has certain rights in the invention.

BACKGROUND

T stem cell memory ($T_{SCM}$) cells are memory lymphocytes endowed with the stem cell-like ability to self-renew and the multipotent capacity to reconstitute the entire spectrum of memory and effector T cell subsets. $T_{SCM}$ cells are generally considered as minimally differentiated cells at the apex of the hierarchical system of memory T lymphocytes. $T_{SCM}$ cell potency has been suggested as a way to enhance the efficacy of, for example, vaccines and adoptive T cell therapies for cancer and infectious diseases or, conversely, how it could be disrupted to treat $T_{SCM}$ cell driven and sustained diseases, such as autoimmunity, adult T cell leukemia and HIV-1. However, even though the proposed regimens are considered promising, there are still significant limitations that render these $T_{SCM}$-based approaches inadequate, which underscores the need for further improvements.

In particular, the likelihood of successful treatment is correlated, at least in part, with the level of $T_{SCM}$ cells in a pool of cells transplanted to a patient or engraftment. An effective amount of $T_{SCM}$ cells may be that is sufficient to build up memory and effector T cells effective to treat a target condition, e.g., cancer, and maintain their own pool in the system without being outcompeted by the patient's endogenous T cells. Therefore, provision of an amount of $T_{SCM}$ cells that is sufficient to sustain durable effect is important for successful treatment of the patient.

Currently, the source of $T_{SCM}$ cells used in therapeutic treatment is generally a donor, e.g., a patient or a non-patient donor. Importantly, $T_{SCM}$ cells constitute a very rare subset of T cells in humans and therefore, the level of $T_{SCM}$ cells present in a therapeutic composition for cell therapy is often below the desired effective amount or requires multiple rounds of harvest of $T_{SCM}$ cells. Also, once the primary T cells including $T_{SCM}$ cells that were isolated from a donor start being cultured in vitro, the properties of the cells become changed, therefore propagation of $T_{SCM}$ cells to a desired level is also difficult. Therefore, there is an urgent need to provide improved cell therapy compositions and use thereof for a successful treatment.

SUMMARY

The present disclosures provide, inter alia, methods and compositions for expansion of T cell populations. In particular, the methods and compositions provided herewith can expand the population of $T_{SCM}$ cells that is therapeutically effective in treating a variety of conditions including, for example, cancer.

In one aspect, provided herein are methods of producing a population of enriched T stem cell memory cells ($T_{SCM}$ cells), the method including contacting a sample containing naturally occurring T cells or engineered T cells with an agent that modulates the Bruton's tyrosine kinase (BTK) signaling pathway and/or the inducible T cell kinase (ITK) signaling pathway in an amount sufficient to produce a population of enriched $T_{SCM}$ cells. In some embodiments, the sample is a biological sample isolated from a subject.

In some embodiments, the biological sample comprises tumor-infiltrating lymphocytes. In some embodiments, the biological sample comprises peripheral blood mononuclear cells (PBMCs). In some embodiments, the biological sample comprises human naïve T cells. In some embodiments, the biological sample comprises human primary T cells. In some embodiments, the human naïve T cells or the human primary T cells are purified from the biological sample prior to the contacting with the agent. In some embodiments, the sample comprising engineered T cells having chimeric antigen receptors (CARs). In some embodiments, the sample comprising engineered T cells having recombinant T cell receptors (TCRs).

In some embodiments, the percentage of $T_{SCM}$ cells in the total T cells is increased by about 0.5-fold to about 200-fold after the contacting with the agent when compared to the percentage of $T_{SCM}$ cells in the total cells prior to the contacting. In some embodiments, the percentage of non-$T_{SCM}$ cells in the total T cells is decreased by about 0.5-fold to about 200-fold after the contacting with the agent when compared to the percentage of non-$T_{SCM}$ cells in the total T cells prior to the contacting.

In some embodiments, the non-$T_{SCM}$ cells comprise dysfunctional and/or senescent T cells. In some embodiments, the dysfunctional T cells comprise exhausted T cells.

In some embodiments, the biological sample is contacted with the agent prior to expansion of the T cell. In some embodiments, the biological sample is contacted with the agent less than about 24 hours after T cell expansion initiation. In some embodiments, the biological sample is contacted with the agent less than about 24 hours after the biological sample is isolated from the subject. In some embodiments, the biological sample is contacted with the agent less than about 48 hours after the biological sample is isolated from the subject. In some embodiments, the biological sample is contacted with the agent less than about 72 hours after the biological sample is isolated from the subject. In some embodiments, the biological sample is contacted with the agent prior to the first cell division of T cells contained in the biological sample after the biological sample is isolated from the subject. In some embodiments, the biological sample is isolated from the subject about 0 hours to about 24 hours before ibrutinib is administered to the subject.

In some embodiments, the biological sample is cryopreserved substantially immediately after being isolated from the subject. In some embodiments, the cryopreserved sample is thawed into a cell culture medium prior to the contacting with the agent. In some embodiments, the biological sample is thawed and contacted with the agent prior to expansion of the T cell. In some embodiments, the agent decreases the activity of the BTK signaling pathway. In some embodiments, the agent decreases the activity of the ITK signaling pathway. In some embodiments, the agent decreases the activity of both the BTK signaling pathway and the ITK signaling pathway. In some embodiments, the agent is PCI-32765 (ibrutinib). In some embodiments, the ibrutinib is provided at a concentration between about 10 ng/mL to about 10 µg/mL. In some embodiments, the ibrutinib is provided at a concentration between about 10 ng/mL to about 2 µg/mL In some embodiments, the agent is selected from the group consisting of PRN694 (5-(difluoromethyl)-N-[5-[[[(2S)-3,3-dimethylbutan-2-yl]amino]methyl]-1-[[(2R)-1-prop-2-enoylpyrrolidin-2-yl]methyl]benzimidazol-2-yl] thiophene-2-carboxamide), BMS 509744 (N-[5-[[5-[(4-Acetyl-1-piperazinyl)carbonyl]-4-methoxy-2-methylphenyl]thio]-2-thiazolyl]-4-[[(1,2,2-trimethylpropyl) amino]methyl]benzamide), CTA 056 (1,5-Dihydro-7-(phenylmethyl)-1-[3-(1-piperidinyl)propyl]-2-[4-(4-pyridinyl)phenyl]-6H-imidazo[4,5-g]quinoxalin-6-one), GSK 2250665A (trans-4-[[4-[(6-Ethyl-2-benzothiazolyl) amino]-6-(phenylmethyl)-2-pyrimidinyl]amino]cyclohexanol) and PF 06465469 ((R)-3-(1-(1-Acryloylpiperidin-3-yl)-4-amino-1H-pyrazolo[3,4-d]pyrimidin-3-yl)-N-(3-methyl-4-(1-methylethyl))benzamide).

In some embodiments, the agent comprises one or more nucleic acid sequences that decrease the activity of the BTK signaling pathway and/or the ITK signaling pathway via RNA interference (RNAi).

In some embodiments, the one or more nucleic acid sequences comprise small or short interfering RNAs (siRNAs).

In some embodiments, the method further comprises a step of culturing the sample and agent in a culture medium for about 24 hours to about 168 hours. In some embodiments, the method further comprises a step of culturing the sample and agent in a culture medium for about 72 hours to about 120 hours. In some embodiments, the method further comprises a step of culturing the sample and agent in a culture medium for about 120 hours.

In some embodiments, the method further comprises a step of culturing the sample and agent in a culture medium for about 1 day to about 7 days. In some embodiments, the method further comprises a step of culturing the sample and agent in a culture medium for about 3 days to about 5 days. In some embodiments, the method further comprises a step of culturing the sample and agent in a culture medium for about 5 days.

In some embodiments, the agent is ibrutinib and is provided once during the culturing. In some embodiments, the agent is ibrutinib and is provided on one or more of day 0, day 1, day 2, day 3, day 4 and day 5 during the culturing. In some embodiments, the agent is ibrutinib and is provided on one or more of day 0, day 3, day 4 and day 5 during the culturing. In some embodiments, the agent is ibrutinib and is present in the culture medium throughout the culturing. In some embodiments, the agent is ibrutinib and is provided prior to day 3 during said culturing. In some embodiments, the agent is ibrutinib an dis provided prior to day 1, prior to day 2, or prior to day 3 during said culturing. In some embodiments, the sample is cultured for about 24 hours, about 48 hours, about 72 hours, about 96 hours, about 120 hours, about 144 hours or about 168 hours after addition of ibrutinib to the culture medium.

In some embodiments, the sample is cultured for about 5 days to 3 weeks after addition of ibrutinib to the culture medium. In some embodiments, the sample is cultured no more than about 168 hours or about 7 days after addition of ibrutinib to the culture medium.

In some embodiments, the sample is cultured no more than about 3 weeks after addition of ibrutinib to the culture medium.

In some embodiments, the subject is a human patient. In some embodiments, the subject has not been previously treated with ibrutinib. In some embodiments, the subject has cancer. In some embodiments, the cancer is selected from the group consisting of chronic lymphocytic leukemia (CLL), acute lymphoblastic leukemia (ALL), acute myeloid leukemia (AML), chronic myeloid leukemia (CML), lymphomas, brain cancers, blood cancers and melanomas.

In some embodiments, the $T_{SCM}$ cells express one or more of the following: CD7, CD11a, CD27, CD45RA, CD58, CD95, CD127 and CCR7. In some embodiments, the $T_{SCM}$ cells do not express one or more of the following: CD45RO, CD57, LAG3, CTLA4 and PD1. In some embodiments, the $T_{SCM}$ cells produce more effector cytokines IFN-γ and TNF-α as compared to control effector cells. In some embodiments, the $T_{SCM}$ cells produce more of the proliferation-inducing cytokine IL-2 and less effector cytokines IFN-γ and TNF-α.

In some embodiments, the population of enriched $T_{SCM}$ cells is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or about 95% of the total cells in the culture. In some embodiments, the population of enriched $T_{SCM}$ cells is at least about 70% to about 90% of the total cells in the culture.

In some embodiments, the percentage of $T_{SCM}$ cells in the total T cells is increased by about 0.5-fold to about 200-fold after the culturing when compared to the percentage of $T_{SCM}$ cells in the total T cells prior to the culturing.

In some embodiments, the enriched $T_{SCM}$ cell population is isolated from the culture medium. In some embodiments, the enriched $T_{SCM}$ cell population is isolated and cryopreserved.

In another aspect, provided herein is a composition comprising a substantially pure population of $T_{SCM}$ cells wherein the population of $T_{SCM}$ cells is at least about 50%, about 55%, about 60%, about 65%, about 70%, about 75%, about 80%, about 85%, about 90% or about 95% of total T cells in the composition. In some embodiments, a population of $T_{SCM}$ cells is at least about 70% of total T cells in the composition. In some embodiments, a population of $T_{SCM}$ cells is at least about 70% to about 90% of total T cells in the composition.

In still another aspect, provided herein is a composition comprising a substantially pure population of $T_{SCM}$ cells produced according to any of the foregoing methods.

In some embodiments, the cells further comprise one or more pharmaceutically acceptable excipients. In some embodiments, the substantially pure population of $T_{SCM}$ cells comprises engineered T cells having chimeric antigen receptors (CARs) and/or engineered T cells having recombinant T cell receptors (TCRs).

In still another aspect, provided herein is a kit containing any of the foregoing compositions and instructions for use.

In still another aspect, provided herein is a method of treating a subject having or suspected of having cancer, the method including administering a therapeutically effective amount of a pharmaceutical composition to the subject, wherein the pharmaceutical composition comprises a population of T cells enriched in $T_{SCM}$ cells compared to a normal population of T cells.

In some embodiments, the population of enriched $T_{SCM}$ cells is produced according to any of the foregoing production methods. In some embodiments, the $T_{SCM}$ cells are autologous. In some embodiments, the $T_{SCM}$ cells are non-autologous. In some embodiments, the $T_{SCM}$ cells are allogeneic.

In some embodiments, the effective amount is about $1\times10^3$ to about $1\times10^8$ $T_{SCM}$ cells/kg of body weight of the subject. In some embodiments, the effective amount is about $1-5\times10^6$ $T_{SCM}$ cells/kg of body weight of the subject.

In some embodiments, the pharmaceutical composition is administered to the subject one time. In some embodiments, the pharmaceutical composition is administered to the subject 1-5 times. In some embodiments, the administered $T_{SCM}$ cells are removed from the subject after the cancer is substantially treated.

In some embodiments, the cancer is selected from the group consisting of chronic lymphocytic leukemia (CLL), acute lymphoblastic leukemia (ALL), acute myeloid leukemia (AML), chronic myeloid leukemia (CML), lymphomas, brain cancers, blood cancers and melanomas.

Each of the aspects and embodiments described herein are capable of being used together, unless excluded either explicitly or clearly from the context of the embodiment or aspect.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims

BRIEF DESCRIPTION OF THE DRAWINGS

FIG. 1A: A strategy for adapting CFSE dye dilution assay to mass cytometry.

FIGS. 2A-2F show that CFSE dilution-based cell proliferative history is quantitatively similar between flow cytometry and mass cytometry. FIG. 2A: Experimental outline for tracking T-cell proliferative history of naïve CD8+ T cells in the rapid expansion protocol (REP) as a model system. CFSE-labeled primary human T lymphocytes were induced to proliferate ex vivo using a rapid expansion protocol (REP), where T cells are incubated with accessory cells, including monocytes (Mo), which present an anti-CD3epsilon antibody via their Fcγ receptors (FcγRs) and express co-stimulatory molecules. To track fate of a specific subset, such as naïve T cells, the subset is magnetically enriched and labeled with CFSE prior to mixing with CFSE-negative accessory cells. Starting at 48 hours, interleukin-2 (IL-2) is added to sustain T-cell proliferation. Fixed samples were stored until the time course completion and analysis by both flow cytometry and mass cytometry. FIG. 2B: Proliferative history of CD8+ T cells is similar when measured directly by flow cytometry, or indirectly using a 172 Yb-labeled anti-FITC antibody by mass cytometry. Red arrows indicate division IDs of each CFSE peak. A division ID was assigned to each cell falling into the >80% confidence region (blue), and the remaining cells were left unassigned (division ID: −1). Appending a division ID column to the original file allows downstream analysis in software of choice, exemplified by plotting CFSE signal in assigned cells using Cytobank (www.cytobank.org). FIG. 2C: Spearman correlation analysis comparing percentage of cells falling into each division ID assigned to identical samples based on flow cytometry and mass cytometry. 25 samples were collected on days 0, 3, 4, 5, or 7. A division ID assigned to each data point is indicated using a color gradient. FIG. 2D: CFSE signal reduction per division was calculated based on geometric means from cells in (FIG. 2C). A red dashed line indicates the expected 50% reduction. FIG. 2E: A gating strategy demonstrating the utility of using CFSE labeling for tracking cell population of interest in a high-parameter mass cytometry assay. Magnetically enriched naïve T cells were labeled with CFSE and appear as CFSE-positive events among all cells in REP cultures shown on days 0 and 4. Naïve phenotype (CD45RA+ CD45RO−) is shown for CD8+ cells selected in silico. FIG. 2F: Features associated with fate selection are plotted for naïve CD8+ T cells over 7 days of REP culture. Mean division IDs and relative cell numbers are included for reference. Relative protein expression is shown on relevant scales: mean arsinh-transformed expression for CD45RA and CD45RO, or percent positive cells for activation markers (CD25, CD69), marker of translational activity phosphorylated ribosomal protein S6 (pRPS6), and marker of proliferation (Ki-67). Results in FIGS. 2B-2F are from 1 representative experiment of 3 replicate experiments performed.

FIGS. 3A-3D depict uncoupling time and division state in early differentiation of naïve CD8+ T cells which shows that lineage commitment is linked to both time and proliferation. Proliferative history shows consistent division-dependent behavior in early naïve T-cell differentiation. FIGS. 3A and 3C: Proliferative history tracing reveals consistent division state-dependent behavior during early differentiation of naïve CD8+ T cells. Violin plots show single-cell expression of activation markers CD25 (IL2Rα; left) or CD69 (right) on naïve CFSE+ CD8+ T cells cultured via REP for 0, 3, 4, 5, or 7 days as bulk cells (gray) or split by division ID (green gradient) relative to an average of naïve CD8+ T cells (black dotted line). In FIG. 3, single-cell expression (as in FIG. 3A) showing activation marker CD69. Red boxes indicate that cells with the lowest CD69 expression on day 3 cells have divided the most. FIG. 3B: Boxplots displaying average CD25 expression (as in FIG. 3A) from 6 samples shows consistent division-dependent trends on each day. FIG. 3D: Average CD69 expression (as in FIG. 3B). Results in FIGS. 3A-3D are from 1 representative experiment of 3 replicate experiments performed.

FIGS. 4A-4C depict discriminating time and division in early naïve T-cell differentiation which show that individual protein expression is controlled predominantly in division-dependent manner. FIG. 4A: A normalization scheme to examine time-987 and division state dependent changes as orthogonal dimensions. To focus on division state-dependent changes only, expression is divided by division 0 at the same timepoint. To focus on time-dependent changes only, expression is divided by the earliest timepoint with the same division ID (except day 0 to focus on activated cells). CD69 is shown as example. FIGS. 4B-1 and 4B-2: Changes in average division state-dependent expression (left) or time-dependent expression (right) of 23 markers (plus CD3ε, CD8α, CD45 that were also used for gating) in naïve CFSE+ CD8+ T cell samples (n=6) cultured via REP for 3, 4, 5, or 7 days. See Table 3 for additional information on each marker. Bar graphs show division ID distribution on each day as mean±s.e.m. FIG. 4C: A multivariate linear regression model to assess relative effects of time and division state on protein expression. Model coefficients and their p-values are shown as a heatmap for each marker. Results in (a-d) are from 1 experiment representative of 3 experiments.

FIG. 5A depicts an outline for constructing a force-directed graph examining single-cell phenotypic continuum. In this graph, 10,000 CFSE+ CD8+ T cells from day 3 of REP are repelled based on angular (cosine) distance calculated from arsinh-transformed expression of 21 surface proteins, whereas constant spring-like attractive forces are applied along connecting edges to create a balanced state. The edges connect each cell to its 10 nearest neighbors in a consecutive (−1, 0, +1) division state. Once constructed, the graph was used to assess distribution of 21 surface proteins, functional markers pRPS6 (translational activity) and Ki-67 (proliferation), or diffusion pseudo-time (DPT). FIG. 5B depicts a force-directed 1010 graph constructed as described in (FIG. 5A) showing division IDs for each cell. Division ID frequency distribution for this sample and each prominent region is shown as a bar. Marker expression was scaled to 0-100% range prior to calculating mean expression within each region. FIG. 5C: DPT was calculated using expression of the same 21 surface proteins and overlaid onto the graph from FIG. 5B, with color showing the most likely path based on diffusion transition probabilities towards two endpoints (DPT1 and DPT2). Arrows were drawn manually to serve as visual aids. FIG. 5D depicts histograms showing DPT1 and DPT2 distribution within each division ID (both scaled to 0-1 range to make values comparable). Red arrows indicate the narrowing in DPT standard deviation (s.d.) within each division; s.d. is shown on the top left of each plot. FIG. 5E depicts expression of CD25 (left, correlated with DPT1) and CD137 (right, correlated with DPT2) proteins overlaid onto the graph from (b), with Spearman's correlation to the relevant DPT value shown below. Results in FIGS. 5B-5E are from 1 donor representative of 5 donors from 3 experiments. FIG. 5F: An alternative metric for estimating high-dimensional phenotypic diversity by calculating cosine distance to an average cell among cells in each division ID. Here, a high average distance would indicate high phenotypic diversity, and low otherwise. Right panel shows that high dimensional phenotypic diversity can be estimated as an average cosine distance to an average cell within each division state. FIG. 5G: Boxplot showing phenotypic diversity among cells in each division ID on day 3 of REP estimated as described in FIG. 5F for 7 samples from 2 experiments.

FIGS. 6A, 6B-1, 6B-2, 6B-3, and 6C-6F show that Ibrutinib skews T-cell differentiation away from dysfunctional phenotype and towards $T_{SCM}$ phenotype. FIG. 6A depicts a summary on naïve CFSE+ CD8+ T-cell differentiation in REP, which converges onto two main subpopulations by day 7: a subset expressing increased levels of dysfunctional state markers (CD27− CTLA4+ LAG3+ PD1+; this includes a smaller subpopulation of cells expressing a senescence marker CD57) and $T_{SCM}$-like cells (CD45RA+ CD45RO− CD27+CD127+ CCR7+PD1− CTLA4− LAG3− CD57−). Day 3-5 cells on the path to increased dysfunction endpoint are pRPS6$^{High}$, whereas those on the path to $T_{SCM}$-like endpoint are pRPS6$^{Low}$. Functional properties of sorted increased dysfunction (Dysf) and $T_{SCM}$-like (TSCM) cells were assessed in re-stimulation experiments and are summarized on the right. Naïve CFSE+ T cells were treated with either vehicle (DMSO) or ibrutinib and collected from REP cultures on days 3, 4, 5, and 7. 134 naïve CFSE+ CD8+ T cells from day 0 and 6,000 CFSE+ CD8+ T cells/treatment from days 3, 4, 5, and 7 were pooled into a force-directed graph constructed using expression of 27 surface proteins, with edges connecting cells only in consecutive (−1, 0, +1) divisions.

FIGS. 6B-1, 6B-2, and 6B-3 shows that ibrutinib diminished T-cell differentiation towards dysfunctional (PD1+ CTLA4+) and closely related senescent (CD27− PD1+ CD57+) phenotype cells, and increased differentiation towards $T_{SCM}$ (CD45RA+ CD45RO− CD27+CD127+ CCR7+PD1− CTLA4− CD57−) phenotype cells. REP cultures were treated with either vehicle (DMSO) or ibrutinib, collected on days 0, 3, 4, 5, and 7, and assessed by mass cytometry using an antibody panel in Table 4. CFSE+ CD8+ T cells were 1077 pooled into a force directed graph constructed using expression of 27 surface proteins, with edges connecting cells only in consecutive (−1, 0, +1) divisions. Naïve T-cell differentiation can be observed across divisions (FIG. 6B-1), time (FIG. 6B-2), or DPT (FIG. 6B-3) when overlaid onto the graph. DPT was calculated using expression of the same 27 surface proteins (separately for each treatment condition), and then scaled from 0 to 1 to improve visibility (i.e. DPT values for ibrutinib appear inflated on average 2.2×). Graph regions were defined using individual marker expression. Observed trends are shown in red. Results were nearly identical when only proteins from the original panel (Table 2) were used instead of the extended panel (Table 4).

FIG. 6C shows that a signaling pathway links ibrutinib to pRPS6. pRPS6 overlaid onto the graph from FIGS. 6B-1, 6B-2, and 6B-3 and colored by treatment condition. T-cell differentiation is observed across divisions (FIG. 6B-1), time (FIG. 6B-2), or DPT (FIG. 6B-3) when overlaid onto the graph from FIG. 6A. DPT was calculated using expression of the same 27 surface proteins separately for each treatment, and then scaled from 0 to 1 (i.e., DPT values for ibrutinib appear inflated on average 2.2×). Graph regions were defined using individual marker expression (FIG. 8). Observed trends are shown in red. Arrows were drawn manually to serve as visual aids. Asterisks indicate the most likely path (according to DPT) towards $T_{SCM}$ phenotype that was enriched by ibrutinib. Arrows indicate the potential (according to DPT) of $T_{SCM}$ phenotype cells (DPT$^{Low}$) to reconstitute activated and differentiated cell subsets (DPT$^{High}$). Results were nearly identical when only proteins from the original panel (Table 2) were used instead of the extended panel (Table 4). Results in FIGS. 6B-1, 6B-2, 6B-3, and -6C are from 1 donor representative of 3 donors from 2 experiments.

FIG. 6D depicts a summary of potential cancer immunotherapy applications of the platform presented here. Tracing fate of CFSE+ TILs or CAR T cells across time and divisions in complex cell mixtures may be useful for rationally selecting timing and interventions for guiding T-cell fate during ex vivo expansion for ACT. These insights may be later used for designing better drugs to improve T-cell function in situ. Contour plots showing angular distances to an average $T_{SCM}$ or dysfunctional phenotype cell for vehicle and ibrutinib-treated cells on each day of REP culture. Angular distances were calculated based on the surface proteins used to define $T_{SCM}$ and dysfunctional gates. FIG. 6E: Boxplots showing data from (FIG. 6D) on days 3 and 7 across division IDs. Outliers are not shown. P-values were calculated using independent two-group Wilcoxon-Mann Whitney U test. *p<0.05, p<0.01, *p<0.001. FIG. 6F: A summary of potential cancer immunotherapy applications of the platform presented here. Tracing fate of CFSE+ T cells across time and divisions in complex cell mixtures will be useful for selecting an optimal intervention sequence for guiding T-cell fate during ex vivo expansion for ACT. These insights may be later used for designing better drugs to improve T-cell function in situ.

FIGS. 9A-9F show that single-cell RNA-sequencing uncovers the basis of undivided cell state diversity during early divergence in naïve CD8$^+$ T-cell differentiation. FIG. 9A shows an experimental outline: 10,000 CFSE+ CD8$^+$ T cells from divisions 0, 1, and 2 were sorted for droplet-based single-cell RNA-sequencing on day 3 of REP. Out of 19,222 genes detected in n=4,060 cells (division 0: n=522; division 1: n=1,777; division 2: n=1,731 were sequenced in 1 experiment), 1,000 most variably expressed genes were selected for subsequent analysis, including a force directed graph connecting consecutive (−1, 0, +1) division states, diffusion pseudo-time (DPT), individual gene expression, and phenotypic diversity. FIG. 9B: Fluorescence-activated cell sorting (FACS) gating strategy to sort out CFSE+ CD8+ T cells that divided 0, 1, or 2 times based on CFSE peaks. FIG. 9C: A force-directed graph constructed using data from FIG. 9A showing division IDs for each cell. Definition, cell number and percent, division ID frequency distribution, and expression of notable genes are shown for 4 regions of interest. FIG. 9D: in top left pane: DPT is shown overlaid onto the graph from FIG. 9C, with colors showing the most likely paths based on diffusion transition probabilities towards two endpoints (DPT1 and DPT2). Color scales were adjusted to emphasize separation of DPT1 and DPT2. Top right: expression of IFNG (encoding IFN-γ), an example of a gene highlighted in FIG. 9C; see FIGS. 10A-10C for additional examples. Bottom: expression of IL2RA (encoding CD25) and TNFSRSF9 (encoding CD137) indicate that DPT1 and DPT2 here may be equivalent to those shown in FIG. 5C. FIG. 9E: A violin plot with a boxplot showing phenotypic diversity of sorted CFSE+ CD8$^+$ T cells from FIG. 9A. Phenotypic diversity was calculated for each cell as an angular (cosine) distance to an average cell within each division state using expression of 1,000 most variably expressed genes. Kruskal-Wallis H test (one-way ANOVA on ranks): P=1.58e-177; Wilcoxon Mann-Whitney (WMW) U test comparing division 0 vs. division 1: P=3.96e-174, comparing division 0 vs. division 2: P=4.58e-135. WMW P-values were corrected for multiple hypotheses testing using Bonferroni correction. FIG. 9F: A heatmap showing expression of all genes expressed in >10 cells for 50 cells from each region highlighted in FIG. 9C; cells were selected based on DPT values (DPT$^{Low}$ for regions 1 and 4; DPT1$^{High}$ for region 3; DPT2$^{High}$ for region 2). Genes with relevance to T-cell biology are indicated below the heatmap, with color indicating expression specific to a given region; black color indicates expression in multiple regions.

FIGS. 10A-10C depict high-dimensional phenotypic diversity calculated based on single-cell RNA-sequencing decreases with division state. FIG. 10A: A violin plot with a boxplot showing phenotypic diversity of sorted CFSE+ CD8+ T cells within each division state on day 3 of REP (n=522 division 0 cells, n=1,777 division 1 cells, and n=1,731 division 2 cells were sequenced in 1 experiment). Phenotypic diversity was calculated for each cell as an angular (cosine) distance to an average cell within each division state using expression of all 19,222 detected genes. Kruskal-Wallis H test (one-way ANOVA on ranks): P=6.85e-67; Wilcoxon Mann-Whitney (WMW) U test comparing division 0 vs. division 1: P=1.60e-70, comparing division 0 vs. division 2: P=2.37e-41. FIG. 10AB: Phenotypic diversity was calculated for each cell from FIG. 10A as an angular distance to an average cell within each division state using expression of the same genes assessed by mass cytometry by time-of-flight (CyTOF) in FIG. 4. Kruskal-Wallis H test: P=1.14e-43; WMW U test comparing division 0 vs. division 1: P=8.29e-43, comparing division 0 vs. division 2: P=5.38e-33. FIG. 10C: Phenotypic diversity was calculated for each cell from FIG. 10A as a Euclidean distance to an average cell within each division state using expression of 1,000 most variably expressed genes. Kruskal-Wallis H test: P=1.58e-177; WMW U test comparing division 0 vs. division 1: P=3.96e-174, comparing division 0 vs. division 2: P=4.58e-135. WMW P-values in (a-c) were corrected for multiple hypotheses testing using Bonferroni correction.

FIGS. 11A-11C depict functional analysis of putative TSCM and dysfunctional T-cell subsets. FIG. 11A: Outline of the functional analysis experiments. CFSE+ naïve T cells were expanded using REP for 7 days. Next, putative TSCM and dysfunctional T-cell subsets were sorted out using FACS, re-labeled with CFSE, cultured with new autologous CFSE-negative accessory cells using REP for 3 days, and pulsed with IdU 30 minutes prior to collection and analysis by mass cytometry using an antibody panel in Table 8. FIG.

11B: FACS gating strategy to sort out putative TSCM and dysfunctional subsets based on the observed correlation in single-cell protein expression on day 7 of REP. Putative TSCM cells were defined as single live CD3ε+ CFSE+ antigen-experienced (divided >1 times) CD27+CD45RA+ PD1− events, and putative dysfunctional T cells were defined as single live CD3ε+ CFSE+ antigen-experienced CD27− PD1+ events. The post-sort purity of each subset was >90%. FIG. 11C: Contour plots showing mass cytometry analysis of putative TSCM and dysfunctional subsets on day 3 of re-stimulation (gated on live non-apoptotic CFSE+ CD8+ T cells). The functional analysis included the potential to proliferate (CD7 and CD27 expression; the percentage of cells in S phase quantified by IdU incorporation), persist (the percentage of apoptotic cPARP+ cells), and maintain desirable phenotype (lack of expression of dysfunctional markers CTLA4 and LAG3 and of senescence marker CD57). To measure the percentage of apoptotic (cPARP+) cells, the gating strategy excluded the cPARP− gate (gated on live CFSE+ CD8+ T cells).

FIG. 12A: Boxplots showing mean phenotypic diversity of CFSE+ CD8+ T cells within each division state on day 4 (left), day 5 (center), and day 7 (right) of REP (n=7 samples from 2 experiments). Results for day 3 are shown in FIG. 5H. Phenotypic diversity was calculated as an average angular (cosine) distance to an average cell within each division state using arsinh-transformed expression of 18 common surface proteins from antibody panels shown in Tables 2 and 4 that were not used for gating: CD7, CD25 (IL2Rα), CD27, CD28, CD38, CD45RA, CD45RO, CD57, CD69, CD134 (OX40), CD137 (4-1BB), CD127 (IL7Rα), CD150 (SLAMF1), CD197 (CCR7), CD223 (LAG3), CD272 (BTLA), CD278 (ICOS), and CD279 (PD1). FIG. 12B: Boxplot showing mean phenotypic diversity on REP days 3, 4, 5, and 7 (n=28 samples containing 4 timepoints from 2 experiments) calculated as an average Euclidean distance to an average cell within each division state using arsinhtransformed expression of 18 common surface proteins shown in FIG. 12A. FIG. 12C: Boxplots showing mean phenotypic diversity on REP days 3, 4, 5, and 7 (n=28 samples containing 4 timepoints from 2 experiments) calculated as described in (a) using arsinh-transformed expression of 15 randomly sampled surface proteins in 3 trials (excluded proteins are shown above each plot). To assess evidence for a decrease in phenotypic diversity with division in (FIGS. 12A-12C), linear mixed-effects models were used; slope±standard error (s.e.) and associated P-values are shown above each plot.

DETAILED DESCRIPTION

Figure 1A:
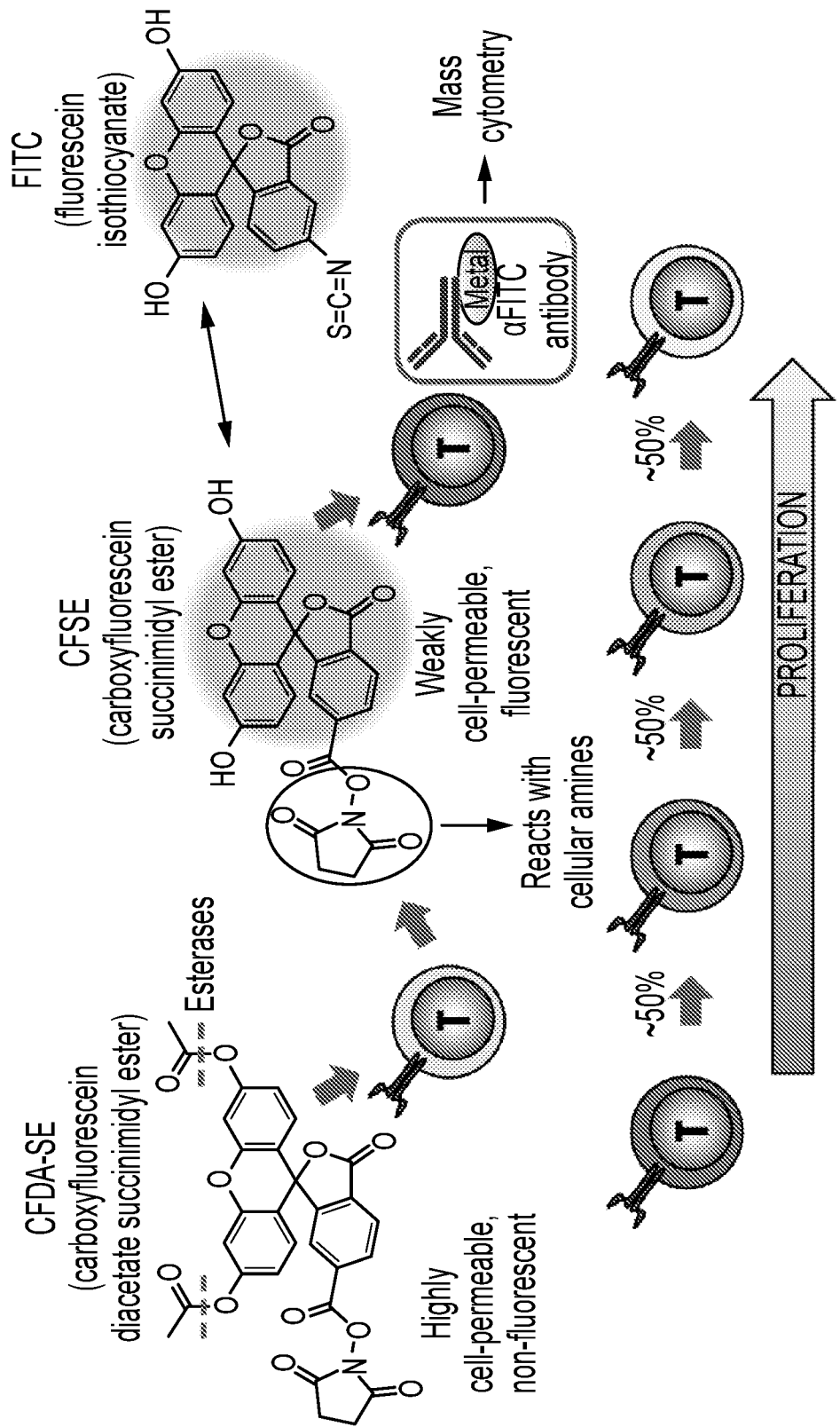
FIGS. 1A-IC depict detection of carboxyfluorescein succinimidyl ester (CFSE) by mass cytometry using affinity-based reagents.

The disclosures provide, inter alia, methods and compositions for expansion of T cell populations. In particular, the methods and compositions provided herewith can be used to expand a population of $T_{SCM}$ cells to produce a cell therapy product with improved therapeutic benefit in treating a variety of conditions including cancer.

Some embodiments of the disclosure relates to methods for producing a population of lymphocytes enriched in T stem cell memory cells ($T_{SCM}$ cells). Further provided are compositions containing a substantially pure population of $T_{SCM}$ cells that are therapeutically effective in treating various cancers, and kits containing such compositions. Methods for treating a subject having or suspected of having a cancer using the compositions and kits as disclosed herein are also provided.

Uncoupling the sequence of cellular transitions through phenotypic space in the context of time and division state is essential for creating better models of cellular differentiation. The present disclosure provides a platform for simultaneously tracing the proliferative history and phenotype of chemically labeled cells using highly multiplex single-cell mass cytometry. Building on the success of fluorescent dye dilution assays that are limited in dimensionality due to spectral overlap, this represents the first truly high-dimensional and high-throughput assay for tracing cell proliferative history. While applied to primary human T cells here, Applicant believes that this approach is generally applicable to tracing cell fate in complex mixtures for a variety of primary samples and cell lines, as well as with transplantation animal models where material or genetic tracing could be limited.

With this platform, one can generate a holistic view of both asynchronous and continuous cell behavior in activation-induced human T-cell specification. As illustrated in greater detail below, early differentiation of primary naïve CD8+ T cells in REP is intrinsically linked to division state. Using a comprehensive mass cytometry panel of T-cell specialization and exhaustion markers selected based on prior knowledge, it has been established that undivided cells had the highest phenotypic diversity at every time point examined. In particular, On day 3, when the majority of cells were in divisions 0-1, undivided cells spanned the differentiation map regions from the least differentiated ($CD45RA^{High}$ with CD69 expression) to the two most differentiated ($CD25^{High}$ and $CD25^{High}$ $CD137^{High}$) whereas divided cells were enriched in the most differentiated regions. Concurrently, single-cell transcriptome analysis revealed that these undivided T cells activate an effector gene expression program, including transcription factors (EOMES, HOPX, ID2; low TCF7), surface markers (KLRD1; low CCR7 and SELL), and effector molecules (GZMA, GZMH, PRF1, IFNG), while also expressing genes encoding CD25 (IL2RA) and CD137 (TNFRSF9). The other undivided cells either remained in the least differentiated state or expressed IL2RA and initiated a cell proliferation program (e.g. MKI67 encoding Ki-67). Single-cell gene expression also identified a small (1.5%) subpopulation of minimally differentiated and fast-proliferating cells that are highly enriched for gene expression associated with oxidative phosphorylation, a metabolic program thought to be critical for long-term T-cell persistence.

Definitions

Unless defined herein, all technical and scientific terms used herein have the same meaning as is commonly understood by one of skill in the art to which the claimed subject matter belongs. It is to be understood that the detailed descriptions are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included" is not limiting.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment. Any published patent applications and any other published references, documents, manuscripts, and scientific literature cited herein are incorporated herein by reference for any purpose. In addition, the materials, methods, and examples are illustrative only and not intended to be limiting.

Reference in the specification to "embodiments," "certain embodiments," "some embodiments," "an embodiment," "one embodiment" or "other embodiments" means that a particular feature, structure, or characteristic described in connection with those embodiments is included in at least some embodiments, but not necessarily all embodiments, of the disclosure.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within standard error of measurement.

The terms "isolate," "isolating," "isolated" and "isolation" refer to an action or state in which a compound or cell of interest is separated from all or some of the components that accompany it in nature. "Isolated" also refers to the state of a compound or cell of interest separated from all or some of the components that accompany it during manufacture (e.g., chemical synthesis, recombinant expression, culture medium, and the like).

The terms "purify," "purifying," "purified" and "purification" refer to an action or state in which a compound or cell of interest is isolated and further enriched prior to purification.

The term "non-naturally occurring" in the context of a compound or cell refers to a compound or cell that is not found in nature. For example, the term "non-naturally occurring T cell" refers to a T cell that is different from T cells found or present in nature. Thus, such non-naturally occurring T cells include recombinant T cells engineered to express a compound or construct that is not expressed in T cells found in naturally occurring T cells (e.g., a chimeric antigen receptor). Non-naturally occurring T cells can be engineered using various techniques available in the art, e.g., a broad range of genetic engineering methods.

The term "treatment" when referring to a disease or condition is used herein to mean that at least an amelioration of the symptoms associated with the condition afflicting an individual is achieved, where amelioration is used in a broad sense to refer to at least a reduction in the magnitude of a parameter, e.g., a symptom, associated with the disease or condition (e.g., cancer) being treated. As such, treatment also includes situations where the pathological condition, or at least symptoms associated therewith, are completely inhibited, e.g., prevented from happening, or eliminated entirely such that the host no longer suffers from the condition, or at least the symptoms that characterize the condition. Thus, treatment includes: (i) prevention, that is, reducing the risk of development of clinical symptoms, including causing the clinical symptoms not to develop, e.g., preventing disease progression; (ii) inhibition, that is, arresting the development or further development of clinical symptoms, e.g., mitigating or completely inhibiting an active disease.

The term "effective amount," "therapeutically effective amount" or "pharmaceutically effective amount" is an amount sufficient for a composition to accomplish a stated purpose relative to the absence of the composition (e.g., achieve the effect for which it is administered, treat a disease, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom means decreasing of the severity or frequency of the symptom(s), or elimination of the symptom(s). The exact amount of a composition comprising a "therapeutically effective amount" will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "pharmaceutically acceptable excipient" as used herein refers to any suitable substance that provides a pharmaceutically acceptable carrier, additive or diluent for administration of a compound(s) of interest to a subject. "Pharmaceutically acceptable excipient" can encompass substances referred to as pharmaceutically acceptable diluents, pharmaceutically acceptable additives, and pharmaceutically acceptable carriers.

The terms "disease," "disorder" and "condition" are used interchangeably herein and refer to a state of being or health status of a patient or subject capable of being treated with the methods and compositions provided herein. The disease includes, but not limited to, a cancer, an autoimmune disease, an inflammatory disease and an infectious disease.

As used herein, the term "cancer" refers to all types of cancer, neoplasm or malignant tumors found in mammals (e.g., humans), including leukemia, carcinomas and sarcomas. Exemplary cancers that are treated with a composition or method provided herein include cancer of the thyroid, endocrine system, brain, breast, cervix, colon, head & neck, liver, kidney, lung, non-small cell lung, melanoma, mesothelioma, ovary, sarcoma, stomach, uterus, colon and pancreas.

The terms "individual" and "subject" are used interchangeably to refer to any subject to be treated. The subject can be a mammal and in particular, a human being. Thus, the subject can be a human patient or an individual who has or is suspected of having a condition of interest (e.g., cancer) and/or one or more symptoms of the condition. The subject can also be an individual who is diagnosed with a risk of the condition of interest at the time of diagnosis or later.

The term "biological sample" refers to materials obtained from or derived from a subject or patient. A biological sample includes tissue sections such as biopsy and autopsy samples, and frozen sections taken for histological purposes. The biological samples also include bodily fluids such as blood and blood fractions or products (e.g., serum, plasma, platelets, red blood cells, and the like), sputum, tissue, cultured cells (e.g., primary cultures, explants, and transformed cells), immune cells, hematopoietic cells, fibroblasts, macrophages, T cells, etc. A biological sample is typically obtained from a eukaryotic organism, such as a human.

It is understood that aspects and embodiments of the disclosure described herein include "comprising," "consisting," and "consisting essentially of" aspects and embodiments.

Headings, e.g., (a), (b), (i) etc., are presented merely for ease of reading the specification and claims. The use of headings in the specification or claims does not require the steps or elements be performed in alphabetical or numerical order or the order in which they are presented.

Population of $T_{SCM}$ Cells and Methods of Making

The disclosure provides populations of T cells having stem cell memory phenotypes ($T_{SCM}$ cells) and methods for producing such populations of $T_{SCM}$ cells. These populations are enriched for $T_{SCM}$ cells which can be used for various therapies (e.g., adoptive cell therapy).

$T_{SCM}$ cells typically constitute a very small subset of T cells present in an animal. $T_{SCM}$ cells are generated from a subset of naïve T cells that is CD8$^+$. $T_{SCM}$ cells exist in a stem cell-like state, capable of clonal proliferation and sustaining their own population. Also, $T_{SCM}$ cells express a gene program that enables them to proliferate and differentiate into other T cell populations. Therefore, for example, CD8$^+$, $T_{SCM}$ cells with apparent self-renewal capabilities are capable of generating central memory T cell ($T_{CM}$) and effector memory T cell ($T_{EM}$) subsets that exhibit an immune response to a target disease or condition (e.g., cancer) while maintaining themselves. Because $T_{SCM}$ cells comprise such a small subset of an animal's total T cell complement, when a population of mixed T cells is isolated from, e.g., whole blood, mononuclear cells or bone marrow of a donor, the small number of $T_{SCM}$ cells that is isolated from the mixture may not be sufficient to use in adoptive cell therapy. While the isolated mixture of T cells, e.g., primary T cells, can be cultured in vitro for the purpose of expanding a number of clinically desirable $T_{SCM}$ cells, the stage of each T cell in the cultured cell mixture may also change over the course of culturing. In some cases, the naïve T cells or any other relatively undifferentiated T cells that were present in a primary T cell mixture can become dysfunctional T cells or senescent T cells. The term "dysfunctional (or exhausted) T cells," i.e., T cells having dysfunctional phenotypes, refers to a subset of reversibly cell cycle-arrested and poorly functional T cells (e.g., poor proliferation, higher apoptosis, reduced production of inflammatory cytokines and cytotoxic enzymes). In some embodiments, dysfunctional T cells express one or more certain specific cell surface markers, e.g., inhibitory receptors, including PD1, CTLA4 and/or CTLA4 (PD1$^+$ and/or CTLA4$^+$). The phenotypes of dysfunctional T cells may also include elevated (high) or diminished (low) expression of one or more of the following cell surface markers: CD45RA$^{Low}$, CD45RO$^{High}$, CD5$^{Low}$, CD7$^{Low}$, CD25$^{High}$, CCR7$^{Low}$, CD52$^{Low}$, CD69$^{High}$, CCR7$^{Low}$, LAG3$^{High}$ and DPT$^{High}$. The term "senescent T cells, i.e., T cells having a senescent phenotype," refers to a subpopulation of T cells defined by irreversible cell-cycle arrest and poor function. In some embodiments, senescent T cells have one or more specific markers expressed (shown as "+") or not expressed (shown as " ",) e.g., CD27$^-$ PD1$^+$ and/or CD57$^+$. These two subtypes of cells, i.e., dysfunctional T cells or senescent T cells are generally clinically undesirable T cells when a cell therapy, e.g., for cancer treatment is concerned. Thus, in some embodiments, a desired cell therapy composition comprises a composition enriched for clinically desirable cells (e.g., $T_{SCM}$ cells) or depleted of clinically undesirable cells (e.g., dysfunctional T cells and senescent T cells), for example, by sorting the cell types using their specific markers.

The disclosure further provides methods of producing a population of lymphocytes enriched in $T_{SCM}$ cells. In some embodiments, the population of lymphocytes enriched in $T_{SCM}$ cells is used in a cell therapy to treat a disease or condition of interest such as cancer.

In some embodiments, a population of lymphocytes enriched in $T_{SCM}$ cells is produced by contacting a sample that contains T cells with an agent that modulates a signaling pathway (i.e., a signaling pathway-modulating agent) in T cells. In some embodiments, the signaling pathway in T cells that is modulated is the Bruton's tyrosine kinase (BTK) signaling pathway and/or the inducible T cell kinase (ITK) signaling pathway.

The Bruton's tyrosine kinase (abbreviated Btk or BTK), also known as tyrosine-protein kinase BTK, is an enzyme that in humans is encoded by the BTK gene. BTK is a kinase that plays a crucial role in B cell development and maturation as well as in non-B cell development, e.g., mast cell activation through the high-affinity IgE receptor. Btk typically contains the Btk pleckstrin homology (PH) domain that binds phosphatidylinositol (3,4,5)-trisphosphate (PIP3). PIP3 binding induces Btk to phosphorylate phospholipase C, which in turn hydrolyzes PIP2, a phosphatidylinositol, into two second messengers, inositol triphosphate (IP3) and diacylglycerol (DAG), which then go on to modulate the activity of downstream proteins during B-cell signaling.

Tyrosine-protein kinase ITK/TSK, also known as interleukin-2-inducible T-cell kinase or simply ITK, is a protein that in humans is encoded by the ITK gene. ITK is a member of the TEC (tyrosine protein kinase) family of kinases and is highly expressed in T cells. This gene encodes an intracellular tyrosine kinase expressed in T-cells. The protein plays a role in T-cell proliferation and differentiation. Also, ITK is functionally important for the development and effector function of $T_H2$ and $T_H17$ cells.

In some embodiments, the modulation of BTK and/or ITK signaling pathways using the methods provided herein skews differentiation of T cells away from dysfunctional (exhausted) and/or senescent phenotypes and towards a more clinically desirable T stem cell memory ($T_{SCM}$) phenotype. Therefore, the methods provided herein provide a population of lymphocytes enriched in $T_{SCM}$ cells. In certain embodiments, the population of lymphocytes is a population of T cells. The agent (i.e., the BTK or ITK signaling pathway-modulating agent) of the disclosure is used in an amount sufficient to produce a population enriched in $T_{SCM}$ cells.

In some embodiments, the method comprises contacting a sample comprising naturally occurring T cells with a BTK or ITK signaling pathway-modulating agent. In some embodiments, the contact is performed ex vivo or in vitro, e.g., during in vitro cell culturing. In some embodiments, the sample is contacted with the agent in cell culture medium comprising the agent.

In some embodiments, the sample comprising naturally occurring lymphocytes comprises cells useful in adoptive cell therapy (e.g., T cells), such as $T_{SCM}$ cells or T cells capable of differentiating into $T_{SCM}$ cells, e.g., naïve T cells. In some embodiments, the sample is a biological sample obtained from a donor comprising naturally occurring T cells. In some embodiments, the biological sample comprises one or more of tumor-infiltrating lymphocytes (TILs), peripheral blood mononuclear cells (PBMCs), naïve T cells, and/or primary T cells. In some embodiments, TILs, PBMCs, naïve T cells and/or primary T cells are isolated or purified from the biological sample and then contacted with the BTK or ITK signaling pathway-modulating agent. Alternatively, T cells are not isolated or purified from the biological sample and the BTK or ITK signaling pathway-modulating agent is added directly to the biological sample ex vivo. In some embodiments, the primary T cells are de novo isolated T cells from an individual/primary biological sample that comprises multiple type of T cells including TILs and/or naïve T cells.

In some embodiments, the biological sample is obtained from an individual or subject. In an autologous cell therapy, the cells obtained from a biological sample are administered to the individual that provided the sample. In some embodiments, provided herein are improved compositions for adoptive cell therapy, and methods of making such compositions. In some embodiments, the adoptive cell therapy is autologous adoptive cell therapy. In some embodiments, the improved compositions comprise compositions enriched in $T_{SCM}$ cells (such as the $T_{SCM}$ cells produced by the methods disclosed herein). In some embodiments, the individual is a cancer patient. In some embodiments, the cancer patient suffers from or is suspected of suffering from a cancer selected from the group consisting of chronic lymphocytic leukemia (CLL), acute lymphoblastic leukemia (ALL), acute myeloid leukemia (AML), chronic myeloid leukemia (CML), lymphomas, solid cancers (e.g., brain cancers) and melanomas. In some embodiments, the cancer is a hematologic (e.g., blood) cancer that is not CLL.

In an allogeneic adoptive cell therapy, the cells obtained from a biological sample are not be obtained from the individual receiving the adoptive cell therapy. Allogeneic cell therapy refers to a therapy whereby the individual (donor) who provides the cell or biological sample is a different individual (of the same species) than the patient receiving the cell therapy. For example, a T cell population being administered to an individual is derived from one or more unrelated donors, or from one or more non-identical siblings. In certain embodiments, the adoptive cell therapy is an allogeneic adoptive cell therapy.

In some embodiments, the donor has not previously been treated with an agent that modulates a signaling pathway in T cells before a biological sample is taken or isolated from the donor. In other embodiments, the donor has not been administered an agent that modulates the BTK signaling pathway and/or ITK signaling pathway before a biological sample was taken from the donor. In some embodiments, the agent is ibrutinib and the donor has not been administered ibrutinib before a biological sample was taken from the donor. In some embodiments, the donor is administered ibrutinib after the biological sample is isolated. For example, ibrutinib is administered to a patient after his/her biological sample is isolated from the patient for the autologous cell therapy. This in vivo treatment of ibrutinib, after the isolation of the patient's sample, exhibits an additive or synergistic effect with the later-introduced enriched $T_{SCM}$ cell population in treating cancer. Thus, in certain cases, the biological sample is isolated from the patient about 0 hours (i.e., immediately before) to about 24 hours before ibrutinib is administered to the patient.

In some embodiments, the biological sample comprises one or more of the following: whole blood, leukapheresis product, peripheral blood mononuclear cells, TILs, biopsies, spleen and bone marrow isolated from an autologous or allogeneic donor.

In some embodiments, the biological sample comprises tumor-infiltrating lymphocytes (TILs). TILs are a complex mixture of many different types of immune cells (e.g., T cells, B cells, NK cells, macrophages) in variable proportions. TILs are implicated in antigen-specific killing of tumor cells and the presence of lymphocytes in tumors is often associated with improved clinical outcomes. In some embodiments, the TILs are isolated or obtained from a donor via a number of established protocols known to a person skilled in the art. For example, a biopsy sample comprising tumor cells is obtained from a donor and cells in the sample are dissociated. The dissociated cells undergo a sorting process, e.g., centrifugation or flow cytometry to separate TILs from other types of cells, e.g., cancer cells. In one example, the dissociated cells undergo staining and analysis by flow cytometry. Alternatively or in combination, the cell suspension is layered over a discontinuous Ficoll gradient comprising a 70% step and a 100% step, and centrifuged to separate tumor cells, which pellet at the interface, from enriched TILs. The enriched TILs are then washed in buffer or culture medium and then further processed as described herein.

In some embodiments, the biological sample comprises peripheral blood mononuclear cells (PBMCs). These cells include lymphocytes (e.g., T cells, B cells, and NK cells) and monocytes that are effective in adoptive cell therapy. In some embodiments, PBMCs are isolated or obtained from a donor via a number of established protocols known to a person skilled in the art (e.g., a manufacturer's protocol retrievable from www.fishersci.com/shop/products/ge-healthcare-ficoll-paque-plus-2/p-3753315.) For example, anticoagulants and/or defibrinated blood specimens are isolated and layered on top of a Ficoll solution, then briefly centrifuged to form different layers containing different types of cells. The bottom layer contains red blood cells (erythrocytes) which are isolated as a pellet. The next layer up from the bottom is primarily granulocytes, which also migrate down through the Ficoll solution. The next layer toward the top is the lymphocytes, which are typically at the interface between the plasma and the Ficoll solution, along with monocytes and platelets. To recover the lymphocytes, this layer needs to be recovered, washed with a salt solution to remove platelets, Ficoll, and plasma, and then centrifuged again. The enriched lymphocytes are then washed in a buffer or culture medium and then further processed as described herein. Any alternatives to Ficoll that can generate a density gradient suitable for cell separation can be used.

In some embodiments, the biological sample comprises naïve T cells. In some embodiments, the naïve T cells are human naïve T cells. In some embodiments, the naïve T cells (e.g., $T_H0$ cells) comprise T cells that have differentiated in bone marrow but have not yet encountered their cognate antigen. The naïve T-cell's activation and proliferation create an acquired immune response to a pathogenic agent of interest, e.g., cancer cells and specific antigens derived therefrom. In some embodiments, the naïve T cells are characterized by one or more of the following: the surface expression of L-selectin (CD62L); the absence of the activation markers CD25, CD44 or CD69; and the absence of memory CD45RO isoform. They also express functional heterodimeric IL-7 receptors comprising the IL-7 receptor-α subunit (IL7Rα or CD127) and the common-γ chain (CD132). Generally naïve T cells are quiescent and not actively dividing, requiring only a certain amount of IL-7 and IL-15 (two common-gamma chain cytokines) to survive until they encounter their cognate antigen and undergo further development. A subset of naïve T cells, e.g., $CD4^+$ and/or $CD8^+$ cells, differentiate into T cells with stem cell memory phenotype or $T_{SCM}$ cells, which exhibit clinical efficacy in treating a disease or condition of interest, e.g., cancer. After the disease is treated, a portion of the T cell population generated by the activated naïve T-cells, e.g., $T_{SCM}$ cells, constitutes a reservoir of memory cells, which proliferate and respond very quickly to any recurrence of the disease.

In some embodiments, the biological sample comprises primary T cells. In some embodiments, the primary T cells are human primary T cells. In some embodiments, the primary T cells comprise T cells that have been isolated from a patient or a healthy donor. In some embodiments, the primary T cells comprise a mixture of cells isolated from the subject. In some embodiments, the primary T cells comprise a mixture of cells isolated from the healthy donor. In some embodiments, the primary T cells have not undergone in vitro culturing at all. In some embodiments, the primary T cells have undergone in vitro culturing for a short time. In some embodiments, the short time comprises between about 0 days to a few days and up to about 15 days after isolation from a donor.

In some embodiments, the sample that is contacted with an agent modulating a signaling pathway in T cells according to the methods provided herein comprises non-naturally occurring T cells. In some embodiments, the non-naturally occurring T cells include engineered T cells. In some embodiments, the engineered T cells comprise cells having recombinant T cell receptors (TCRs) or T cells having chimeric antigen receptor (CARs).

In some embodiments, T cells used in the method provided herein are engineered T cells that comprise recombinant T cell receptors (TCRs). The TCR endows the T cell with the ability to recognize and respond to antigenic epitopes derived from foreign material or pathogens (e.g., cancer cells). In some embodiments, T cells obtained from a donor are engineered, e.g., via transfection of a recombinant nucleic acid sequence. The recombinant nucleic acid sequence encodes TCR receptors that bind to an antigen of interest, e.g., peptides present in target cancer cells. The engineered T cells then express recombinant TCRs and target the cells expressing cognate antigens of the recombinant TCRs (e.g., tumor antigens on a patient's cancer cells) when introduced to the patient. In some embodiments, the engineered T cells (e.g., T cells transfected with a recombinant nucleic acid sequence encoding TCRs) are contacted with the signaling pathway-modulating agent provided herein. In some embodiments, the contact occurs before the first division of the engineered T cells. In some embodiments, the contact occurs prior to expansion of the engineered T cells.

In some embodiments, the engineered T cells have chimeric antigen receptors (CARs). In some embodiments where CAR-T cells are used in an adoptive cell therapy, T cells are removed from a donor (e.g., a patient or a separate donor) and engineered so that they express receptors specific to the patient's particular cancer. The CAR-T cells that recognize and kill the cancer cells are reintroduced into the patient. In some embodiments, the CAR-T cells are contacted with the signaling pathway-modulating agent provided. In some embodiments, the contact occurs before the first division of CAR-T cells. In some embodiments, the contact occurs prior to expansion of CAR-T cells.

In some embodiments, the biological sample is contacted with the agent immediately after being isolated from a donor. In some embodiments, the biological sample is contacted with the agent between about 0 hours to about 72 hours after isolation from a donor. In some embodiments, the biological sample is contacted with the agent within about 12 hours, about 24 hours, about 36 hours, about 48 hours, about 60 hours, about 72 hours or any intervening period of the foregoing after the sample is isolated from a donor. In some embodiments, the biological sample is contacted with the agent at about 0 hours, about 12 hours, about 24 hours, about 36 hours, about 48 hours, about 60 hours, about 72 hours or any intervening period of the foregoing after the sample is isolated from a donor. In some embodiments, the biological sample is contacted with the agent no later than about 12 hours, about 24 hours, about 36 hours, about 48 hours, about 60 hours, about 72 hours or any intervening period of the foregoing after the sample is isolated from a donor.

In some embodiments, the biological sample is contacted with the agent before T cells in the sample undergo a first cell division after being isolated from a donor. In some embodiments, the biological sample is contacted with the agent prior to expansion of T cells after being isolated from a donor. In some embodiments, fluorescent dye dilution assays are used to estimate the number of cell divisions. In some embodiments, the fluorescent dye dilution assays are combined with flow cytometry or mass cytometry. In some embodiments, a mass cytometry assay is used to track cell proliferative history. In some embodiments, the mass cytometry assay employs carboxyfluorescein succinimidyl ester (CFSE) to detect cell division by fluorescence. As illustrated in an example from FIG. 1A, as cells go through mitosis, they pass ~50% of CFSE to each daughter cell, so mean fluorescence intensity provides a proxy for the number of times each cell has divided in a given sample. CFSE is administered to cells as carboxyfluorescein diacetate succinimidyl ester (CFDA-SE), a non-fluorescent precursor comprising multiple acetate groups, the presence of which renders CFDA-SE highly cell-permeable. Once CFDA-SE enters a cell, it is converted into the weakly cell permeable fluorescent molecule CFSE by cleavage of the acetate groups. CFSE contains an amine-reactive succinimidyl group, which mediates covalent binding to intracellular amine sources, including lysine. Since both CFSE and FITC are derivatives of fluorescein, CFSE can be quantified by mass cytometry via intracellular staining with an anti-FITC antibody conjugated to a reporter metal isotope. With each division, daughter cells inherit ~50% of CFSE. Thus, one can estimate the number of divisions (proliferative history) that a given cell undertook. Therefore, CFSE can be added to the biological sample or T cells isolated (or purified) from the biological sample and the pattern of CFSE dilution is measured to track down the cell division history of the cells. In some embodiments, the agent is contacted with the biological sample or purified T cells before at least about 10% to about 100% of the total cells (or total T cells) contained in the sample undergo a first cell division. Thus, for example, the agent is applied to a culture medium where the biological sample or purified T cells is/are cultured before at least about 10%, about 20%, about 30%, about 40%, about 50%, about 60%, about 70%, about 80%, about 90%, about 100% or any intervening percentage of the foregoing of the total cells (or total T cells) contained in the sample undergo a first cell division.

In some embodiments, the agent is contacted with the biological sample or purified T cells prior to expansion of the T cells. Thus, for example, the agent is applied to a culture medium where the biological sample or purified T cells is/are cultured before at least about 10%, about 20%, about 30%, about 40%, about 50%, about 60%, about 70%, about 80%, about 90%, about 100% or any intervening percentage of the foregoing of the total cells (or total T cells) contained in the sample initiate expansion.

In some embodiments, the biological sample is isolated from a donor and immediately placed into an in vitro culturing apparatus containing a culture medium. In some embodiments, the biological sample is further processed before being placed into an in vitro culturing apparatus containing a culture medium such that T cells are purified from the biological sample before the purified T cells are subject to in vitro culturing. In some embodiments, the agent that modulate a signaling pathway in T cells is added into the medium before the biological sample or purified T cells is/are provided such that the biological sample is exposed and contacted with the agent substantially immediately after being isolated from the donor. In some embodiments, the agent is added to the medium within about 12 hours, about 24 hours, about 36 hours, about 48 hours, about 60 hours, about 72 hours or any intervening number of hours of the foregoing after the biological sample is provided to the medium. In some embodiments, the agent is added to the medium at about 12 hours, about 24 hours, about 36 hours, about 48 hours, about 60 hours, about 72 hours or any intervening number of hours of the foregoing after the biological sample or purified T cells is/are provided to the medium. In some embodiments, the agent is added to the medium no later than about 12 hours, about 24 hours, about 36 hours, about 48 hours, about 60 hours, about 72 hours or any intervening number of hours of the foregoing after the biological sample or purified T cells is/are provided to the medium. In some embodiments, the agent is added to the medium prior to the first division of T cells contained in the sample or purified from the sample.

In some embodiments, the biological sample is cryopreserved after being isolated from a donor. In some embodiments, the biological sample is cryopreserved substantially immediately after being isolated from a donor. In some embodiments, the biological sample is cryopreserved for a few hours to a few days from isolation. In some embodiments, the biological sample is cultured for about 1 day, about 2 days or about 3 days after isolation and then cryopreserved. In some embodiments, the biological sample is further processed such that T cells are purified from the sample and subject to cryopreservation.

In some embodiments where the biological sample or purified T cells is/are cryopreserved after being isolated from a donor, the frozen sample or cells is/are thawed in a cell culture medium before proceeding to contact with the signaling pathway-modulating agent of the disclosure. In some embodiments, the biological sample or purified T cells is/are thawed and cultured in a cell culture medium for about 0 hour to about 72 hours before the contact with the agent. In some embodiments, the biological sample or purified T cells is/are thawed and cultured in a cell culture medium less than about 72 hours and proceeds to contact the agent. In some embodiments, the culturing period after thawing is relatively short such that T cells contained in the biological sample or purified from the sample do not undergo cell division prior to the contact with the agent.

In some embodiments, the method of disclosure utilizes an agent that modulates a signaling pathway in T cells. In some embodiments, the signaling pathway-modulating agent is an agent that modulates the BTK signaling pathway in T cells. In some embodiments, the signaling pathway-modulating agent is an agent that modulates the ITK signaling pathway in T cells. In some embodiments, the signaling pathway-modulating agent is an agent that modulates the BTK signaling pathway and the ITK signaling pathway in T cells. In some embodiments, the agent that modulates the BTK signaling pathway decreases the activity of BTK signaling pathway in T cells, without modulating the ITK signaling pathway. In some embodiments, the agent decreases the activity of ITK signaling pathway in T cells, without modulating the BTK signaling pathway. In some embodiments, the agent decreases the activities of both of the BTK signaling pathway and ITK signaling pathway in T cells.

In some embodiments, the signaling pathway-modulating agent provided herein comprises any compound that modulates the Bruton's tyrosine kinase (BTK) signaling pathway and/or the inducible T cell kinase (ITK) signaling pathway. In some embodiments, the signaling pathway modulating agent is PCI-32765 (ibrutinib), PRN694 (5-(difluoromethyl)-N-[5-[[[(2S)-3,3-dimethylbutan-2-yl]amino]methyl]-1-[[(2R)-1-prop-2-enoylpyrrolidin-2-yl]methyl]benzimidazol-2-yl]thiophene-2-carboxamide), BMS 509744 (N-[5-[[5-[(4-Acetyl-1-piperazinyl)carbonyl]-4-methoxy-2-methylphenyl]thio]-2-thiazolyl]-4-[[(1,2,2-trimethylpropyl)amino]methyl]benzamide), CTA 056 (1,5-Dihydro-7-(phenylmethyl)-1-[3-(1-piperidinyl)propyl]-2-[4-(4-pyridinyl)phenyl]-6H-imidazo[4,5-g]quinoxalin-6-one), GSK 2250665A (trans-4-[[4-[(6-Ethyl-2-benzothiazolyl)amino]-6-(phenylmethyl)-2-pyrimidinyl]amino]cyclohexanol), PF 06465469 ((R)-3-(1-(1-Acryloylpiperidin-3-yl)-4-amino-1H-pyrazolo[3,4-d]pyrimidin-3-yl)-N-(3-methyl-4-(1-methylethyl))benzamide) and any derivative thereof. In some embodiments, a single agent is used. In some embodiments, two or more agents are used in combination. In some embodiments, the agent is ibrutinib. In some embodiments, ibrutinib is used along with one or more agents in combination.

In some embodiments, the signaling pathway-modulating agent such as ibrutinib is used in an amount that is sufficient to modulate BTK signaling pathway and/or ITK signaling pathway in T cells. In some embodiments, ibrutinib is used in an amount sufficient to decrease the activity of one or both of the BTK signaling pathway and/or ITK signaling pathway. In some embodiments, ibrutinib is used in an amount sufficient to enrich a population of clinically desirable cells in a sample. In some embodiments, ibrutinib is used in an amount sufficient to produce a population of enriched $T_{SCM}$ cells in a sample.

In some embodiments, the signaling pathway-modulating agent is a nucleic acid sequence that modulates the BTK signaling pathway and/or ITK signaling pathway in T cells. In some embodiments, the nucleic acid sequence that modulates the BTK signaling pathway is a short, interfering RNA (siRNA) capable of silencing one or more genes in the BTK signaling pathway in T cells by RNA interference (RNAi). In some embodiments, the nucleic acid sequence that modulates the ITK signaling pathway is siRNA capable of silencing one or more genes in the ITK signaling pathway in T cells by RNA interference (RNAi). In some embodiments, the agent based on RNAi decreases the activity of one or both of BTK signaling pathway and/or ITK signaling pathway in T cells. RNAi generally refers to a biological process in which RNA molecules inhibit gene expression or translation, e.g., by neutralizing targeted mRNA molecules. Small interfering RNA (siRNA), sometimes known as short interfering RNA or silencing RNA, is a class of double-stranded RNA molecules, about 20-25 base pairs in length and operating within the RNA interference (RNAi) pathway. SiRNAs interfere with the expression of specific genes with complementary nucleotide sequences by causing, e.g., degrading mRNA after transcription, reducing and/or preventing translation. Thus, in some embodiments the agent used in the method of the disclosure is a small or short interfering RNA (siRNA) that targets mRNA of one or more genes, the activity of which is involved in the BTK signaling pathway and/or ITK signaling pathway in T cells. In some embodiments, the agent is one or more siRNAs targeting the genes that promote the activity of BTK signaling pathway and/or ITK signaling pathway in T cells. This siRNA-based agent can reduce the activity of such genes by, e.g., degradation of mRNA of the genes and/or reduction or prevention of translation. Therefore, it results in decreasing the activity of signaling pathway in which the genes targeted by SiRNAs are involved. In some embodiments, the genes targeted by the siRNA-based agent includes, but not limited to, Bruton's tyrosine kinase (btk gene) interleukin-2-inducible T cell kinase (itk gene), linker for activation of T cells (lat gene), spleen tyrosine kinase (syk gene) and tyrosine kinase (chain-associated protein kinase of 70 kD (zap70 gene).

In some embodiments, the concentration of the signaling pathway-modulating agent used in the method of the disclosure can be about 1 ng to about several milligrams to grams per ml. Thus, in some embodiments, the concentration of the agent, e.g., ibrutinib, used in the method is about 1 ng/ml, about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 250 ng/ml, about 300 ng/ml, about 350 ng/ml, about 400 ng/ml, about 450 ng/ml, about 500 ng/ml, about 550 ng/ml, about 600 ng/ml, about 650 ng/ml, about 700 ng/ml, about 750 ng/ml, about 800 ng/ml, about 850 ng/ml, about 900 ng/ml, about 950 ng/ml, about 1 µg/ml, about 10 µg/ml, about 20 µg/ml, about 30 µg/ml, about 40 µg/ml, about 50 µg/ml, about 60 µg/ml, about 70 µg/ml, about 80 µg/ml, about 90 µg/ml, about 100 µg/ml, about 150 µg/ml, about 200 µg/ml, about 250 µg/ml, about 300 µg/ml, about 350 µg/ml, about 400 µg/ml, about 450 µg/ml, about 500 µg/ml, about 550 µg/ml, about 600 µg/ml, about 650 µg/ml, about 700 µg/ml, about 750 µg/ml, about 800 µg/ml, about 850 µg/ml, about 900 µg/ml, about 950 µg/ml, about 1 mg/ml, about 3 mg/ml, about 5 mg/ml, about 7 mg/ml, about 10 mg/ml, or any intervening concentration of the foregoing. In some embodiments, the concentration of ibrutinib used in the method is about 10 ng/ml to about 10 µg/ml. In some embodiments, the concentration of ibrutinib used in the method is about 100 ng/ml to about 2 µg/ml.

In some embodiments, the method of the disclosure includes a step of culturing a sample in a culture medium. In some embodiments, the T cells are purified from the sample and cultured in a medium. In some embodiments, the sample or purified T cells are cultured for about 24 hours to about 168 hours. In some embodiments, the culturing period is about 24 hours, about 48 hours, about 72 hours, about 96 hours, about 120 hours, about 144 hours, about 168 hours or any intervening period of the foregoing. In some embodiments, the culturing period is about 72 hours to about 120 hours. In some embodiments, the culturing period is about 120 hours. In some embodiments, the signaling pathway modulating agent (e.g., ibrutinib) is provided to the culture once, e.g., at the beginning of the culturing. In some embodiments, the signaling pathway-modulating agent is provided to the culture more than once, e.g., 1, 2, 3, 4, or 5 times per day or during the culture period. In some embodiments, the signaling pathway-modulating agent is provided to the culture after day 3. In some embodiments, the signaling pathway-modulating agent is provided to the culture before day 3 of REP. In some embodiments, the signaling pathway-modulating agent is present in the culture medium throughout the culture period.

In some embodiments, the sample or purified T cells is/are cultured for about 1 day to about 7 days. In some embodiments, the culturing period is about 1 day, about 2 days, about 3 days, about 4 days, about 5 days, about 6 days, about 7 days or any intervening period of the foregoing. In some embodiments, the culturing period is about 3 days to about 5 days. In some embodiments, the culturing period is about 5 days. In some embodiments, the agent modulating a signaling pathway in T cells is provided to the culture once, e.g., at the beginning of the culturing. In some embodiments, the signaling pathway-modulating agent is provided to the culture once but delayed after day 3 during the culture period. In some embodiments, the signaling pathway-modulating agent is provided to the culture before day 3 of REP. In some embodiments, the signaling pathway-modulating agent is provided to the culture more than once, e.g., 1, 2, 3, 4, or 5 times during the culture period. In some embodiments, the signaling pathway-modulating agent is provided to the culture more than once, e.g., 1, 2, 3, 4, or 5 times during the culture period, but the first provision of the signaling pathway-modulating agent to the culture is delayed after day 3 during the culture period. In some embodiments, the signaling pathway-modulating agent is provided to the culture more than once, e.g., 1, 2, 3, 4, or 5 times during the culture period, but the first provision of the signaling pathway-modulating agent to the culture take places before day 3 of REP. In some embodiments, the signaling pathway-modulating agent is provided to the culture on one or more of days 0, 1, 2, 3, 4, or 5 during the culture period. In some embodiments, the signaling pathway-modulating agent is provided to the culture on one or more of days 0, 3, 4, or 5 during the culture period. In some embodiments, the signaling pathway-modulating agent is present in the culture medium throughout the culture period, e.g., for any period of from about 1 day to about 7 days.

In some embodiments, the sample or purified T cells is/are cultured for about 24 hours, about 48 hours, about 72 hours, about 96 hours, about 120 hours, about 144 hours or about 168 hours after the signaling pathway-modulating agent is first provided to the culture. In some embodiments, the sample or purified T cells is/are cultured for about 5 days to 3 weeks after the signaling pathway-modulating agent is first provided to the culture. In some embodiments, the sample or purified T cells is/are cultured no more than about 168 hours or about 7 days after the first provision of the signaling pathway-modulating agent. In some embodiments, the sample or purified T cells is/are cultured no more than about 3 weeks after the first provision of the signaling pathway-modulating agent.

In some embodiments, the agent used in the method of the disclosure modulates the BTK signaling pathway and/or ITK signaling pathway in T cells. Treatment with or application of the signaling pathway-modulating agent to the sample or isolated T cells skews differentiation of the T cells present in the sample away from dysfunctional (e.g., exhausted and/or senescent) phenotypes (e.g., one or more of $CD45RA^{Low}$, $CD45RO^{High}$ $CD5^{Low}$, $CD7^{Low}$, $CD25^{High}$, $CD27^{Low}CD52^{Low}$, $CD69^{High}$, $CCR7^{Low}$, $LAG3^{High}$, $CD27^-$, $PD1^+CD57^+$ and $CTLA4^+$) towards TSCM cells. Alternatively or in combination with the foregoing, treatment with the signaling pathway-modulating agent causing Tcells to have $T_{SCM}$ phenotypes (e.g., one or more of $CD4^+$, $CD8^+$, $CD7^+$, $CD11a^+$, $CD27^+$, $CD45RA+$, $CD45RO^-$, $CD57^-$, $CD58^+$, $CD95^+$, $CD127^+$, $CCR7^+$, $LAG3$ $CTLA4^-$ and/or $PD1^-$.) As a result of one or both of the foregoing mechanisms, $T_{SCM}$ cells, after treatment with the agent, are enriched in the total mixture of cells. Also, a population of non-$T_{SCM}$ cells decreases by the treatment of the agent. Therefore, in some embodiments the method of the disclosure provides a population of enriched $T_{SCM}$ cells.

In some embodiments, the percentage of $T_{SCM}$ cells in the total cells after the treatment with the agent is increased when compared to the percentage of $T_{SCM}$ cells in the total cells prior to the treatment with the agent. In some embodiments the increase in the percentage of $T_{SCM}$ cells following treatment with the agent is about 0.5 fold to about several hundred-fold. In some embodiments, the percentage of $T_{SCM}$ cells in the total cells present in the sample is increased by about 0.5-fold (i.e., a 50% increase), about 1-fold (i.e., a 100% increase), about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 200-fold, about 500-fold or any intervening number of -fold increase of the foregoing when compared to the percentage of $T_{SCM}$ cells in the total cells prior to the treatment with the agent.

In some embodiments, the initial percentage of $T_{SCM}$ cells in a sample prior to contacting with the signaling pathway-modulating agent is about or less than about 0.5% to about 30% of the total cells. In some embodiments, the initial percentage of $T_{SCM}$ cells in the sample is about or less than about 0.5%, about 1%, about 2%, about 3%, about 4%, about 5%, about 10%, about 15%, about 20%, about 25%, about 30% or any intervening percentage of the foregoing. In some embodiments, after contacting with the agent, the percentage of $T_{SCM}$ cells in the sample becomes about or more than about 5% to about 100% of the total cells. In some embodiments, the percentage of $T_{SCM}$ cells in the sample that is increased by contact with the agent is about 5%, about 6%, about 7%, about 8%, about 9%, about 10%, about 20%, about 30%, about 40%, about 50%, about 60%, about 70%, about 80%, about 90%, about 100% or any intervening percentage of the foregoing of the total cells.

In some embodiments, contacting the sample with the signaling pathway-modulating agent of the disclosure decreases the percentage or number of non-$T_{SCM}$ cells in a sample. Non-$T_{SCM}$ cells are any cells that do not have T stem cell memory phenotype, e.g., one or more of $CD45RA^{Low}$, $CD45RO^{High}$, $CD5^{Low}$, $CD7^{Low}$, $CD25^{High}$, $CD27^{Low}$, $CD52^{Low}$, $CD69^{High}$, $CCR7^{Low}$, $LAG3^{High}$, $CD27^-$, $PD1^+$ $CD57^+$ and/or $CTLA4^+$. In some embodiments, the non-$T_{SCM}$ cells include undifferentiated T cells (e.g., naïve T cells) or T cells that were differentiated to other than $T_{SCM}$ cells (e.g., central memory and effector T cells) as well as dysfunctional (exhausted) T cells and/or senescent T cells.

In some embodiments, a percentage of non-$T_{SCM}$ cells in the total cells present in a sample is decreased when compared to a percentage of non-$T_{SCM}$ cells in the total cells prior to the treatment with the agent. Thus, in some embodiments the decrease in the percentage of non-$T_{SCM}$ cells in the sample that is caused by the treatment with the agent is about 0.5-fold to about several hundred-fold. In some embodiments, the percentage of non-$T_{SCM}$ cells in the total cells present in the sample is decreased by about 0.5-fold, about 1-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 200-fold, about 500-fold or any intervening number of -fold increase of the foregoing when compared to a percentage of non-$T_{SCM}$ cells in the total cells prior to the treatment with the agent.

In some embodiments, the initial percentage of non-$T_{SCM}$ cells in a sample prior to the contact with the signaling pathway-modulating agent is about or more than about 0.5% to about 100% of the total cells. In some embodiments, the initial percentage of $T_{SCM}$ cells in the sample is about or less than about 0.5%, about 1%, about 5%, about 10%, about 20%, about 30%, about 40%, about 50%, about 60%, about 70%, about 80%, about 90%, about 100% or any intervening number of percentage of the foregoing. In some embodiments, after contact with the agent, the percentage of non-$T_{SCM}$ cells in the sample becomes about or less than about 0% to about 50% of the total cells. In some embodiments, the percentage of non-$T_{SCM}$ cells in the sample after contact with the agent is about 0%, about 1%, about 5%, about 10%, about 15%, about 20%, about 25%, about 30%, about 35%, about 40%, about 45%, about 50%, or any intervening percentage of the foregoing of the total cells compared to the percentage of $T_{SCM}$ cells in the sample prior to contact with the agent.

In some embodiments, the number of non-$T_{SCM}$ cells present in a sample is decreased by the treatment with the agent when compared to the number of non-$T_{SCM}$ cells in the sample prior to the treatment. In some embodiments, the decrease in the number of non-$T_{SCM}$ cells in the sample that is caused by the treatment of the agent is about 5% to about several hundred %. In some embodiments, the number of non-$T_{SCM}$ cells in the sample is decreased by about 5%, about 10%, about 20%, about 30%, about 40%, about 50%, about 60%, about 70%, about 80%, about 90%, about 100%, about 200%, about 500% or any intervening percentage of the foregoing when compared to the initial number of non-$T_{SCM}$ cells prior to the treatment with the agent.

In some embodiments, the population of enriched $T_{SCM}$ cells produced by the method of disclosure is about 5% to about 100% of the total cells in a culture. In some embodiments, the enriched $T_{SCM}$ cells constitute about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100% or any intervening percentage of the total cells in the culture. In some embodiments, the population of enriched $T_{SCM}$ cells produced by the method of disclosure is about 70% to about 90% of the total cells in the culture.

In some embodiments, the enriched $T_{SCM}$ cells produced by the method of disclosure are isolated from the culture media and/or cryopreserved before proceeding to a cell therapy.

Therapeutic Cell Compositions, Pharmaceutical Compositions and Kits

The disclosure provides, inter alia, improved compositions for use in cell therapy. In some embodiments, the composition comprises a population of cells for an adoptive cell therapy for cancer treatment. These compositions, which are enriched in $T_{SCM}$ cells, exhibit a desirable effect such as targeting and killing cancer cells. Such cells are considered to be clinically effective cells. In some embodiments, the compositions of the disclosure are administered to a cancer patient and mediate an immune response to cancer cells, thereby treating the patient's cancer.

In some embodiments, the composition of the disclosure comprises a therapeutic composition. In some embodiments, the therapeutic composition comprises therapeutically effective cells and is used in an in vivo treatment method. In some embodiments, the therapeutic composition comprises a population of clinically desirable T cells, e.g., $T_{SCM}$ cells having a stem cell memory phenotype (e.g., one or more of CD7$^+$, CD11a$^+$, CD27$^+$, CD45RA$^+$, CD45RO$^-$, CD57$^-$, CD58$^+$, CD95$^+$, CD127$^+$, CCR7$^+$, LAG3$^-$, CTLA4$^-$ and/or PD1$^-$). In some embodiments, the therapeutic composition comprises a population of naturally occurring T cells and/or engineered T cells that express chimeric antigen receptors (CARs) or recombinant T cell receptors (TCRs).

In some embodiments, the therapeutic composition of the disclosure contains a population of lymphocytes enriched for $T_{SCM}$ cells. Therefore, the $T_{SCM}$ cells in the composition are enriched relative to other non-$T_{SCM}$ cells. In some embodiments, the composition comprises an enriched d population of $T_{SCM}$ cells that comprises at least about 50% or more of the total cells in the composition. In some embodiments, the composition comprises at least about 50% or more $T_{SCM}$ cells out of the total number of cells in the composition. In some embodiments, the $T_{SCM}$ cells in the composition comprises at least about 50%, about 55%, about 60%, about 65%, about 70%, about 75%, about 80%, about 85%, about 90%, about 95%, about 100% or any intervening percentage of the foregoing of the total cells of the composition. In some embodiments, the $T_{SCM}$ cells in the composition comprises at least about 70% to about 90% of the total cells in the composition. In some embodiments, the composition comprises at least about 70% $T_{SCM}$ cells out of the total number of cells in the composition.

In some embodiments, the therapeutic compositions of the disclosure produced by any of the methods provided herein skew differentiation of T cells towards $T_{SCM}$ phenotypes and/or away from dysfunctional, exhausted, and/or senescent phenotypes. In some embodiments, this production method includes contacting a sample comprising T cells with an agent that modulates a signaling pathway in T cells (i.e., a signaling pathway-modulating agent) in the cells. In some embodiments, the agent modulates the BTK signaling pathway and/or ITK signaling pathway in T cells. In some embodiments, the agent is used in an amount sufficient to produce a population of enriched $T_{SCM}$ cells. In some embodiments, this method increases the percentage or number of T cells having stem cell memory phonotypes (e.g., one or more of CD4$^+$, CD8$^+$, CD7T$^+$, CD11a$^+$, CD27$^+$, CD45RA$^+$, CD45RO$^-$, CD57$^-$, CD58$^+$, CD95$^+$, CD127$^+$, CCR7$^+$, LAG3$^-$, CTLA4$^-$ and PD1$^-$) in total cells in the sample. Alternatively or in combination, In some embodiments the method also decreases the percentage or number of T cells having a dysfunctional, exhausted, and/or senescent phenotype (e.g., one or more of CD45RA$^{Low}$ CD45RO$^{High}$, CD5$^{Low}$, CD7$^{Low}$, CD25$^{High}$ CD27$^{Low}$, CD52$^{Low}$, CD69$^{High}$ CCR7$^{Low}$, LAG3$^{High}$ CD27$^-$, PD1$^+$ CD57$^+$ and CTLA4$^+$) in total cells. As a result, the population of cells produced by the method comprises a population enriched in $T_{SCM}$ cells.

In some embodiments, the therapeutic compositions provided herein are formulated for administration to a human subject as an adoptive cell therapy. In some embodiments, the compositions provided herein are pharmaceutical compositions further comprising a pharmaceutically acceptable excipient and/or a pharmaceutically acceptable carrier.

In some embodiments, the pharmaceutical compositions provided herein are administered as a cell suspension formulated with a pharmaceutically acceptable carrier. One of skill in the art will recognize that a pharmaceutically acceptable carrier to be used in a cell composition will include buffers, compounds, cryopreservation agents, preservatives, or other agents, provided they are not used in amounts that substantially interfere with the viability of the cells to be delivered to the subject. In some embodiments, a formulation comprising T cells enriched in $T_{SCM}$ cells includes, e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the therapeutic cells or engineered cells, as described herein, using routine experimentation.

Physiologically acceptable carriers are well known in the art. Exemplary liquid carriers are sterile aqueous solutions that contain no materials other than the active ingredients and water, or contain a buffer such as sodium phosphate at physiological pH, physiological saline or both, such as phosphate-buffered saline. Still further, aqueous carriers can contain more than one buffer salt, as well as salts such as sodium chloride and potassium chloride, dextrose, polyethylene glycol and other solutes. Liquid compositions can also comprise non-aqueous liquids. Exemplary non-aqueous liquids include glycerin, vegetable oils such as cottonseed oil, and water-oil emulsions.

In some embodiments, the pharmaceutical composition of the disclosure is used in conjunction with one or more additional therapeutic agents, e.g., anti-cancer drugs and/or chemotherapy agents). In some embodiments, such additional therapeutic agents are suitably administered in combination in amounts that is effective for the purpose intended, e.g., treatment of cancer.

In some embodiments, provided herein is a kit that contains any of the above-described compositions, e.g., a therapeutic cell composition and one or more additional components. In some embodiments, the kit has one or more additional therapeutic agents (e.g. anti-cancer drugs or chemotherapy agents) that can be administered in conjunction with the cell composition for a desired purpose, e.g., treatment of cancer.

In some embodiments, the kit of the disclosure further includes instructions for using the components of the kit to practice the methods. The instructions for practicing the methods are generally recorded on a suitable recording medium. For example, the instructions are printed on a substrate, such as paper or plastic, etc. The instructions are present in the kits as a package insert, in the labeling of the container of the kit or components thereof (e.g., associated with the packaging or sub-packaging), etc. The instructions are present as an electronic storage data file present on a suitable computer readable storage medium, e.g., CD-ROM, diskette, flash drive, etc. In some instances, the actual instructions are not present in the kit, but means for obtaining the instructions from a remote source (e.g., via the Internet), are provided. An example of this embodiment is a kit that includes a web address where the instructions are viewed and/or from which the instructions are downloaded. As with the instructions, this means for obtaining the instructions is recorded on a suitable substrate.

Therapeutic Approaches

In another aspect, provided herein are methods of treating a subject having a disease or condition with a pharmaceutical composition enriched in $T_{SCM}$ cells as further provided herein. In some embodiments, the method comprises administration of naturally occurring or engineered T cells that have a desired therapeutic efficacy, e.g., treating a cancer in the subject.

Adoptive cell therapy (ACT) generally refers to therapies comprising administration of cell infusions comprising clinically desirable (or effective) immune cells into a subject, e.g., a cancer patient. In some embodiments, the immune cells are autologous (i.e., originating from the patient). In some embodiments, the immune cells are allogeneic (i.e., originating from another individual, e.g., a healthy donor). In some embodiments, the autologous or allogeneic immune cells can be genetically modified or used without further modification. In some embodiments, these therapeutic T cells are cultured in vitro before returning to the same patient. Alternatively, allogeneic therapies involves cells isolated, optionally modified and expanded from a donor separate from the patient receiving the cells.

The method provided herein includes administering an effective amount of a therapeutic composition to a subject having or suspected of having cancer. In some embodiments, the therapeutic composition comprises a population of therapeutically effective or desired T cells, e.g., $T_{SCM}$ cells. Such T cells include naturally occurring T cells and/or engineered T cells.

In some embodiments, the therapeutic method of the disclosure comprises a step of administering a population of enriched $T_{SCM}$ cells to a subject in need of treatment. In some embodiments, the therapeutic method of the disclosure is a therapy that utilizes cells isolated from a donor. In some embodiments, the therapy is autologous such that the donor is the patient who will receive the therapy. In some embodiments, the therapy is non-autologous. The isolated cells are produced by the methods described herein. In some embodiments, the resulting population of enriched $T_{SCM}$ cells is administered to the patient for treatment.

In some embodiments, the subject in need of treatment is a patient having cancer. In some embodiments, the subject is a human suspected of having cancer. Alternatively, the subject can be a human at risk of developing cancer.

The therapeutic method of the disclosure can be applicable to any types of cancer. Some non-limiting examples of cancer subject to the therapeutic method of the disclosure include, any types of hematologic malignancies such as leukemia (e.g., chronic lymphocytic leukemia (CLL), acute lymphoblastic leukemia (ALL), acute myeloid leukemia (AML), chronic myeloid leukemia (CML), lymphomas (Hodgkin lymphoma and non-Hodgkin lymphoma), myeloma as well as solid cancers such as brain cancers and melanomas. In some embodiments, the cancer is a blood cancer that is not leukemia.

Implants and Grafts

In some embodiments, the method of the disclosure involves implanting or grafting the therapeutically effective cells, e.g., $T_{SCM}$ cells into a subject who is in need of such a method. This implanting step can be accomplished by using any method of implantation known in the art. For example, the therapeutically effective cells, especially a population of enriched $T_{SCM}$ cells can be injected directly in the subject's blood or otherwise administered to the subject. In alternative embodiments, the therapeutically effective cells are delivered into the subject via other methods described herein, e.g., intravenous injection.

In some embodiments, the delivery of a therapeutic cell composition into a subject by a method or route results in at least partial localization of the cell composition at a desired site. A cell composition can be administered by any appropriate route that results in effective treatment in the subject, e.g., administration results in delivery to a desired location in the subject where at least a portion of the composition delivered, e.g., at least $1-5 \times 10^6$ cells are delivered to the desired site for a period of time. Modes of administration include injection, infusion and instillation. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrastemal injection and infusion. In some embodiments, the preferred route of administration is intravenous.

In one embodiment, the cells are administered systemically, in other words a population of therapeutic cells are administered other than directly into a target site, tissue, or organ, such that it enters, instead, the subject's circulatory system.

The therapeutic cells can be administered by any appropriate route that results in delivery to a desired location in the subject where at least a portion of the implanted cells or components of the cells remain viable. The period of viability of the cells after administration to a subject may vary and can be the lifetime of the patient, i.e., long-term engraftment due to the self-renewal capability of $T_{SCM}$ cells. Therefore, in one embodiment, the introduction of $T_{SCM}$ cells to the patient can be done just once or a few times, e.g., 1-5 times. Also, in some embodiments, the administered (or introduced) $T_{SCM}$ cells are removed from the subject after the cancer is substantially treated. In some embodiments, the removal of the treated $T_{SCM}$ cells is done using a suicide switch in engineered T cells. This removal may be beneficial to do once the patient had been declared (substantially) cancer-free to re-grow a cell type eliminated by the engineered T cells administered to the patient (e.g., B cells in case of treatment with a CD19 CAR T cell).

In some embodiments, a therapeutically effective amount therefore refers to an amount of therapeutic cells or a composition having therapeutic cells that is sufficient to promote a particular effect when administered to a typical subject, such as one who has or is at risk for cancer. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

For use in the various embodiments described herein, an effective amount of therapeutic cells, e.g., $T_{SCM}$ cells, per kilogram (kg) of body weight of the patient is at least or about $10^3$ to $10^8$ cells/kg of body weight of the patient. In some embodiments, the effective amount of therapeutic cells is at least or about $5\times10^2$ cells/kg, $1\times10^3$ cells/kg, $5\times10^3$ cells/kg, $1\times10^4$ cells/kg, $5\times10^4$ cells/kg, $1\times10^5$ cells/kg, $2\times10^5$ cells/kg, $3\times10^5$ cells/kg, $4\times10^5$ cells/kg, $5\times10^5$ cells/kg, $6\times10^5$ cells/kg, $7\times10^5$ cells/kg, $8\times10^5$ cells/kg, $9\times10^5$ cells/kg, $1\times10^6$ cells/kg, $2\times10^6$ cells/kg, $3\times10^6$ cells/kg, $4\times10^6$ cells/kg, $5\times10^6$ cells/kg, $6\times10^6$ cells/kg, $7\times10^6$ cells/kg, $8\times10^6$ cells/kg, $9\times10^6$ cells/kg, $1\times10^7$ cells/kg, $5\times10^8$ cells/kg, or any intervening number of cells/kg of the foregoing. In some embodiments, the effective amount of therapeutic cells is at least or about $1-5\times10^6$ cells/kg of body weight of the patient. In some embodiments, the effective amount of therapeutic cells is at least or about $1-5\times10^7$ cells/kg of body weight of the patient. The therapeutic cells can be derived from one or more donors, or are obtained from an autologous source. In some embodiments described herein, the therapeutic cells are expanded in culture prior to administration to a subject in need thereof.

The efficacy of a treatment having a composition for the treatment of cancer can be determined by the skilled clinician. However, a treatment is considered effective treatment if any one or all of the signs or symptoms of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Cells

Peripheral blood mononuclear cells (PBMCs) were isolated from Trima Accel leukocyte reduction system (LRS) chambers (Terumo BCT, Lakewood, CO) of de-identified healthy blood donors (Stanford Blood Center, Palo Alto, CA) using Ficoll-Paque Plus (GE Healthcare, Chicago, IL, USA) density gradient centrifugation according to manufacturer's instructions. For long-term storage, PBMCs were resuspended in FBS with 10% DMSO and stored in liquid nitrogen at density $1-5\times10^7$ cells/mL. Cryopreserved PBMCs were thawed into cell culture medium (CCM; RPMI 1640 containing 10% FBS, 1× L-glutamine, and 1× penicillin/streptomycin; Thermo Fisher Scientific Waltham, MA, USA) supplemented with 25 U/mL benzonase (SIGMA-ALDRICH®, St. Louis, MO, USA). Cells were then pelleted for 5 minutes at 250×g, resuspended in 10 mL CCM, rested at 37° C., 5% $CO_2$ for 60 minutes, filtered through a 40 μm strainer, and counted. Where indicated, naïve T cells were enriched using Naïve Pan T Cell Isolation Kit (Miltenyi Biotec #130-097-095, Bergisch Gladbach, Germany) according to manufacturer's instructions.

Example 2: CFSE Labeling

Unless otherwise noted, carboxyfluorescein succinimidyl ester (CFSE) labeling was performed as described by Quah and Parish16, 17. Briefly, 50 μg carboxyfluorescein diacetate succinimidyl ester (CFDA-SE) was reconstituted in 18 μL DMSO (CellTrace CFSE Cell Proliferation Kit, Thermo Fisher Scientific #C34554) to create a 5 mM stock immediately prior to labeling. Cells were resuspended in 1 mL warm CCM and transferred into a new 15 mL Falcon tube lying horizontally. A drop containing 110 μL warm PBS was placed on a side of the tube, and 17.6 μL of 5 mM CFDA-SE was diluted into the drop. The tube was then quickly capped and turned upside right while being vortexed gently, yielding a final concentration of 80 μM CFDA-SE. Cells were incubated for 5 minutes at room temperature, quenched by adding 9 mL warm CCM, and washed twice with 10 mL warm CCM. When only naïve T cells were labeled with CFSE, they were combined with the CFSE-negative PBMC fraction devoid of naïve T cells after labeling to restore original cell proportions. All centrifuging steps for live cells were done for 5 minutes at 250 g, 37° C. CFSE and labeled cells were protected from light throughout the experiment. During protocol optimization, the above labeling protocol for $0.1-10\times10^7$ cells and CFSE concentrations in range of 0.2 µM to 320 µM was tested. Long-term cell viability and proliferation were assessed. Manufacturer's labeling protocol for CFSE concentrations 0.2 µM to 20 µM, as well as other CFSE suppliers (BIOLEGEND® #422701, San Diego, CA, USA) were also tested.

Example 3: Expansion and Treatment of Primary Human T Cells

T cells were induced to proliferate using the rapid expansion protocol (REP) for adoptive transfer therapies. Briefly, ~40×10$^6$ cells were plated into a well of a 24-well plate with 2 mL CCM and 600 ng anti-CD3epsilon antibody (clone OKT3, BIOLEGEND® #317304). Where indicated, cells were pre-treated with vehicle (DMSO), ibrutinib (PCI-32765; Cellagen Technology #C7327, San Diego, CA, USA; 700 ng/mL or 1.59 µM), or rapamycin, Cell Signaling Technology #9904S, Danvers, MA, USA, 50 ng/mL or 54.70 nM) for 30 minutes. Starting at 48 hours post-activation, cells were maintained at ~2×10$^6$ cells/mL in CCM containing 300 ng/mL anti-CD3epsilon antibody and 50 U/mL (5 ng/mL) recombinant human IL-2 (PeproTech #200-02, Rocky Hill, NJ, USA) and relevant concentrations of chemical inhibitors (ibrutinib: 700 ng/mL or 1.59 µM on days 0-3, and physiological concentrations of 140 ng/mL or 318 nM on days 3-7; rapamycin: 50 ng/mL or 54.70 nM on days 0-3, and physiological concentrations of 10 ng/mL or 10.94 nM on days 3-7). Where indicated, ibrutinib was only added on either days 0-3 or days 3-7, with vehicle on the remaining days. In initial experiments, a lower concentration of ibrutinib (140 ng/mL on days 0-7; skewing effect was reduced; data not shown) was tested and a higher concentration of ibrutinib (7 µg/mL on days 0-3, 1.4 µg/mL on days 3-7; it is observed cell death and no proliferation; data not shown) was also tested prior to selecting the above ibrutinib treatment regimen. Samples containing 30% of cells from each condition were collected on day 3, 4, 5, and 7, then fixed and stored at -80° C. for analyses by flow cytometry and mass cytometry.

Analysis of $T_{SCM}$-Like and Increased Dysfunction Subsets

To compare the abilities of putative $T_{SCM}$-like and dysfunctional cells to proliferate, persist, and maintain beneficial phenotype, naïve CFSE+ T cells were cultured using REP for 7 days to form these subsets. Based on the observed pattern of protein expression by day 7, FACS staining panel and gating strategy were defined (FIG. 11B). Fc receptors were blocked using Human TruStain FcX™ (BIOLEGEND® #422302) following manufacturer's instructions. Surface antibody staining was performed with anti-CD3ε-V500 (clone UCHT1, BD BIOSCIENCES #561416, Franklin Lakes, NJ, USA), anti-CD8α-PerCP (clone SKI, BD BIOSCIENCES #347314), anti-CD27-PE-Cy7 (clone 0323, BIOLEGEND® #302837), anti-CD45RA-AlexaFluor700 (clone HI100, BIOLEGEND® #304119), and anti-CD279-PE (PD1; clone EH12.2H7, BIOLEGEND® #329905) antibodies for 30 minutes on ice in FACS buffer (PBS with 2% human serum and 2 mM EDTA). Cells were then washed once with FACS buffer and stained with 7-AAD (BIOLEGEND® #420404) to exclude dead cells following manufacturer's instructions. Next, cells were resuspended in FACS buffer to sort out putative $T^{SCM}$ and dysfunctional subsets on FACS Aria II (BD BIOSCIENCES). The post-sort purity of each subset was >90%.

Figure 11A:
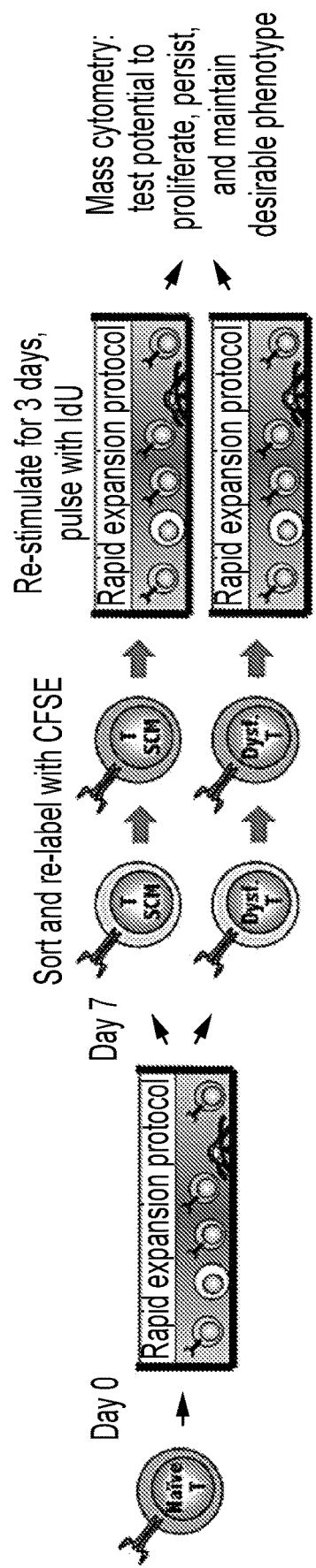

To assess the functional properties of the putative $T_{SCM}$-like and dysfunctional subsets, the sorted cells were relabeled with CFSE and cultured with new autologous CFSE-negative accessory cells using REP for 3 days (FIG. 11A).

To quantify the percentage of cells in S phase, the culture medium was supplemented with 100 µM 5-iodo-2'-deoxyuridine (IdU; SIGMA-ALDRICH® #I7125-5G) 30 minutes prior to sample collection.

Cellular Cytokine Production

To assess intracellular production of IL-2, IFN-γ, and TNF-α at the indicated collection time points, cells were resuspended cells 10$^6$ per mL and stimulated with 50 ng/mL phorbol 12-myristate 13-acetate (PMA; SIGMA-ALDRICH® #P8139, dissolved in ethanol) and 500 ng/mL ionomycin (SIGMA-ALDRICH® #10634, dissolved in ethanol) in presence of 1× Brefeldin A (BIOLEGEND® #420601) for 4 hours. Cells were stained using an antibody panel in Table 5 and assessed by mass cytometry.

Example 4: Mass Cytometry

Samples were processed as previously known in the art. To stain cells for viability, cisplatin (SIGMA-ALDRICH® #P4394) was reconstituted to 100 mM in DMSO and incubated at 37° C. for 3 days to prepare a stock solution, which was then stored in aliquots at -20° C. Cell pellets were resuspended in 1 mL PBS containing 0.5 µM cisplatin, gently vortexed, incubated 5 minutes at room temperature, quenched with 3 mL CCM, pelleted, and resuspended in 1 mL CCM. Cells were fixed by adding 16% paraformaldehyde (PFA; Electron Microscopy Sciences, Hatfield, PA, USA) to a final concentration of 1.6%, gently vortexed, incubated 10 minutes at room temperature, and washed twice with cell staining media (CSM; PBS with 0.5% BSA, 0.02% sodium azide) to remove residual PFA. All centrifuging steps for fixed cells were done for 5 minutes at 600×g, 4° C. Cell pellets were optionally stored at -80° C.

With the exception of titrations, samples were palladium-barcoded and pooled as known in the art to improve staining consistency. Fc receptor blocking was performed with Human TruStain FcX™ (BIOLEGEND® #422302) following manufacturer's instructions to prevent non-specific antibody binding. Antibodies against surface antigens were pooled into a master mix in CSM yielding 50 µL (350 µL if barcoded) final reaction volumes per sample, and filtered through a 0.1 µm filter (Millipore #UFC30VV00, Billerica, MA, USA) for 5 minutes at 1,000×g to remove antibody aggregates. Antibody master mix was then added to each sample, resuspended, and cells were incubated 30 minutes at room temperature. Mass cytometry antibody panels are listed in Tables 1, 2, and 4. With the exception of antibodies purchased from Fluidigm (South San Francisco, CA, USA), all mass cytometry antibodies that were conjugated to reporter metal isotopes in-house were titrated to determine optimal staining concentrations prior to incorporating that antibody into a staining panel. Antibodies were conjugated using MaxPar Antibody Conjugation Kit (Fluidigm) and titrated on cells both positive and negative for the target antigen expression to identify concentration yielding the best signal-to-noise ratio. Following the surface stain, cells were washed with CSM, permeabilized with 4° C. methanol for 10 minutes on ice, washed twice with CSM, stained with an antibody master mix (prepared as above) against intracellular antigens in 50 µL (350 µL if barcoded) CSM for 30 minutes at room temperature, and washed once with CSM. To stain DNA, cells were incubated in PBS containing 1:5000191 Ir/193 Ir MaxPar Nucleic Acid Intercalator (Fluidigm) and 1.6% PFA for 1-3 days at 4° C. Just prior to analysis, cells were washed once with CSM and twice with filtered double distilled water, resuspended in normalization beads (EQ Beads, Fluidigm), filtered, and placed on ice.

During event acquisition, cells were kept on ice and introduced into the CyTOF 2 (Fluidigm) using Super Sampler (Victorian Airship and Scientific Apparatus, Alamo, CA, USA). In addition to reporter metal isotopes listed in antibody panels (Tables 1, 2, and 4), event length and channels $^{102}$Pd, $^{104}$Pd, $^{105}$Pd, 106Pd, $^{108}$Pd, and $^{110}$Pd (barcoding); 140Ce, $^{151}$Eu, $^{153}$Eu, $^{165}$Ho, and $^{175}$Lu (bead normalization); $^{191}$Ir and $^{193}$Ir (DNA); and $^{195}$Pt and $^{196}$Pt (dead cells); and $^{138}$Ba (to help define single cells) were recorded. In experiments quantifying IdU incorporation, recorded $^{127}$I was also recorded.

In optimization experiments for CFSE detection, also tested were alternative permeabilization methods (no permeabilization, 0.2% saponin, CFSE staining after permeabilization), multiple anti-FITC antibody clones, concentrations, and detection channels (clone FIT-22 conjugated to $^{172}$Yb, 0.25-16 µg/mL, BIOLEGEND® #408302; pre-conjugated clone FIT-22 on 144Nd, 0.5-8 tests, Fluidigm #3144006B; clone F4/1 conjugated to $^{172}$Yb, 0.25-16 µg/mL, Abcam #ab112511, Cambridge, UK; polyclonal antibody conjugated to $^{172}$Yb, 1-64 µg/mL, Southern Biotech #6400-01, Birmingham, AL), and extended anti-FITC incubation time (60 instead of 30 minutes) for all clones.

Single Cell RNA-Sequencing of T-Cell Division States

Figure 9A:
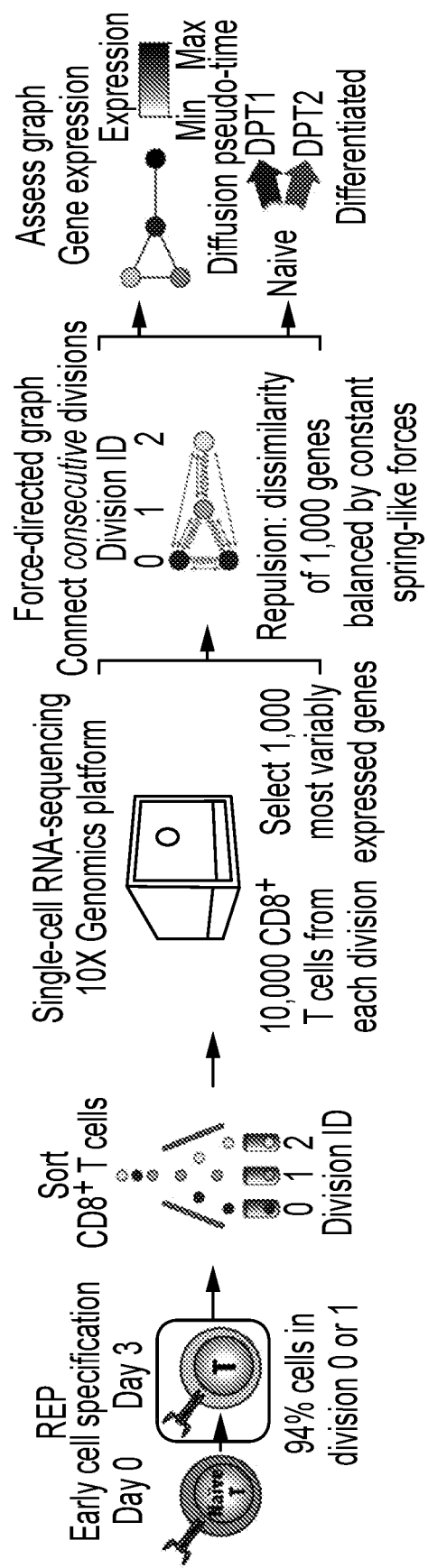
Figure 9B:
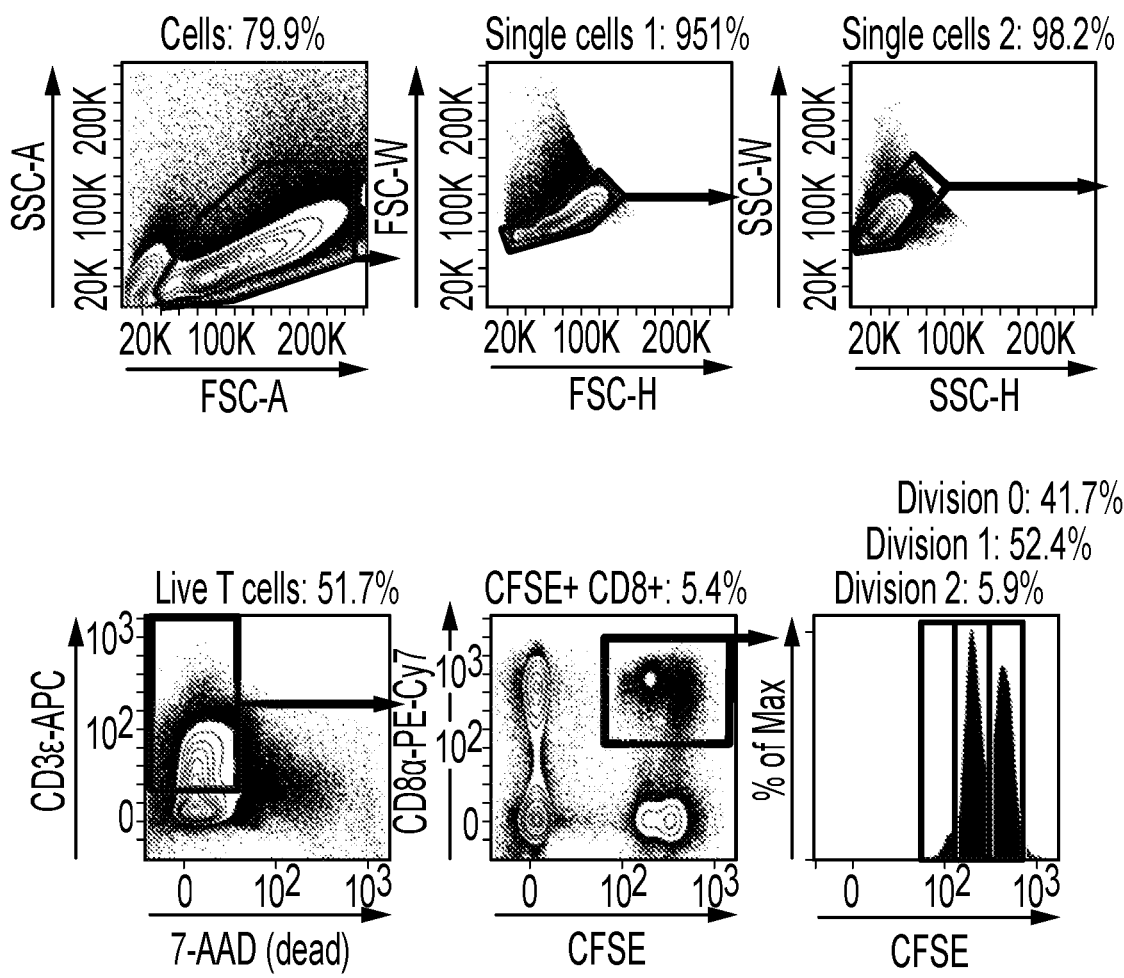

Cells were collected as described on day 3 of REP (FIG. 9B). The lot of PBMCs was previously analyzed in order to obtain the exact timing to observe all 3 division states in the same culture. Here, ~10,000 live CFSE+ CD8+ T cells were prospectively isolated from division 0, 1, or 2 and resuspended in 100 µL CCM. Cells were stored on ice and processed the same day on the Chromium platform (10× Genomics, Pleasanton, CA, USA) at the Stanford Functional Genomics Facility for droplet-based 3' single-cell RNA-sequencing per the manufacturer's instructions, with a target of 3,000 cells per sample and a sequencing depth of >50,000 reads per cell. The sample libraries were combined and ran on a single lane of the HiSeq 4000 platform (Illumina, San Diego, CA, USA).

Example 5: Flow Cytometry

When comparing mass cytometry and flow cytometry data, viability staining was also performed with Fixable Violet Dead Cell Stain (Thermo Fisher Scientific #L34955). Samples were then fixed as described above and separated into two parts for both flow and mass cytometry analysis just prior to storage at −80° C. Surface staining was performed with anti-CD3epsilon-APC (clone UCHT1, #300412, BIOLEGEND®) and anti-CD8a-APC-H7 (clone SK1, BD BIOSCIENCES #560273, Franklin Lakes, NJ, USA) antibodies. Cells were then resuspended in 250 µL CSM and analyzed on LSRII flow cytometer (BD BIOSCIENCES).

Data Processing

Mass cytometry data were normalized and debarcoded. Data were transformed using inverse hyperbolic sine (arsinh) with a cofactor of 5 for DNA or protein expression, or with a cofactor of 20 for CFSE. Single cells were gated using Cytobank software (www.cytobank.org) based on event length and 191Ir/193Ir (DNA) content as described by Bendall et al. Live non-apoptotic cells were gated based on 195Pt (viability) content and cleaved PARP (cPARP). Hematopoietic cells were selected based on CD45 expression. In initial experiments (antibody panel from Table 1), CD45+ cells were further gated to select CD8+ T cells (CD3ε+CD4− CD8α+ CD14− CD19− CD20−), myeloid dendritic cells (mDCs; CD38− CD11c+CD14− CD19− CD20− HLA-DR+), or monocytes (CD38− CD14+CD19− CD20−). In experiments focused on differentiation of CD8+ T cells (antibody panels from Tables 2-5), also excluded were events: CD33+ (myeloid), CD61+ (platelets), CD235+ (erythrocytes), or TCRγδ+ (γδ T cells). Where indicated, CFSE+ cells were selected based on a CFSE− control from the same day. Flow cytometry data were transformed using arsinh with a cofactor of 150. CD8+ T cells were gated as single live CD3ε+CD8α+ events.

Single-cell RNA-sequencing reads were aligned to the Genome Reference Consortium Human Build 38 (GRCh38), normalized for batch effects, and filtered for cell events using the Cell Ranger software (10× Genomics). A total of 4,060 cells were sequenced to an average of 52,040 post-normalization reads per cell capturing a median of 18,770 unique molecular identifier (UMI) counts per cell mapping to 3,544 unique genes per cell. The cell-gene matrix was further processed using the Cell Ranger R Kit software (10× Genomics) as described by Zheng et al. Briefly, genes with ≥1 UMI counts in any given cell were selected (19,222 genes). UMI counts were then normalized to UMI sums for each cell and multiplied by a median UMI count across cells. Next, the data were transformed by taking a natural logarithm of the resulting data matrix. Where indicated, 1,000 most variably expressed genes were selected based on normalized dispersion.

Division ID Assignment

Figure 2A:
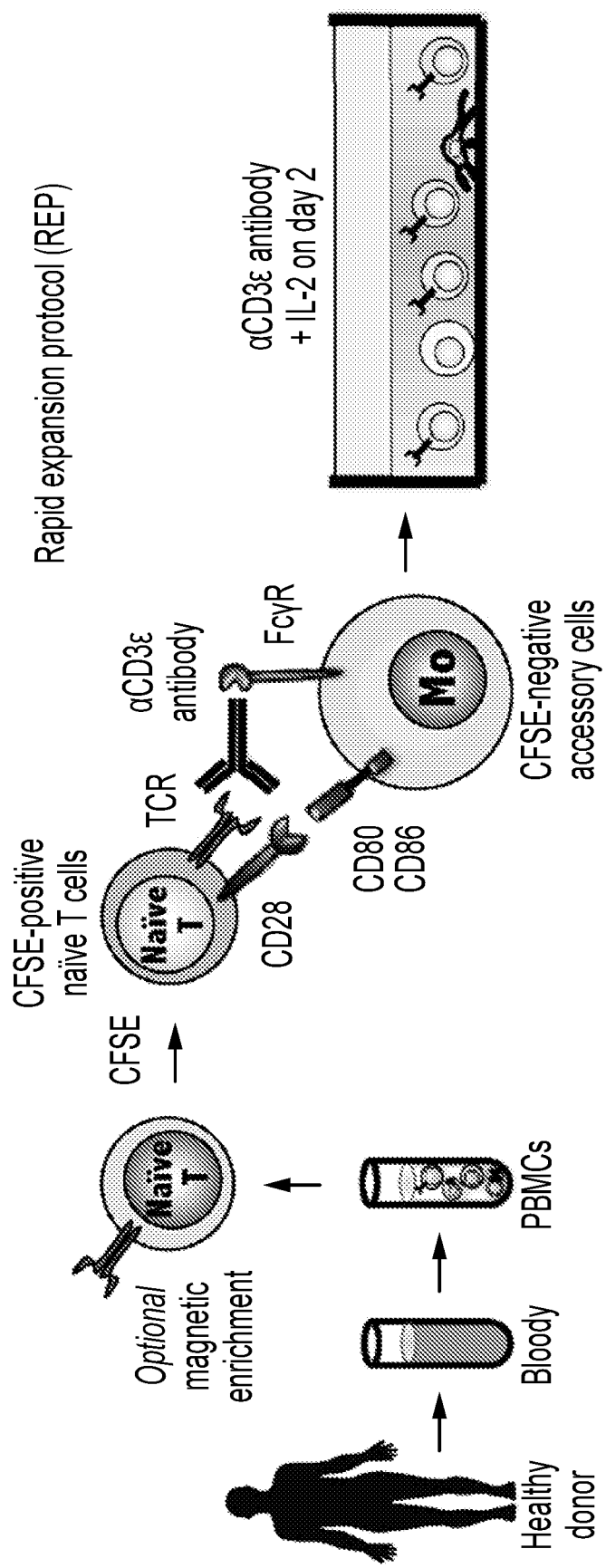
Figures 1, 2B:
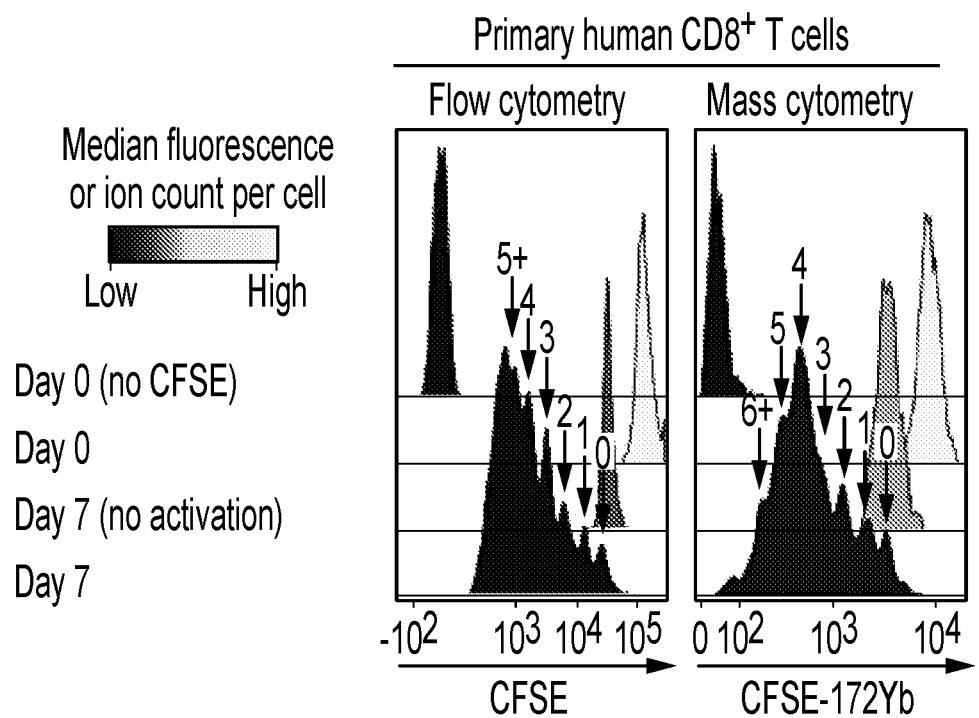

Single-cell data for CFSE+ CD8+ T cells were processed using R (www.r-project.org) and Bioconductor (www.bioconductor.org) software. To assign division IDs to cells in a given sample, division peaks in log 2-transformed CFSE ion count or fluorescence data were identified using local regression. Centroid of division 0 peak and peak s.d. were estimated based on non-proliferating control cells collected at the same time. Remaining division IDs were assigned to all cells where assignment confidence was ≥80% based on normal distribution modeling (or division −1 if not assigned). Top and bottom CFSE intensity cutoffs were set at 2× s.d. above division 0 and 2× s.d. below the maximum division, respectively. A modified FCS file with "Division" column appended to original data was then exported for downstream analysis. FIG. 2B shows a summary of the division ID assignment process.

Forced-Directed Layout

To create force-directed graphs, Vortex software that implements ForceAtlas engine was used. Here, Vortex was extended to only allowing edge connections either between subsequent time points (as in the FLOW-MAP algorithm), or between subsequent divisions. Data were sampled as indicated prior to graph construction. Cell dissimilarity, a basis for repulsive forces, was calculated based on angular (cosine) distance in indicated dimensions. Edges, a basis for spring-like attractive forces, connected each cell to its 10 nearest neighbors in the original high-dimensional space, which also had to be within consecutive (−1, 0, +1) division states. See FIGS. 4A and 5A for a summary of this process.

Diffusion Maps

Diffusion maps embed single-cell data into diffusion components through a non-linear transformation. To perform the embedding, a matrix of diffusion distances is computed among all cells using mathematics of heat diffusion and random walk Markov chains. This matrix is then applied to calculate DPT, a metric based on the transition probability of a diffusion process. To embed data into diffusion components and to calculate DPT, destiny implementation of diffusion maps in R was applied, which enables identification of up to two endpoints of a differentiation process. Diffusion maps were constructed using angular distance metric and the same markers as in force-directed graphs. Diffusion components, DPT values, division IDs, and time (days) were appended to the data, enabling visualization of these parameters in force-directed graphs using Vortex. Where indicated, DPT values for different treatment conditions were normalized to 0-1 range for visualization purposes.

Statistical Analysis

Statistical analysis was performed using R statistical software (www.r-project.org). To assess CFSE correlation between identical samples analyzed by flow and mass cytometry, Spearman's rank correlation coefficient was calculated using log 10-transformed medians for each division ID, or using the percentage of cells assigned the same division ID. When no comparison to flow cytometry was made, Spearman's rank correlation coefficient was calculated using arsinh-transformed mass cytometry data. In each case, P-values were calculated using correlation test. Normality assumption using Shapiro-Wilk test was tested. As the normality assumption was not met in statistical tests on single-cell data performed here, unpaired two-tailed Wilcoxon Mann-Whitney U test was applied to assess statistical significance between two groups. When more than two groups were compared, Kruskal-Wallis H test (one-way analysis of variance on ranks) was first used to check whether there are differences among treatment groups, followed by unpaired two-tailed Wilcoxon-Mann Whitney test applied to each treatment pair, and Bonferroni correction to correct for multiple hypothesis testing. To assess evidence for a decrease in mean phenotypic diversity with division across experiments, lme4 implementation of linear mixed-effects models in R was used.

Lasso was tested to identify markers associated with DPT. 80% of cells into training set and 20% of cells were allocated into test set using random sampling. To construct a lasso model, glmnet implementation of lasso in R was used, including a built-in cross-validation function to tune the L1 regularization parameter lambda. All training data was then used to construct the final model, and applied that model to the test data to assess performance.

Data Availability and Code Availability

Single-cell data can be accessed on GitHub (github.com/BendallLab/division-history). Singe-cell RNA-sequencing data are also available on Gene Expression Omnibus (www.ncbi.nlm.nih.gov/geo; GEO accession: GSE119139; reviewer's access token: ctqxwsmetpwblmb). Code availability: An extended version of the Java-based Vortex software and documentation can be accessed at github.com/nolanlab/vortex.

Example 6: Detection of Carboxyfluorescein Succinimidyl Ester (CFSE) by Mass Cytometry Using Affinity-Based Reagents Fluorescent dye dilution assays have proven useful in estimating the number of cell divisions by flow cytometry. However, fluorescence cannot be detected by mass cytometry. To overcome this limitation, a mass cytometry assay was developed to track cell proliferative history. Specifically, Applicant leveraged the structural similarity between carboxyfluorescein succinimidyl ester (CFSE), a fluorescent component of a well-established CFSE dilution assay, and fluorescein isothiocyanate (FITC), a fluorophore for which antibodies are commercially available, to track changes in CFSE signal via an anti-FITC antibody conjugated to a reporter metal isotope (FIG. 1A). As cells go through mitosis, they pass ~50% of CFSE to each daughter cell, providing a proxy for the number of times each cell has divided in a given sample.

These results in this experiment showed that homogeneous cell labeling and reduced long-term toxicity are achieved in primary human CD8$^+$ T cells with 80 µM CFSE in the presence of serum, as compared to conventional labeling protocols (data not shown).

Figures 1B, 1C:
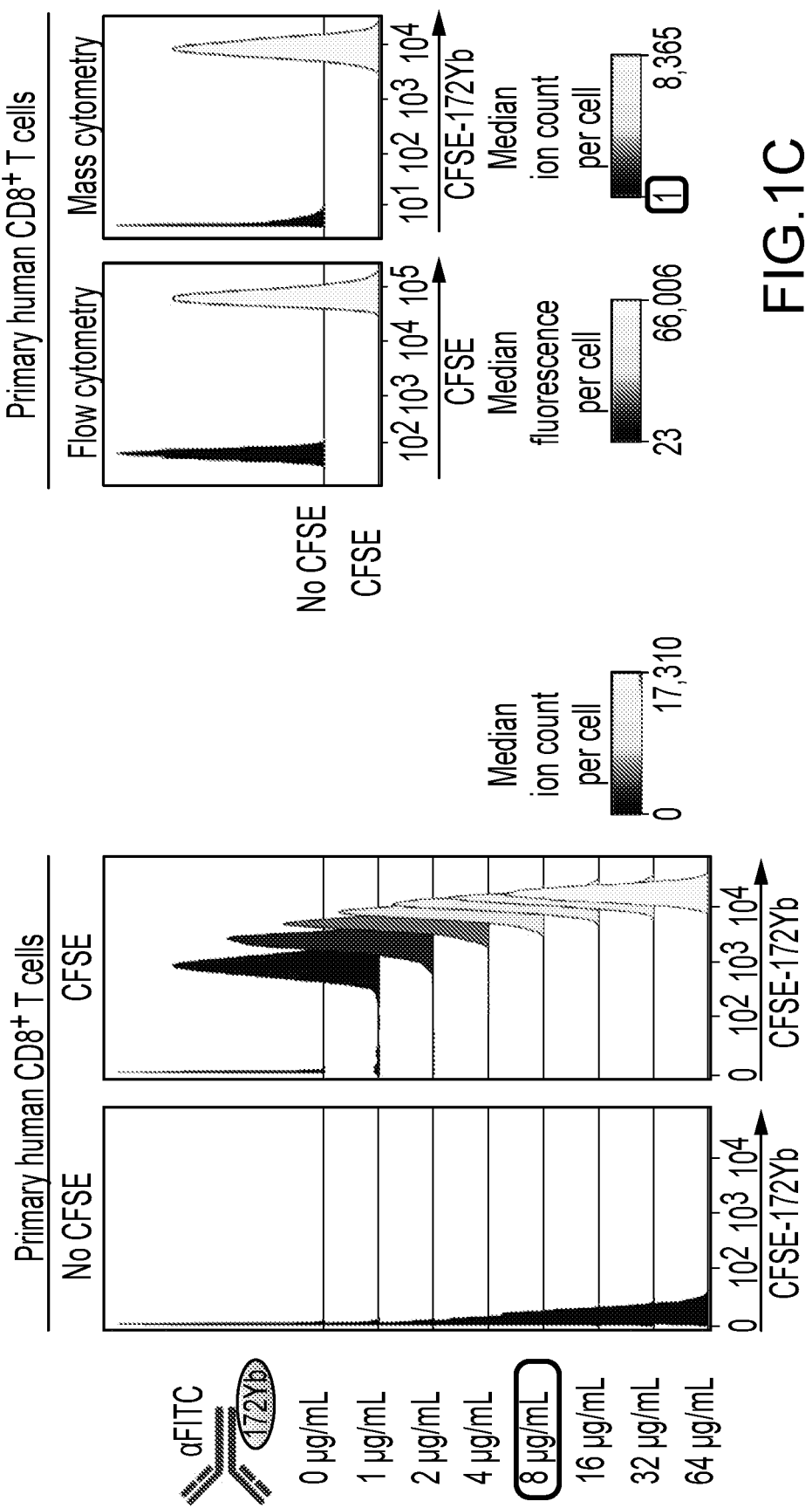
FIG. 1B: A concentration gradient of a polyclonal anti-FITC antibody conjugated to the $^{172}$Yb reporter metal isotope was used to detect CFSE by mass cytometry.
FIG. 1C: Equivalent CFSE signal was obtained from a sample labeled as in FIG. 1A and analyzed in parallel either by flow cytometry or mass cytometry.

Next, the optimal CFSE detection conditions were established for mass cytometry using an antibody panel shown in Table 1. In this experiment, a concentration gradient of a polyclonal anti-FITC antibody conjugated to the $^{172}$Yb reporter metal isotope was used to detect CFSE by mass cytometry (FIG. 1B). Peripheral blood mononuclear cells (PBMCs) from a healthy donor were labeled with CFSE using optimal staining conditions and analyzed by mass cytometry. Based on its saturation profile and signal-to-noise ratio in CD8$^+$ T cells, the ideal anti-FITC-172Yb antibody concentration was identified as 8 µg/mL (red box). It was found that in contrast to two monoclonal anti-FITC antibodies conjugated to a reporter metal isotope, a polyclonal antibody applied following either methanol or saponin permeabilization produces the strongest signal with optimal signal-to-noise ratio (FIG. 1B). The best CFSE signal was achieved following 30 minutes of staining after methanol permeabilization, indicating anti-FITC antibody saturation with standard mass cytometry staining conditions. Only live cells had sufficient enzyme activity to produce an optimal signal.

TABLE 1

Antibody staining panel for mass cytometry CFSE dilution assay development experiments on human PBMCs.

| Antibody target and metal | Company | Catalog number | Clone | Isotype | Conjugation & titration | Final concentration |
|---|---|---|---|---|---|---|
| CD45-115In | Biolegend | 304002 | HI30 | Mouse IgG1 | In-house | 1 jg/mL |
| cPARP-141Pr* | BD Biosciences | 552597 | F21-852 | Mouse IgG1 | In-house | 1 jg/mL |
| CD19-142Nd | BD Biosciences | 555410 | HIB19 | Mouse IgG1 | In-house | 1 jg/mL |
| CD4-145Nd | Fluidigm | 3145001B | RPA-T4 | Mouse IgG1 | Fluidigm | 1 Test |
| CD8a-146Nd | Fluidigm | 3146001B | RPA-T8 | Mouse IgG1 | Fluidigm | 1 Test |
| CD16-148Nd | Fluidigm | 3148004B | 3G8 | Mouse IgG1 | Fluidigm | 1 Test |
| CD11c-159Tb | Fluidigm | 3159001B | Bu15 | Mouse IgG1 | Fluidigm | 1 Test |
| CD14-160Gd | Fluidigm | 3160001B | M5E2 | Mouse IgG2a | Fluidigm | 1 Test |
| CD20-161Dy | BD Biosciences | 555621 | 2H7 | Mouse IgG2b | In-house | 2 jg/mL |
| CD38-167Er | Biolegend | 303502 | HIT2 | Mouse IgG1 | In-house | 1 jg/mL |
| CD3E-170Er | Biolegend | 317304 | OKT3 | Mouse IgG2a | In-house | 4 jg/mL |

TABLE 1-continued

Antibody staining panel for mass cytometry CFSE dilution assay development experiments on human PBMCs.

| Antibody target and metal | Company | Catalog number | Clone | Isotype | Conjugation & titration | Final concentration |
|---|---|---|---|---|---|---|
| FITC-172Yb* | Southern Biotech | 6400-01 | Polyclonal | Sheep IgG | In-house | 8 jg/mL |
| HLADR-174Yb | Fluidigm | 3174001B | L243 | Mouse IgG2a | Fluidigm** | 0.5 Test | cPARP, cleaved PARP. The data presented in Table 1 relates to those presented in FIGS. 1A-1C.
*These antibodies were used for intracellular staining (post-methanol). Remaining antibodies were used during surface staining (prior to methanol permeabilization).
**Recommended concentration was adjusted based on in-house titration results.

Direct comparison of flow cytometry to mass cytometry showed that these methods yielded an equivalent CFSE signal (FIG. 1C). In this experiment, equivalent CFSE signal was obtained from a sample labeled as in (FIG. 1A) and analyzed in parallel by flow and mass cytometry. Red box indicates the near-zero anti-FITC-172Yb antibody staining background in control cells that were not labeled with CFSE. The antibody was titrated once; results in (FIG. 1C) are representative of 3 experiments. In this comparison, mass cytometry had nearly no background (FIG. 1C, red box), which is typical for mass cytometry measurements. This lack of autofluorescence allowed for detection of an equivalent CFSE signal in other cell types, such as monocytes and dendritic cells.

Overall, leveraging structural similarity between CFSE and FITC, a strong and specific mass cytometry CFSE signal was obtained using commercially available anti-FITC antibodies conjugated to reporter metal isotopes.

Example 7: CFSE Traces Labeled Cells and their Proliferative History in Mass Cytometry Assays Next, the experiments were conducted to test whether the method of detecting CFSE by mass cytometry can resolve divisions among proliferating cells. Since flow cytometry dye dilution assay was originally developed for T cells, and due to the recent successes of ACT in cancer immunotherapy, primary human T lymphocytes were induced to proliferate using a rapid expansion protocol (REP) for ex vivo T-cell expansion in ACT. In REP, T cells were incubated with a soluble anti-CD3epsilon antibody in the presence of Fc receptor-bearing accessory cells, including monocytes. These accessory cells trigger T-cell receptor (TCR) crosslinking and signaling by presenting the anti-CD3epsilon antibody via their Fc receptors. The accessory cells also provide co-stimulation via CD80, CD86, and CD137L molecules that are expressed in this context (FIG. 2A).

Figures 2, 2B:
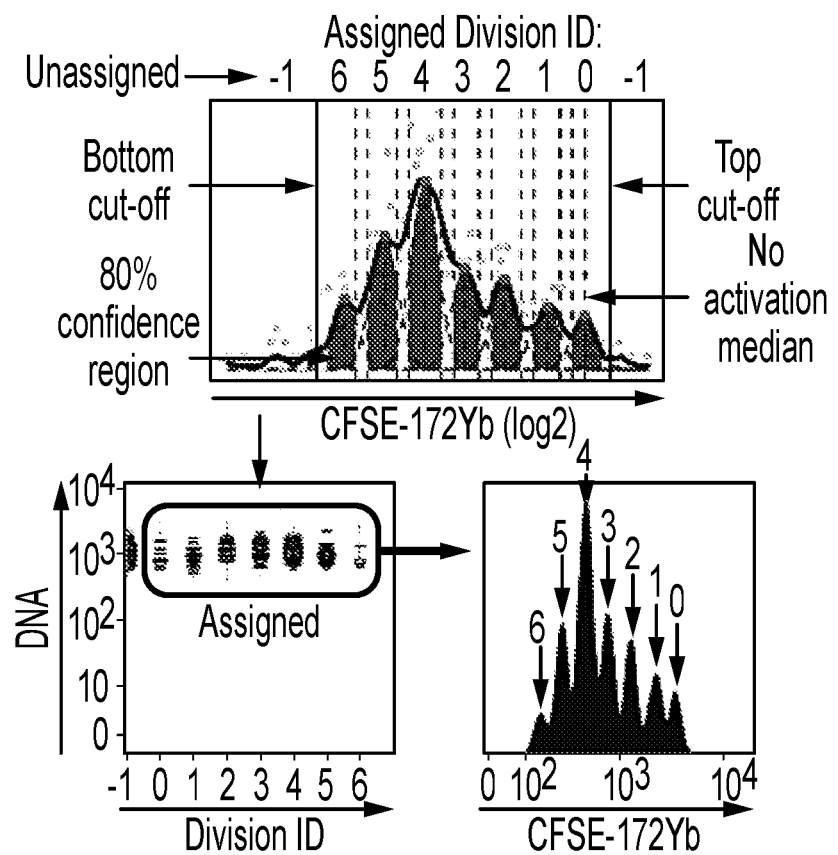
Figure 2D:
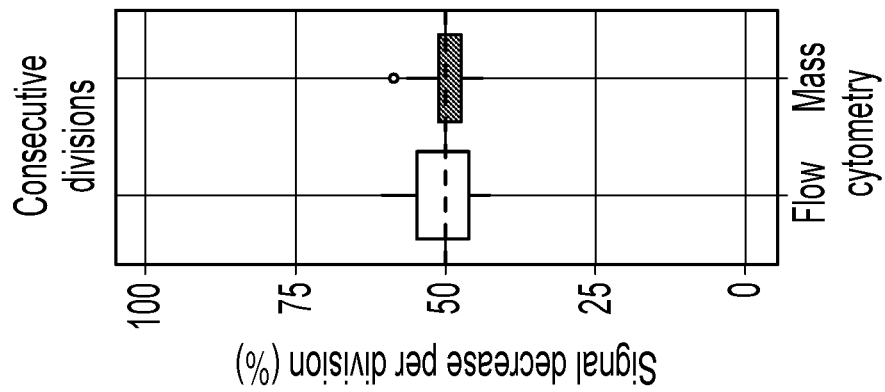
Figure 2C:
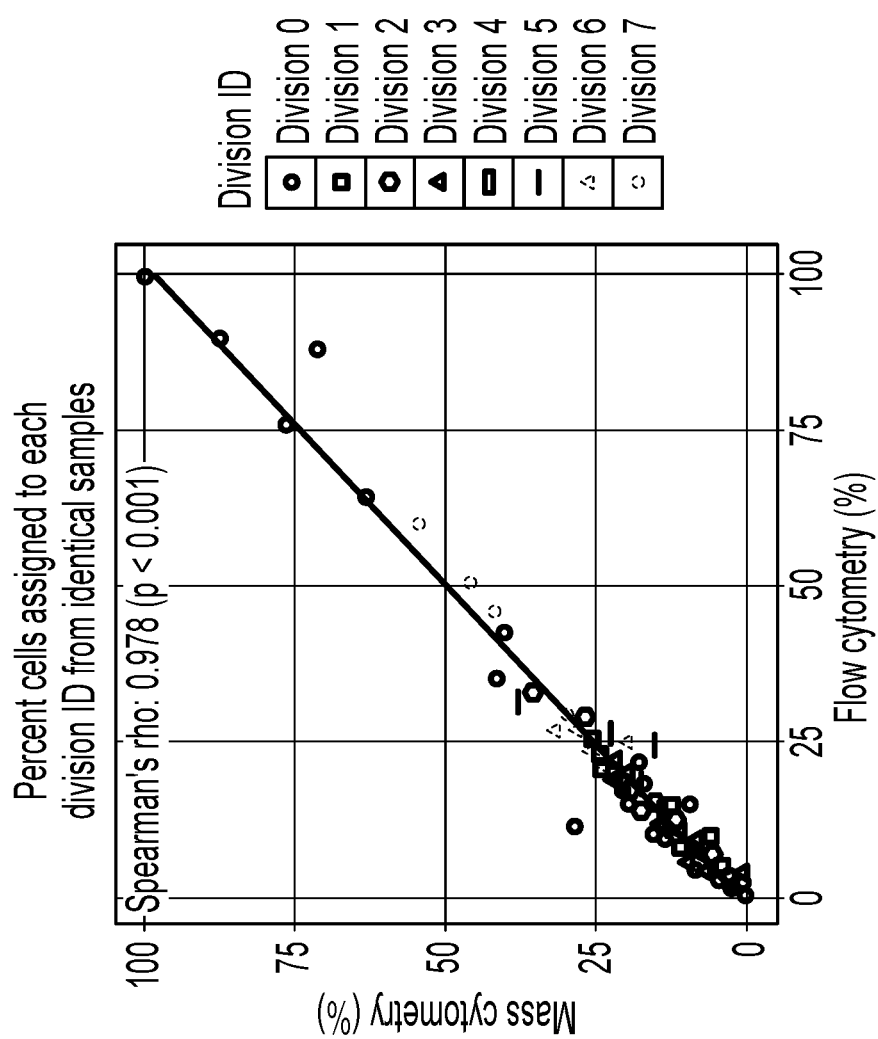
Figure 7A:
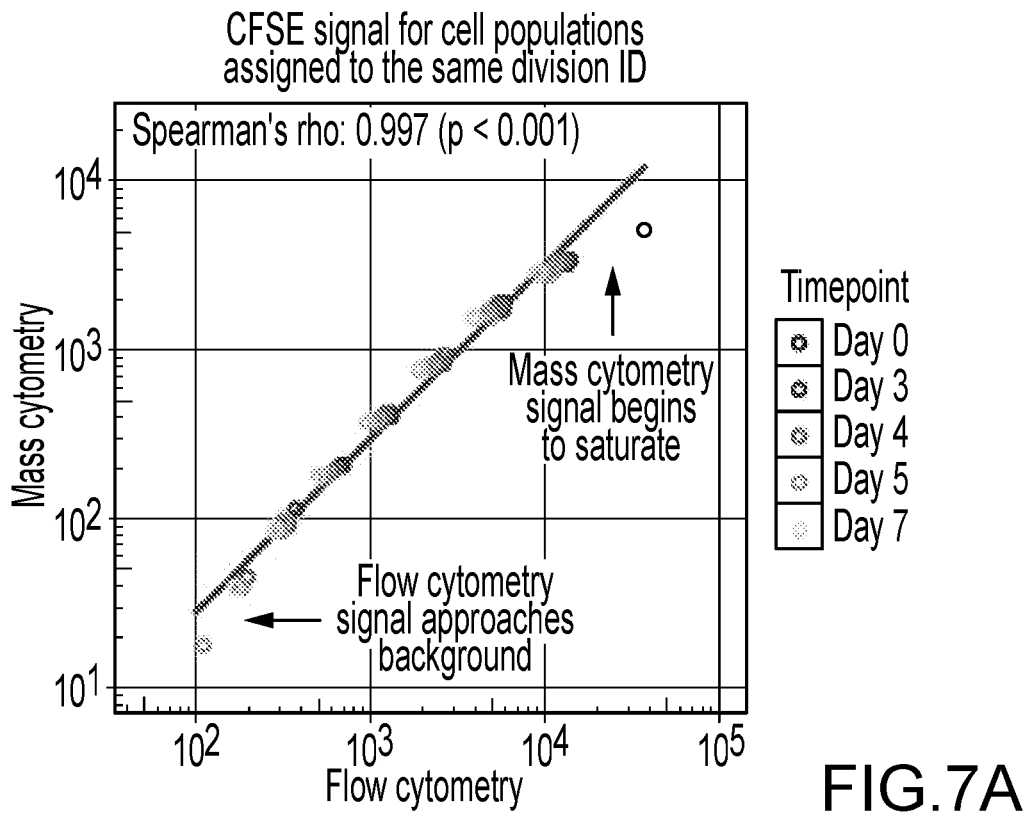
FIGS. 7A-7E. Comparison of cell proliferative history based on flow cytometry and mass cytometry. (A) Spearman correlation analysis comparing CFSE signal (geometric mean) in primary human CD8$^+$ T cells falling into each division ID. Correlation test was applied to $\log_{10}$-transformed values. Samples (n=6) were collected from rapid expansion protocol (REP) cultures on days 0, 3, 4, 5, and 7 and grouped by day. Division IDs were assigned to identical samples based on either flow cytometry or mass cytometry analysis. Day of sample collection is indicated using a color gradient. Arrows indicate observed trends. (B) Flow cytometry and mass cytometry CFSE signal drift in samples from (A) grouped by division ID. Linear regression was applied to CFSE ion counts ($\log_{10}$-transformed geometric mean) in cells falling into the same division ID. Slope is indicated next to each linear regression line. Division ID is indicated using a color gradient. (C) CFSE signal reduction per division was calculated based on geometric means within each sample from (A) at each day of collection. A dashed line indicates the expected 50% reduction. (D) Complete gating strategy for CFSE-negative (before magnetic enrichment) and CFSE-positive (after magnetic enrichment) T cells analyzed by mass cytometry (REP day 0). (E) Gating strategy demonstrating enrichment of naïve phenotype among CFSE-positive vs. CFSE-negative CD8$^+$ T cells from (D). Results in (AE) are from 1 experiment representative of 3 experiments. This Figure relates to the data presented in FIGS. 2A-2F above.
Figure 7B:
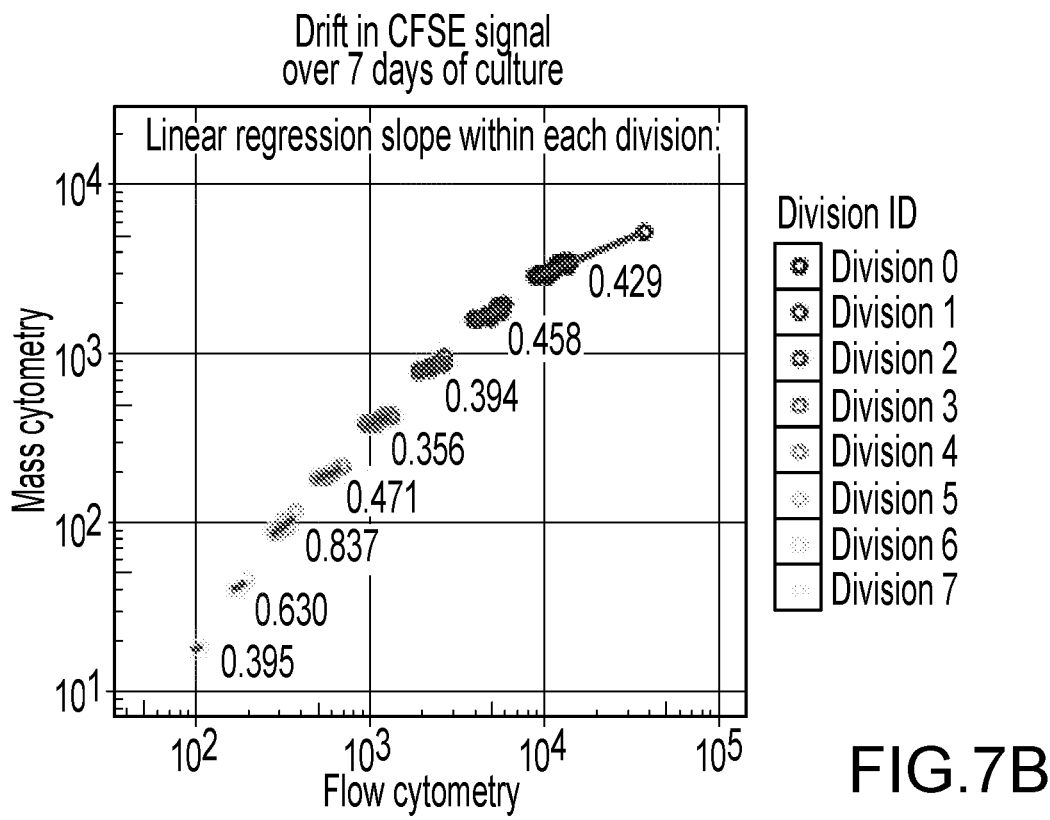
Figure 7C:
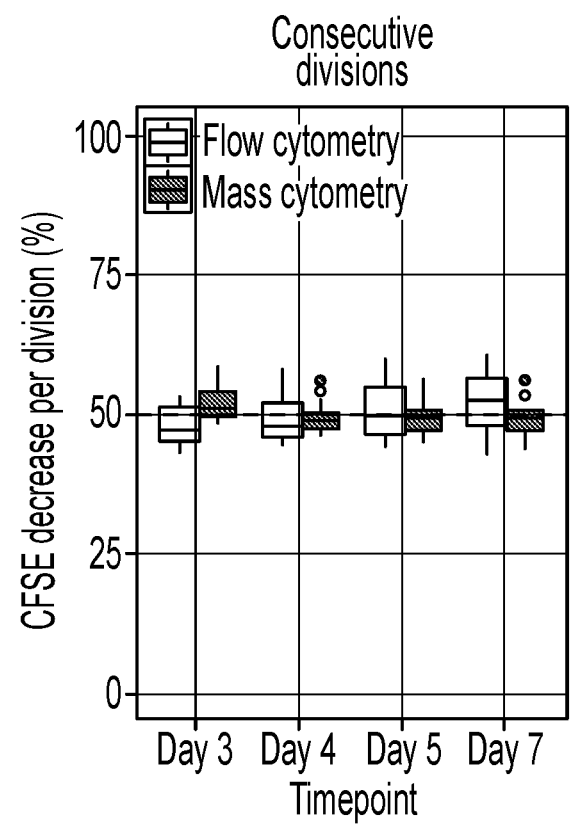

In control experiments the measured CFSE dilution was directly compared by flow cytometry to antibody-based detection by mass cytometry. With both methods, Applicant could distinguish ≥5 cell divisions (FIG. 2B). Using a mathematical model based on local regression, division IDs were assigned to all cells falling into the ≥80% confidence region (FIG. 2B). In doing so, Applicant was able to compare cells within each division in identical samples. It was found that the percentage of cells assigned to each division was nearly identical based on flow and mass cytometry analysis of matched samples (Spearman's rank correlation coefficient: 0.978; FIG. 2C). Correlation in CFSE signal was also high for these samples (Spearman's rank correlation coefficient: 0.997). To estimate signal drift over time (e.g., loss of signal without division), linear regression was applied to cells falling into the same division over multiple days. If the drifts were the same for flow and mass cytometry, one would expect the slope of each regression line to be 1. However, it was observed that such slope was consistently lower than 1 (division IDs 0-7: mean±s.d.=0.496±0.161), suggesting that CFSE signal is fading faster in flow cytometry. This observation is likely due to instability of CFSE fluorescence in living cells, whereas affinity-based reagents could still resolve its chemical structure. As expected, CFSE signal decreased ~50% each time cells divided, and this was true regardless of the cytometry method used (FIG. 2C) or time point assessed (FIG. 7C).

Figure 2E:
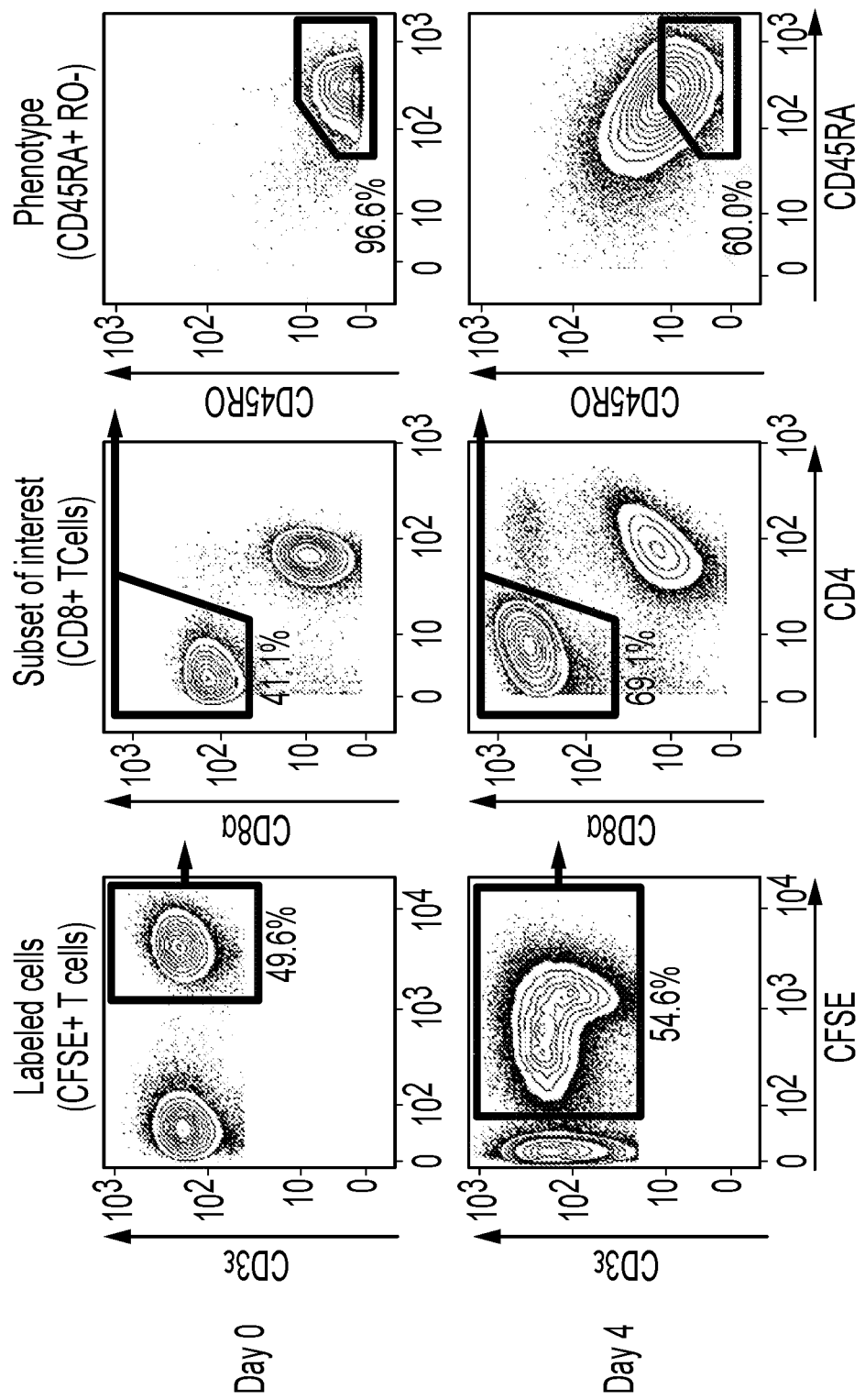
Figure 2F:
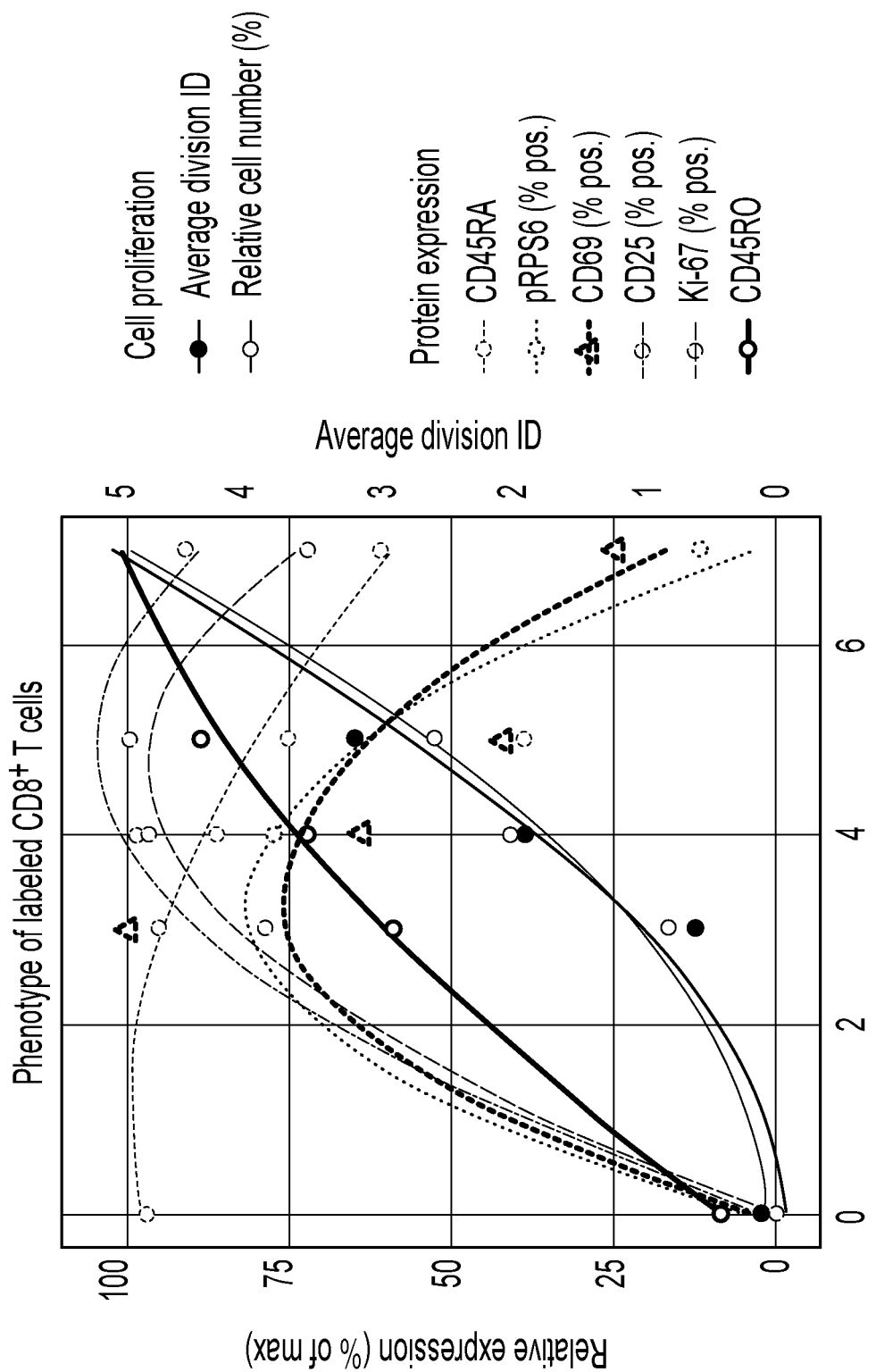
Figure 7D:
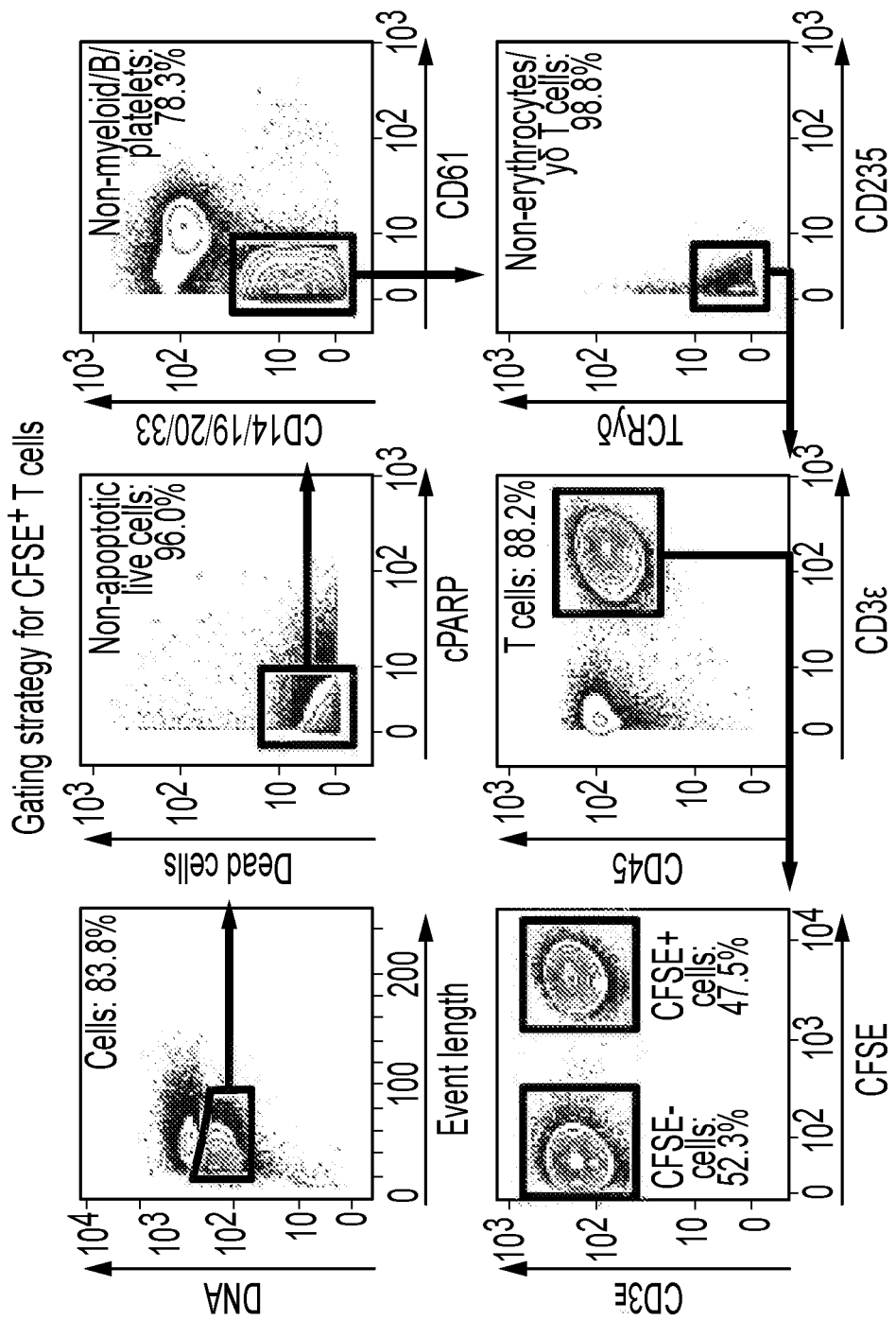
Figure 7E:
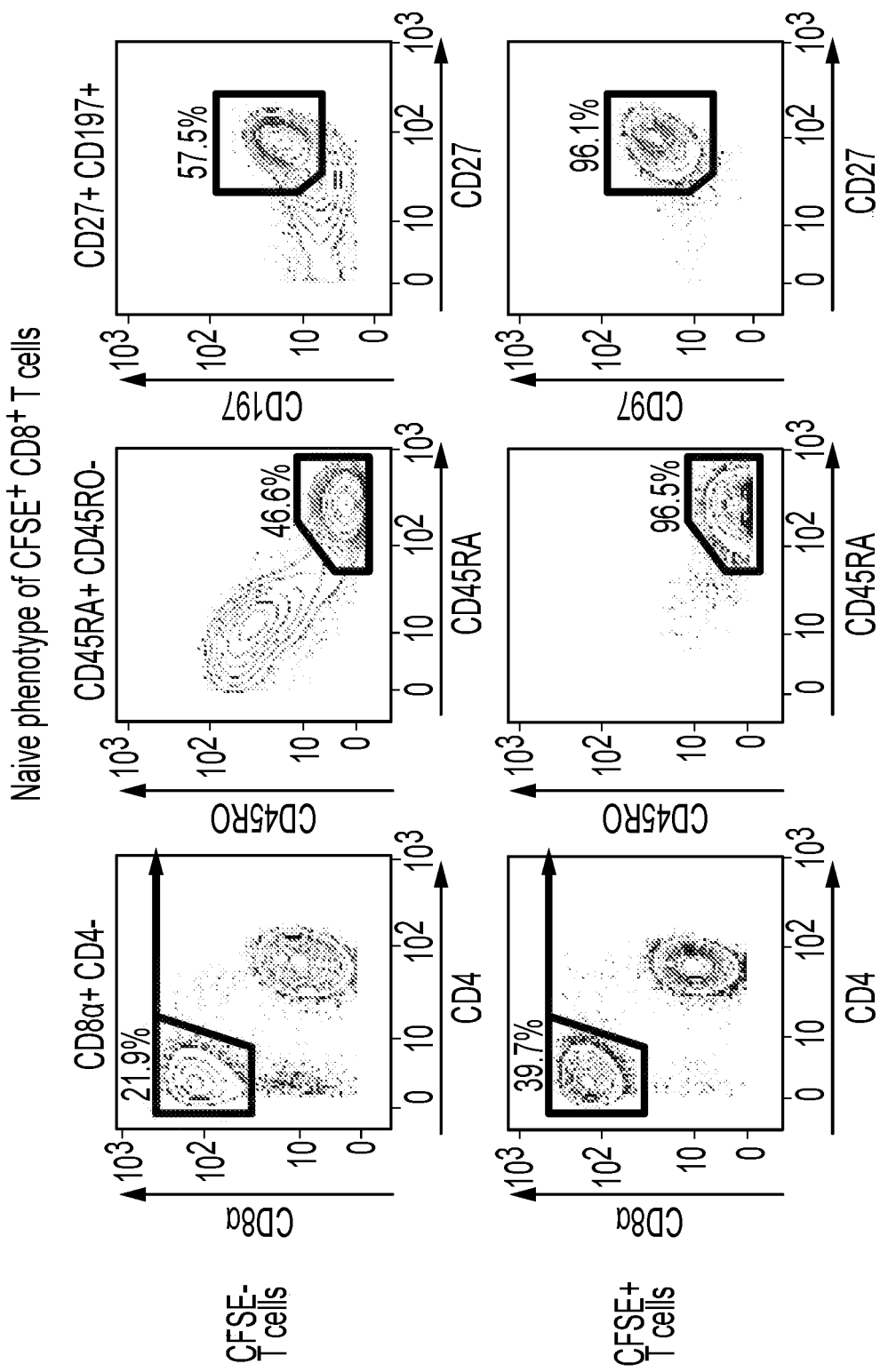

It is often of interest to track fate of a specific cell population without genetic manipulation, especially in primary human samples. Therefore, the experiments were conducted to test lineage-tracing utility of the mass cytometry dye dilution assay by following phenotype of CFSE-positive naïve CD8$^+$ T cells among CFSE-negative accessory cells (FIG. 2E; FIG. 7D for complete gating strategy, and FIG. 7E for comparison of CFSE-positive and CFSE-negative cells after magnetic enrichment of naïve T cells). This analysis could be further tailored by selecting only CD8$^+$ cell subset in silico to track their phenotype, for example by examining protein markers defining naïve T-cell state (FIG. 2E, FIG. 7E). By tracking fate of chemically labeled naïve CD8$^+$T cells in REP cultures over seven days, it was observed expected changes in proliferation and average expression of key T-cell markers (FIG. 2F).

Example 8: Protein Expression is Predominantly Division-Dependent in Early T-Cell Differentiation Because REP is used to expanded T lymphocytes for patients receiving ACT in the clinic, and since cancer immunotherapy is increasingly successful for these patients, the study was focused on a panel of clinically relevant T-cell activating and inhibitory receptors in addition to T-cell fate specification markers (Tables 2-3). Although expression of a few proteins across divisions has previously been analyzed by flow cytometry, a truly high-dimensional analysis to our knowledge has not yet been performed. The reason is that dyes used in fluorescent dye dilution assays are extremely bright. As such, dye spectral overlap with other channels precludes resolving subtle differences in protein expression at each division, especially after several channels had been used to select cells of interest (e.g., viability, CD3epsilon, CD8a). With mass cytometry, division and time-dependent dynamics of 23 markers after was tracked using 13 parameters for stringent selection of CFSE$^+$ CD8$^+$ T cells (DNA, length, viability, apoptotic status, lineage; Table 2, FIGS. 7D-E) and additional parameters to ensure high data quality (e.g., bead normalization, sample barcoding).

TABLE 2

Antibody staining panel for optimized mass cytometry CFSE dilution
assays tracking fate of human naïve CFSE+ CD8+ T cells over REP days 0-7.

| Antibody target and metal | Company | Catalog number | Clone | Isotype | Conjugation & titration | Final concentration |
|---|---|---|---|---|---|---|
| CD235-113In | Biolegend | 306602 | HIR2 | Mouse IgG2b | In-house | 1 pg/mL |
| CD45-115In | Biolegend | 304002 | HI30 | Mouse IgG1 | In-house | 2 pg/mL |
| CD61-139La | Biolegend | 336402 | VI-PL2 | Mouse IgG1 | In-house | 1.5 pg/mL |
| cPARP-141Pr* | BD Biosciences | 552597 | F21-852 | Mouse IgG1 | In-house | 1 pg/mL |
| CD28-142Nd | BD Biosciences | 555725 | CD28.2 | Mouse IgG1 | In-house | 2 pg/mL |
| CD272-143Nd | Biolegend | 344502 | MIH26 | Mouse IgG2a | In-house | 1 pg/mL |
| CD279-144Nd | BD Biosciences | 562138 | EH12.1 | Mouse IgG1 | In-house | 4 pg/mL |
| CD4-145Nd | Fluidigm | 3145001B | RPA-T4 | Mouse IgG1 | Fluidigm | 1 Test |
| CD8a-146Nd | Fluidigm | 3146001B | RPA-T8 | Mouse IgG1 | Fluidigm | 1 Test |
| CD57-147Sm | Biolegend | 322302 | HCD57 | Mouse IgM | In-house | 0.5 pg/mL |
| CD95-148Nd | Biolegend | 305602 | DX2 | Mouse IgG1 | In-house | 2 pg/mL |
| CD25-149Sm | Fluidigm | 3149010B | 2A3 | Mouse IgG1 | Fluidigm | 1 Test |
| CD7-150Nd | BD Biosciences | 555359 | M-T701 | Mouse IgG1 | In-house | 3 pg/mL |
| CD45RO-151Eu | Biolegend | 304202 | UCHL1 | Mouse IgG2a | In-house | 1 pg/mL |
| TCRγ5-152Sm | Fluidigm | 3152008B | 11F2 | Mouse IgG1 | Fluidigm | 1 Test |
| TIM3-153Eu | Fluidigm | 3153008B | F38-2E2 | Mouse IgG1 | Fluidigm** | 2 Tests |
| CD278-154Sm | Biolegend | 313502 | C398.4A | Hamster IgG | In-house | 1 pg/mL |
| CD223-155Gd | R&D Systems | AF2319 | Polyclonal | Goat IgG | In-house | 4 pg/mL |
| CD150-156Gd | Biolegend | 306302 | A12(7D4) | Mouse IgG1 | In-house | 2 pg/mL |
| CD134-158Gd | Fluidigm | 3158012B | ACT35 | Mouse IgG1 | Fluidigm | 1 Test |
| CD197-159Tb | Fluidigm | 3159003A | G043H7 | Mouse IgG2a | Fluidigm | 1 Test |
| CD137-160Gd | BD Biosciences | 555955 | 4B4-1 | Mouse IgG1 | In-house | 4 pg/mL |
| CD14-161Dy | BD Biosciences | 555396 | M5E2 | Mouse IgG2a | In-house | 2 pg/mL |
| CD19-161Dy | BD Biosciences | 555410 | HIB19 | Mouse IgG1 | In-house | 0.5 pg/mL |
| CD20-161Dy | BD Biosciences | 555621 | 2H7 | Mouse IgG2b | In-house | 2 pg/mL |
| CD33-161Dy | BD Biosciences | 555449 | WM53 | Mouse IgG1 | In-house | 1 pg/mL |
| CD69-162Dy | Fluidigm | 3162001B | FN50 | Mouse IgG1 | Fluidigm** | 0.5 Test |
| CD183-163Dy | Biolegend | 353702 | G025H7 | Mouse IgG1 | In-house | 2 pg/mL |
| prpS6-164Dy* | BD PhosphoFlow | 624084 | N7-548 | Mouse IgG1 | In-house | 2 pg/mL |
| CD127-165Ho | Fluidigm | 3165008B | A019D5 | Mouse IgG1 | Fluidigm | 1 Test |
| CD27-167Er | Fluidigm | 3167006B | L128 | Mouse IgG1 | Fluidigm | 1 Test |
| CD38-168Er | Biolegend | 303502 | HIT2 | Mouse IgG1 | In-house | 3 pg/mL |
| CD45RA-169Tm | Fluidigm | 3169008B | HI100 | Mouse IgG1 | Fluidigm | 1 Test |
| CD3E-170Er | Fluidigm | 3170001B | UCHT1 | Mouse IgG1 | Fluidigm | 1 Test |
| FITC-172Yb* | Southern Biotech | 6400-01 | Polyclonal | Sheep IgG | In-house | 8 pg/mL |
| Ki67-175Lu* | BD Biosciences | 556003 | B56 | Mouse IgG1 | In-house | 2 pg/mL | cPARP, cleaved PARP; prpS6, phosphorylated ribosomal protein S6. Related to FIGS. 2-5.
*These antibodies were used for intracellular staining (post-methanol). Remaining antibodies were used during surface staining (prior to methanol permeabilization).
**Recommended concentrations were adjusted based on in-house titration results.

TABLE 3

T-cell phenotype and functional protein marker.

| Name | Alias | Description | Function |
|---|---|---|---|
| CD3E | | Part of TCR-CD3 complex | Couples antigen recognition to intracellular signaling |
| CD8a | | Marker of CD8+ T cells | Co-receptor of TCR signaling, binds to MHC class I |
| CD45 | PTPRC | Leukocyte marker | Tyrosine phosphatase, suppresses TCR signaling |
| CD45RA | | $T_N$ and $T_{SCM}$ marker | CD45 isoform enforcing high TCR signaling threshold |
| CD45RO | | $T_{CM}$ and $T_{EM}$ marker | CD45 isoform that lowers TCR signaling threshold |
| CD95 | FAS | $T_{SCM}$ marker | Controls apoptosis, transduces proliferation signals |
| CD127 | IL7Rα | $T_N$, $T_{CM}$, $T_{EM}$, $T_{SCM}$ marker | Mediates IL-7-driven homeostatic proliferation and survival |
| CD197 | CCR7 | $T_N$, $T_{CM}$, $T_{SCM}$ marker | Controls homing to spleen and lymph nodes, binds CCL19/21 |
| CD25 | IL2Rα | Activation marker | Mediates IL-2 signaling, induces cell proliferation |
| CD38 | ADPRC1 | Activation marker | Catalyzes synthesis and hydrolysis of cADP-ribose |
| CD69 | | Activation marker | C-type lectin, suppresses inflammation, binds galectin-1 |
| CD183 | CXCR3 | Chemokine receptor | Controls T-cell trafficking in response to CXCL9/10/11 |
| CD7 | | Co-stimulatory receptor* | Galectin-1 receptor, activates PI3K and integrins |
| CD27 | | Co-stimulatory receptor* | Controls long-term survival of T cells, binds to CD70 |
| CD28 | | Co-stimulatory receptor* | Provides strong co-stimulation signal, binds to CD80/CD86 |
| CD134 | OX40 | Co-stimulatory receptor | Supports survival of activated T cells, binds to OX4OL |
| CD137 | 4-1BB | Co-stimulatory receptor | Enhances T-cell activation, binds to TNFSF9 (CD137L) |
| CD278 | ICOS | Co-stimulatory receptor | Enhances T-cell activation, binds to CD275 (ICOSLG) |
| CD150 | SLAMF1 | Inhibitory receptor | Can facilitate immune tolerance or type 11 immunity |
| CD223 | LAG3 | Inhibitory receptor | Promotes immune tolerance, binds to MHC class II |
| CD272 | BTLA | Inhibitory receptor | Suppresses T-cell effector function, binds CD270 (HVEM) |
| CD279 | PD1 | Inhibitory receptor | Promotes tolerance, binds to CD274/CD273 (PDL1/PDL2) |

TABLE 3-continued

T-cell phenotype and functional protein marker.

| Name | Alias | Description | Function |
|------|-------|-------------|----------|
| CD366 | TIM3 | Inhibitory receptor | Galectin-9 receptor, suppresses T-cell effector function |
| CD57 | HNK1 | Senescence marker | Oligosaccharide epitope, binds to L/P-selectins and laminin |
| Ki-67 | | Proliferation marker | Chromosome segregation during cell division |
| prpS6 | | Protein translation marker | Phosphorylated rpS6 on S235/236 facilitates translation |

*Also a marker of $T_N$, $T_{CM}$, $T_{EM}$, and $T_{SCM}$ subsets. Related to Fig. 4.

Tracking individual protein expression in CD8+ T cells from the naïve resting state showed that expression of some markers changes strongly based on the number of divisions independent of the time point examined (e.g., up: CD25 and CD45RO, or down: CD69 and CD45RA; FIG. 3A-3D). Further, the relationship between the level of marker expression and proliferative history could be counterintuitive. For example, T cells expressing the lowest level of CD69, which could normally be considered as poorly activated, had divided the most (FIG. 3A). In contrast, expression of other markers was relatively consistent across divisions (e.g., LAG3 and BLTA).

Figure 4A:
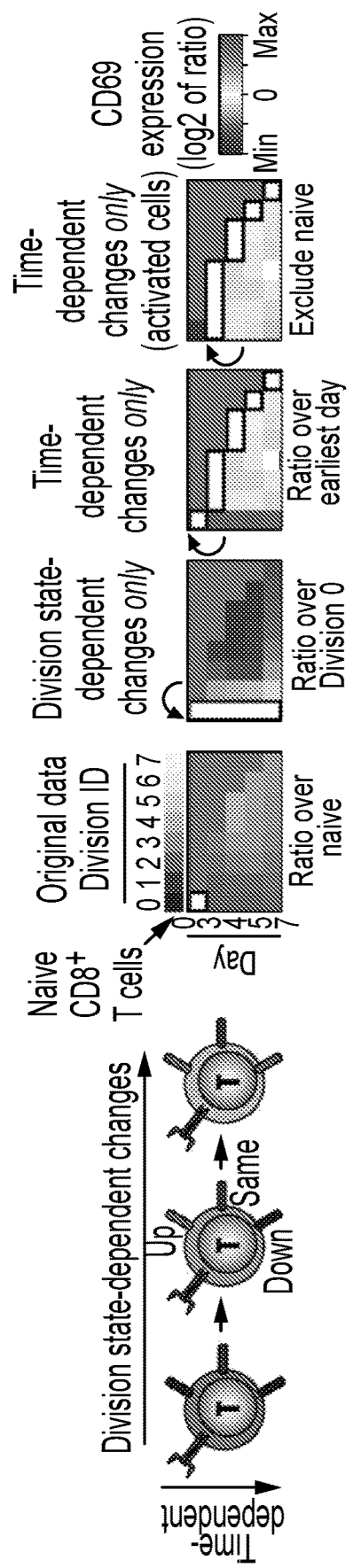
Figures 1, 4B:
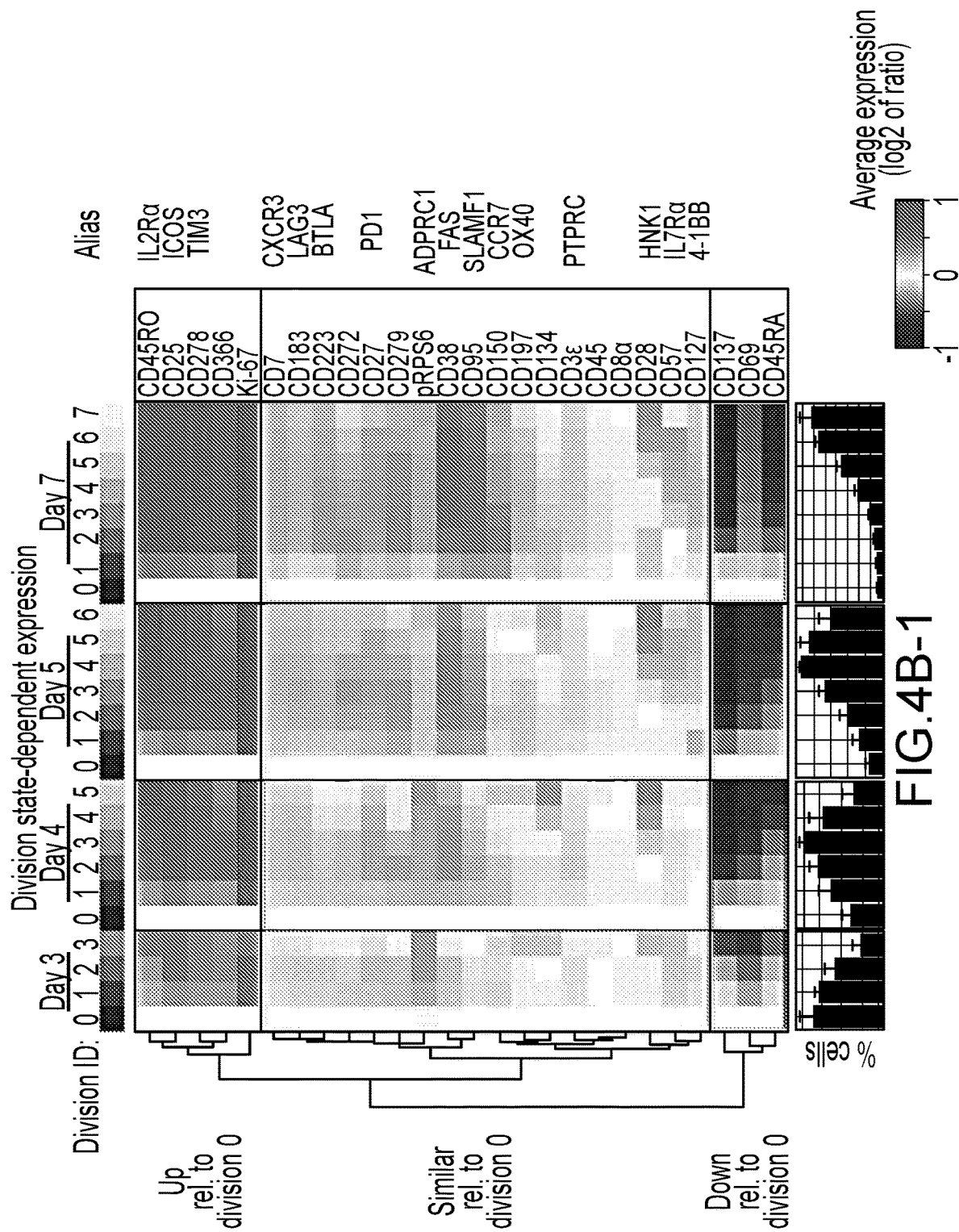
Figures 2, 4B:
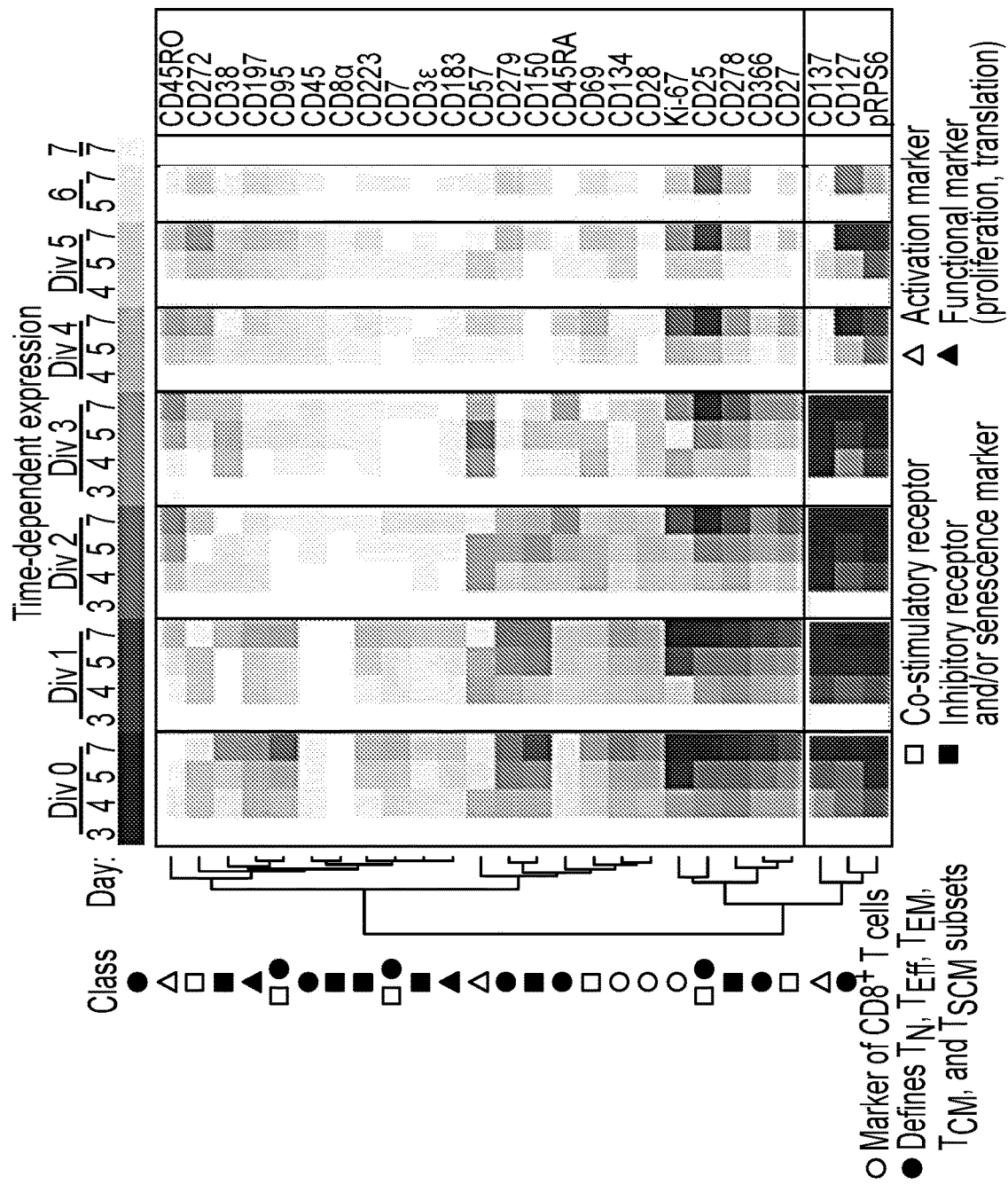
Figure 4C:
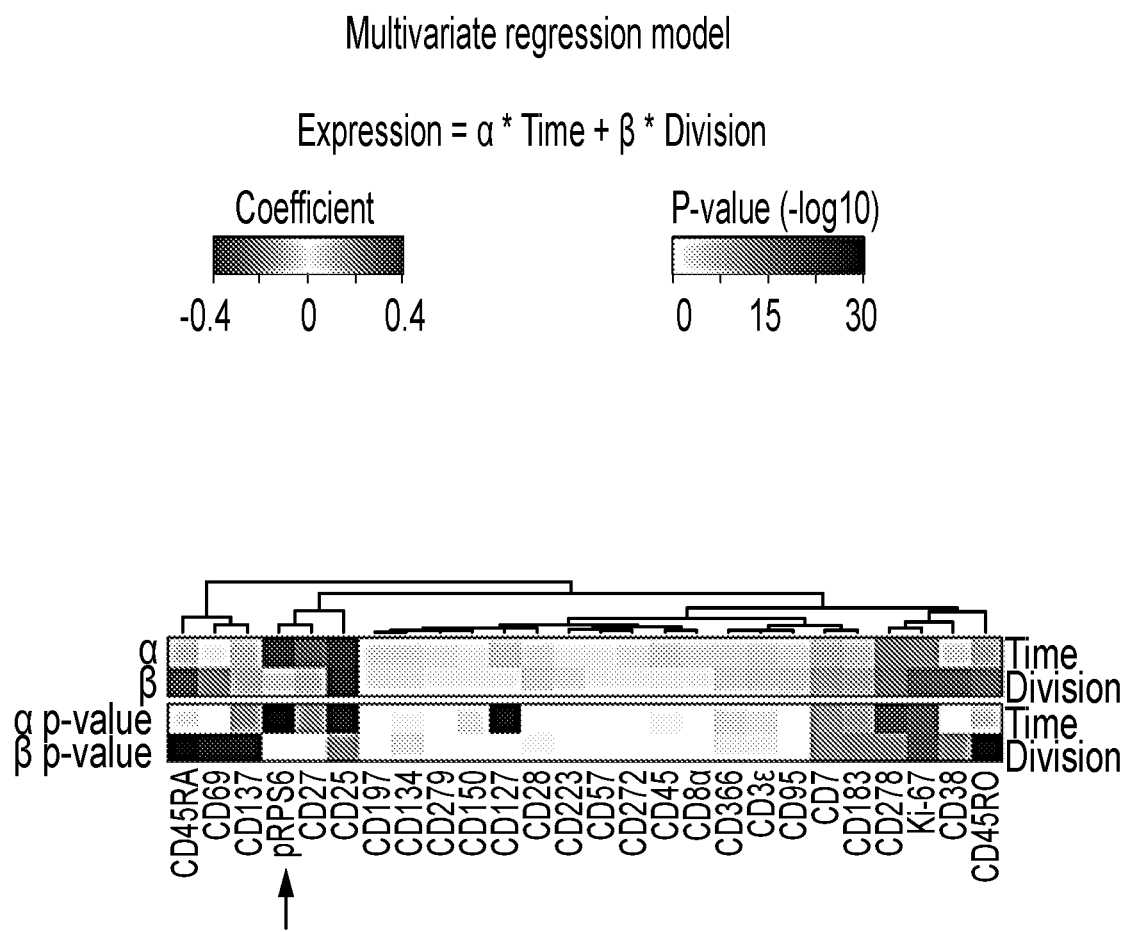

To separate division-dependent from time-dependent changes, average marker expression to either division 0 for each day, or to the earliest time point for each division, respectively was normalized (FIG. 4A). This analysis showed that division-dependent changes (especially upregulation) are generally more pronounced than time-dependent changes (FIGS. 4B-1 and 4B-2). Moreover, with the exception of co-stimulatory receptor CD137 (4-1BB), time and division-dependent changes were either uncoupled (uncorrelated) or reversed (anticorrelated). For instance, expression of CD69 decreased strongly with divisions at each day, yet changed little with time at each division. In contrast, CD25 expression increased in division-dependent manner, but was generally reduced in time-dependent fashion. Overall, the consistency and magnitude of division-dependent trends regardless of the time point examined indicate a fundamental link between differentiation and proliferation during early specification of naïve CD8+ T cells in this expansion setting.

Example 9: T-Cell Phenotypic Diversity is Largest Prior to the First Division

An unanticipated observation from our analysis of division- and time-dependent changes was the fact that cellular diversity (estimated by standard deviation, s.d., in arcsin h-transformed expression) was decreasing consistently in division-dependent (but not time-dependent) manner for the majority of individual markers examined. This observation and the differentiation proliferation link prompted us to take advantage of the high-dimensional nature of our single-cell data to better understand naïve CD8+ T-cell differentiation across divisions.

Figure 5A:
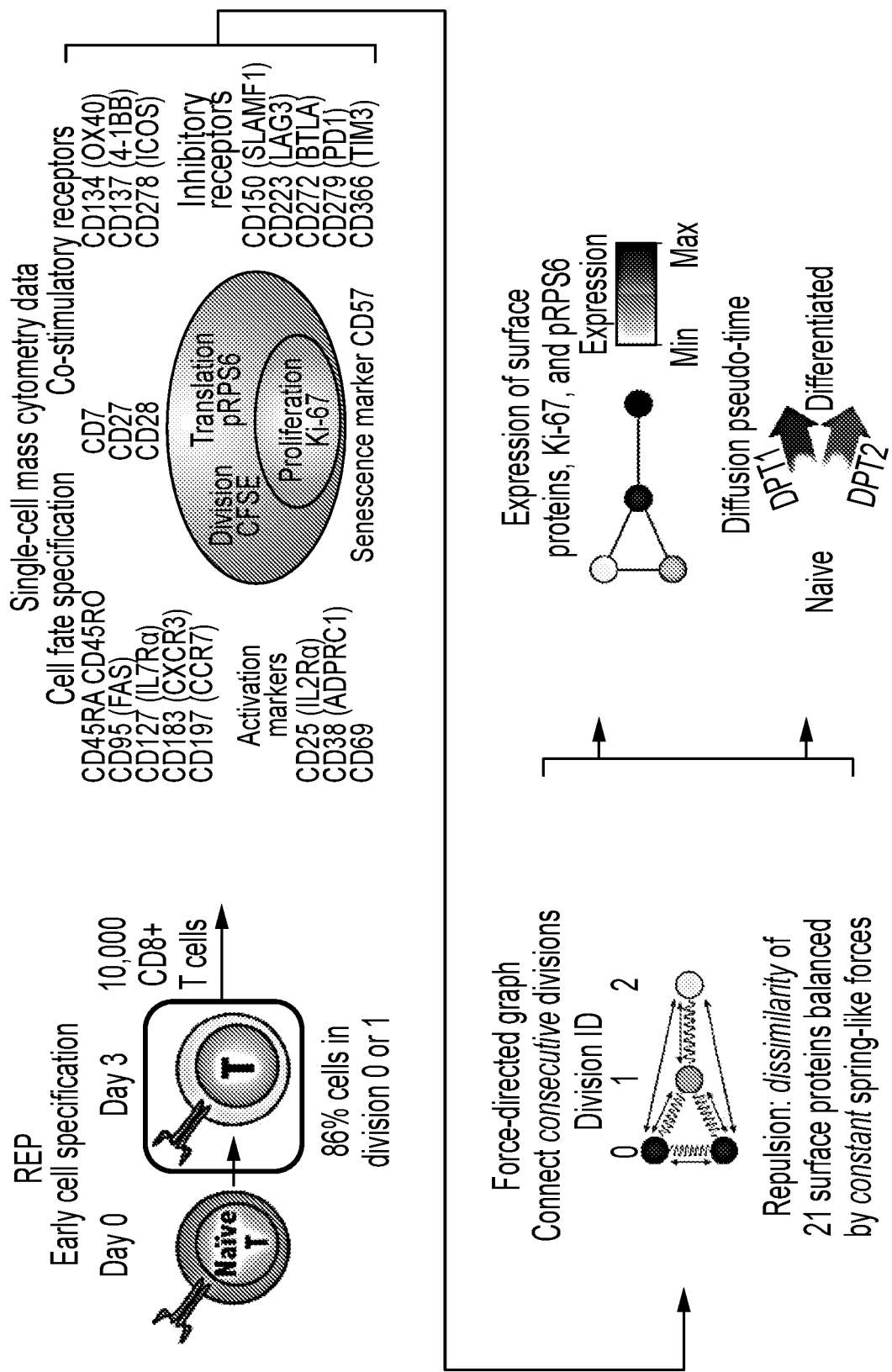
FIGS. 5A-5G show that undivided cells have the highest phenotypic diversity on day 3 of naïve T-cell differentiation.

The first focus was on the earliest time point that could reveal insights into T-cell fate selection: day 3, when the majority of cells were still in either division 0 or 1 (FIG. 5A). To visualize high-dimensional single-cell data, a force-directed graph was created using Vortex software for analysis and clustering of single-cell data. In such graph, cells repulse with forces proportional to their difference in their dissimilarity in multidimensional protein expression, while edges hold cells together by constant spring-like forces. These repulsive and attractive forces eventually converge to a balanced state, which aids data interpretation. Here, Vortex was extended to implement ideas from FLOW-MAP algorithm by allowing edge connections either between consecutive time points, as in the FLOW-MAP algorithm, or between subsequent divisions to take advantage of our proliferative history data. As such, the single-cell force-directed phenotypic maps presented here only connect cells within neighboring division IDs (−1, 0, +1).

Figure 5B:
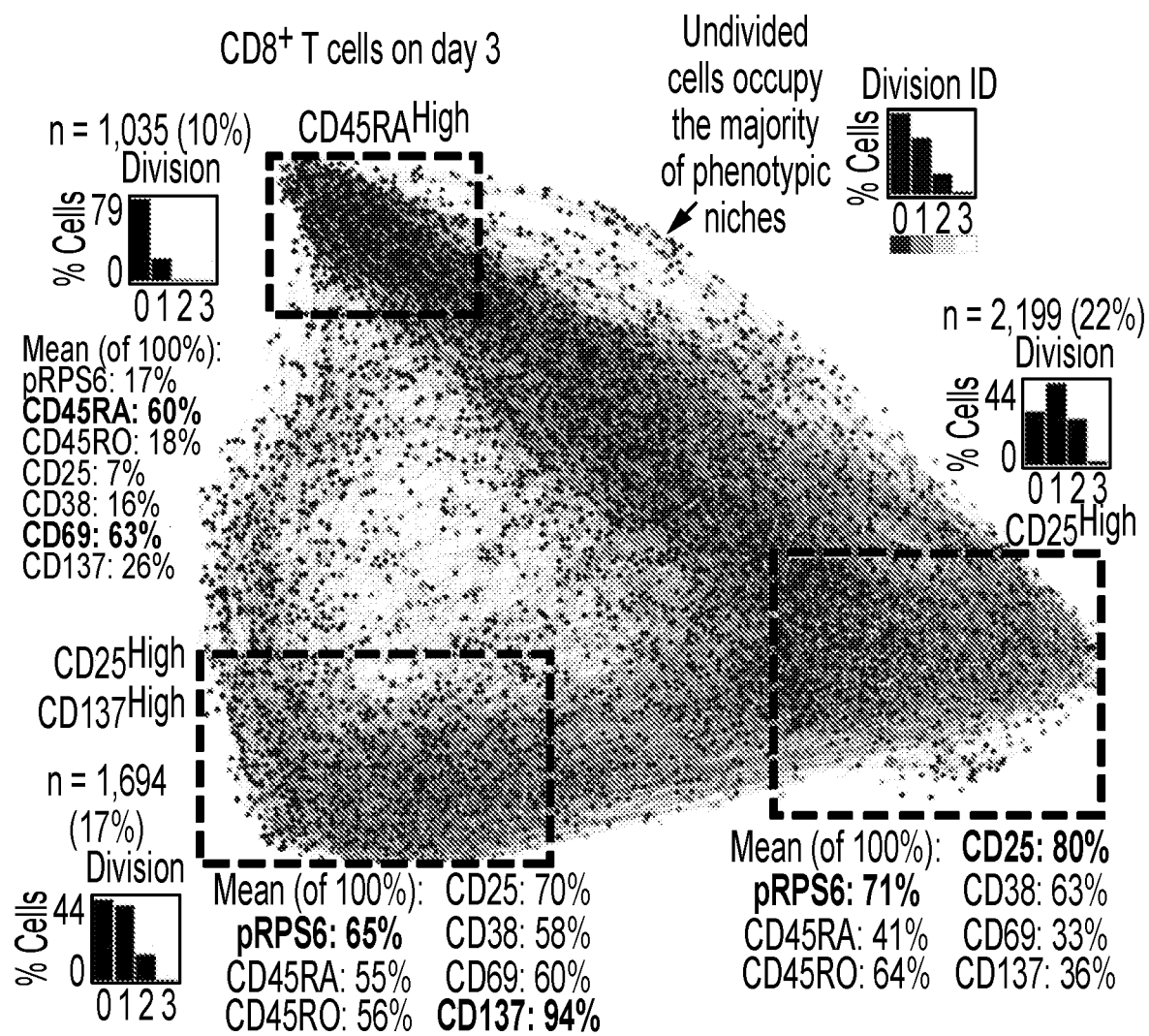

Surprisingly division state of cells in a force-directed graph did not follow an expected increase in cellular diversity, which would be indicative of fate specification with successive divisions. Instead, undivided cells occupied the majority of phenotypic niches (FIG. 5B). Protein expression in this graph was examined to define regions that are most similar and most different from naïve cells. Note that there are nearly no naïve cells remaining in REP culture by day 3 (e.g., 99.2% of undivided cells in this sample were $CD69^{High}$; FIG. 3C). Moreover, cells in the $CD45RA^{High}$ region, which could be interpreted as the most similar to naïve express CD69 and are phenotypically distinct from true naïve cells on day 0, suggesting that the observed diversity of undivided cell states is not due to the lack of cell activation.

Figure 5C:
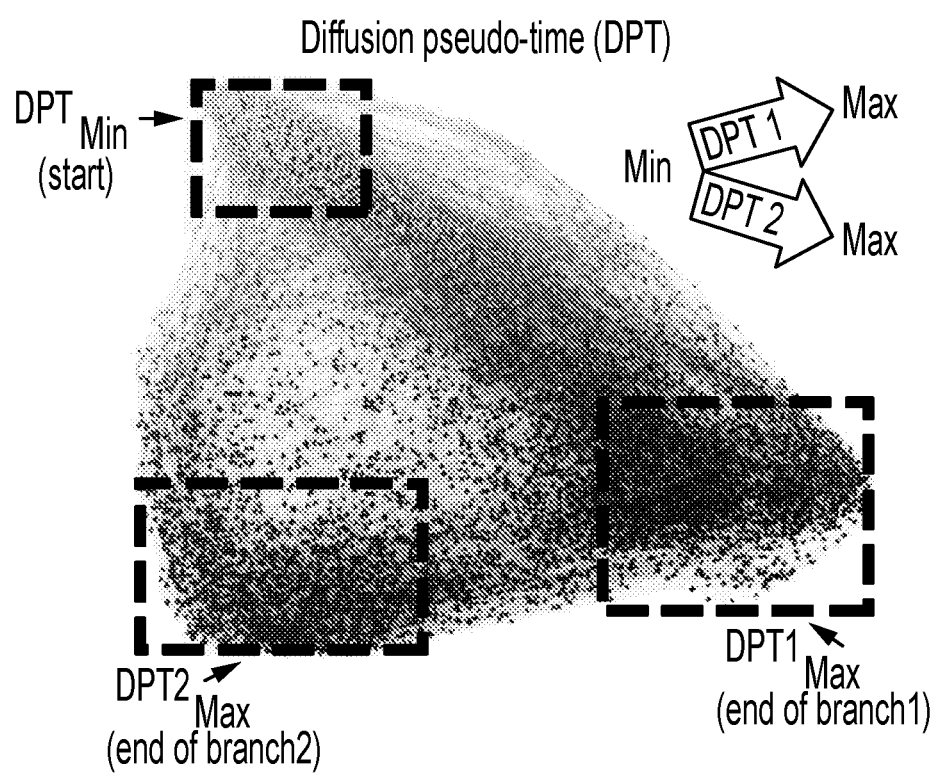
Figure 5D:
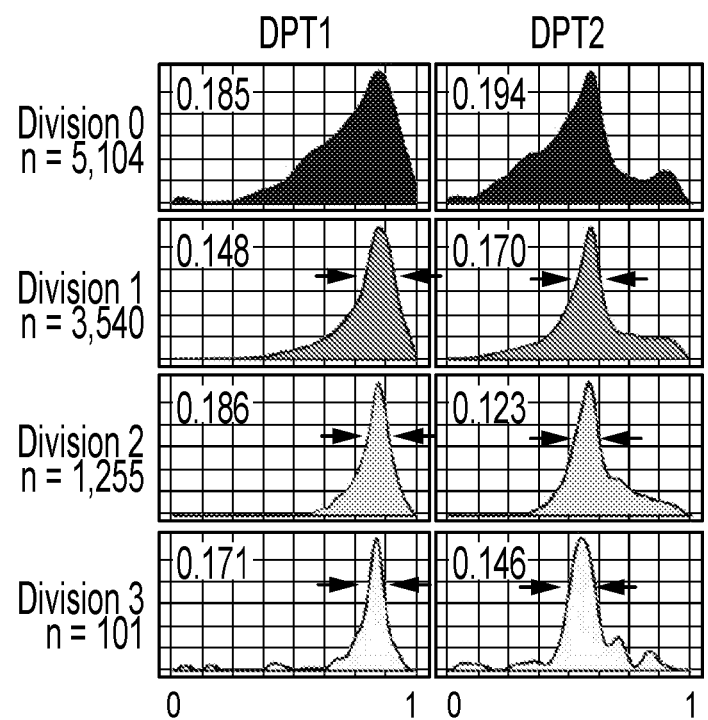
Figure 5E:
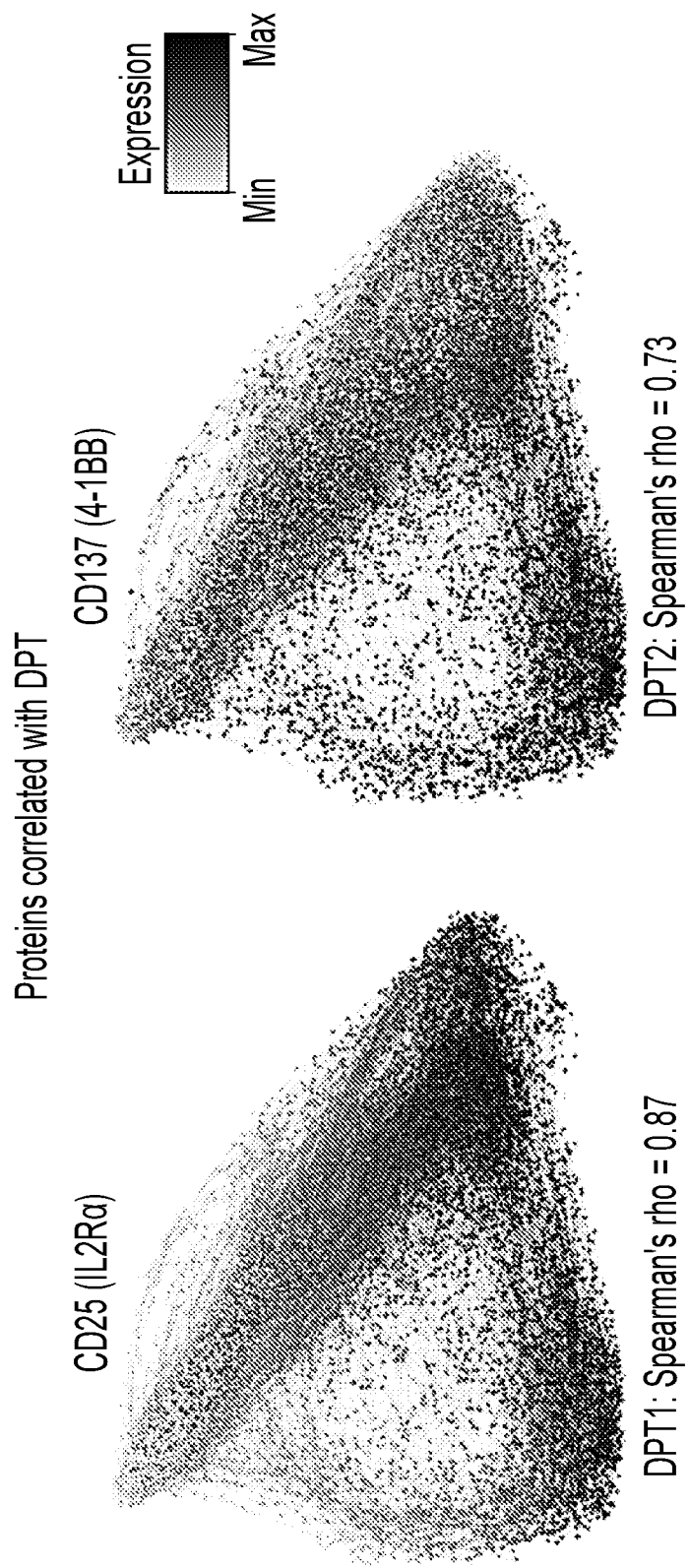

To understand how cells advanced through phenotypic space in our force-directed graph, diffusion maps were applied. This method is especially well suited for mapping continuous branching differentiation, such as multilineage hematopoiesis. By embedding cells into diffusion components, diffusion maps identify the most likely sequence of transition probabilities, a metric called diffusion pseudotime (DPT). Overlaying DPT onto the force-directed graph exposed a continuum of phenotypes from the least differentiated (closest to naïve) to the two most differentiated (distinct from naïve) states (FIG. 5C). Importantly, undivided cells had the highest DPT diversity (estimated by s.d.), and completely covered the range of DPT values (FIG. 5D). Using lasso, a regularized multivariate regression method, it was found that CD25 and CD137 protein levels had the highest coefficient for predicting DPT1 and DPT2, respectively (FIG. 5E). This finding was corroborated by a correlation analysis (FIG. 5E). This suggests that early cell fate decisions during expansion and differentiation of naïve CD8+ T cells could be dependent of the balance between IL-2 and CD137 ligand co-stimulatory signaling pathways.

Figure 5F:
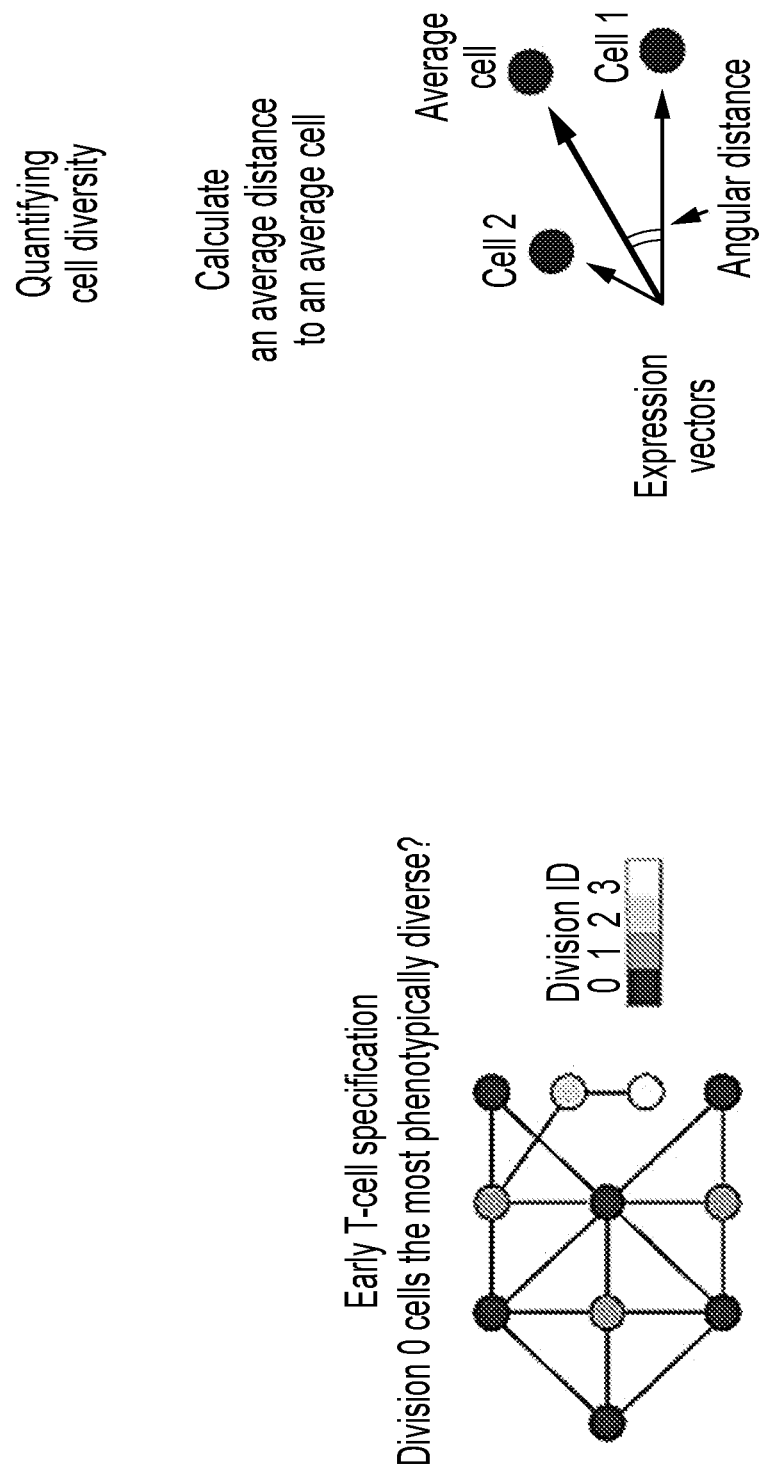
Figure 5G:
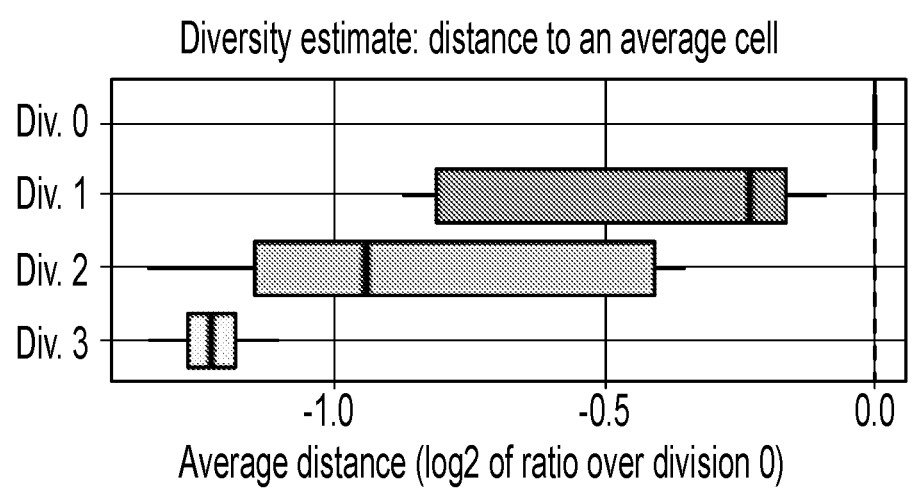
Figure 5I:
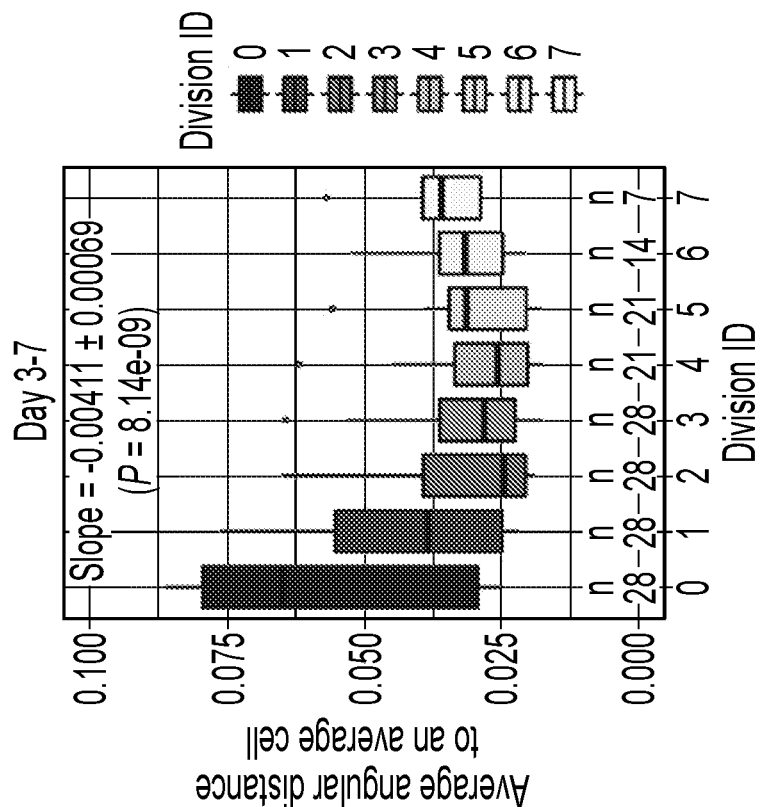
FIG. 5I: Mean phenotypic diversity on REP days 3, 4, 5, and 7 (n=28 samples containing 4 time points from 2 experiments). Phenotypic diversity in (g-h) was calculated as described in (f) using arsinh-transformed expression of 18 common protein markers. To assess evidence for a decrease in phenotypic diversity with division in (g-h), linear mixed-effects models were used; slope±standard error (s.e.) and associated P-values are shown above each plot.
Figure 5H:
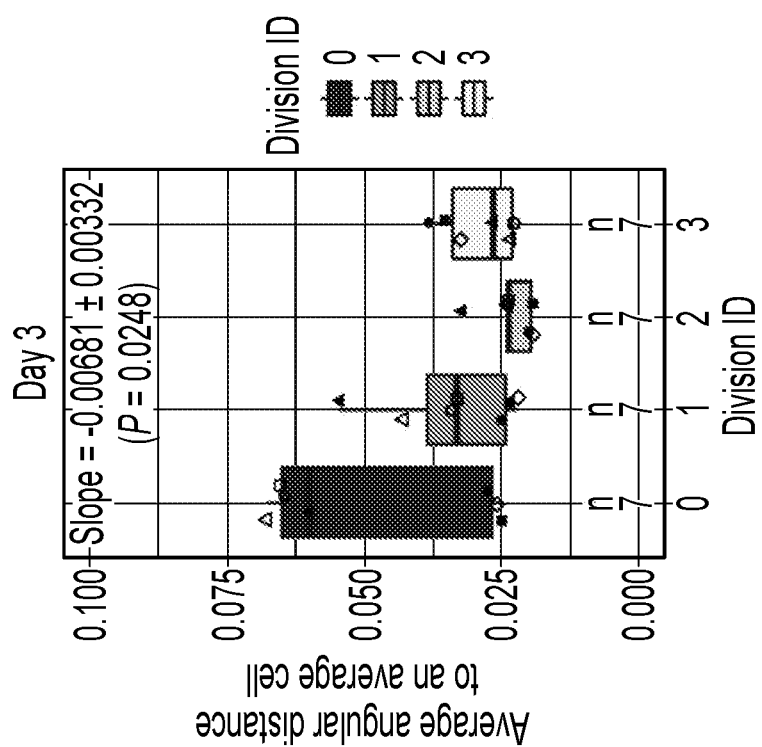
FIG. 5H: Boxplot showing mean phenotypic diversity of CFSE+ CD8+ T cells within each division state on day 3 of REP (n=7 samples from 2 experiments).
Figure 12A:
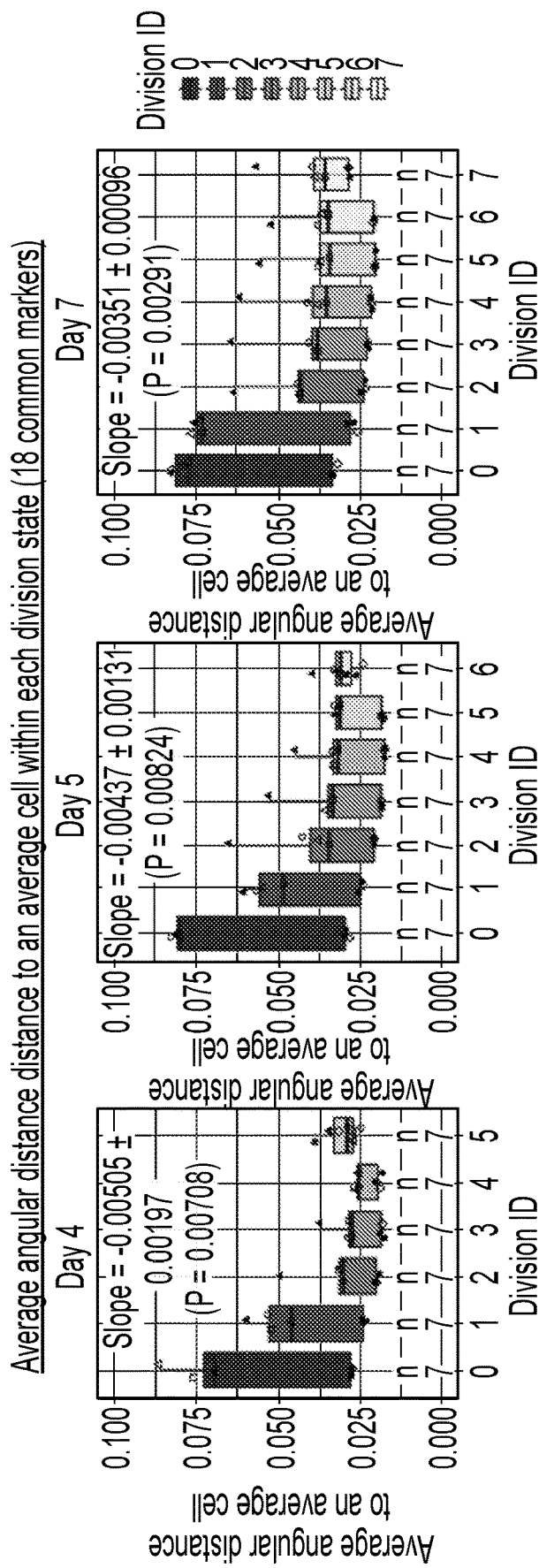
FIGS. 12A-12C depict high-dimensional phenotypic diversity calculated based on mass cytometry data decreases with division state.
Figure 12B:
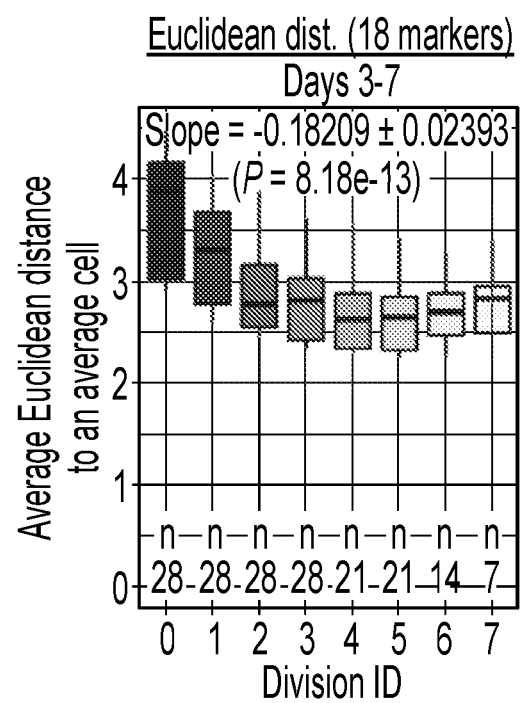
Figure 12C:
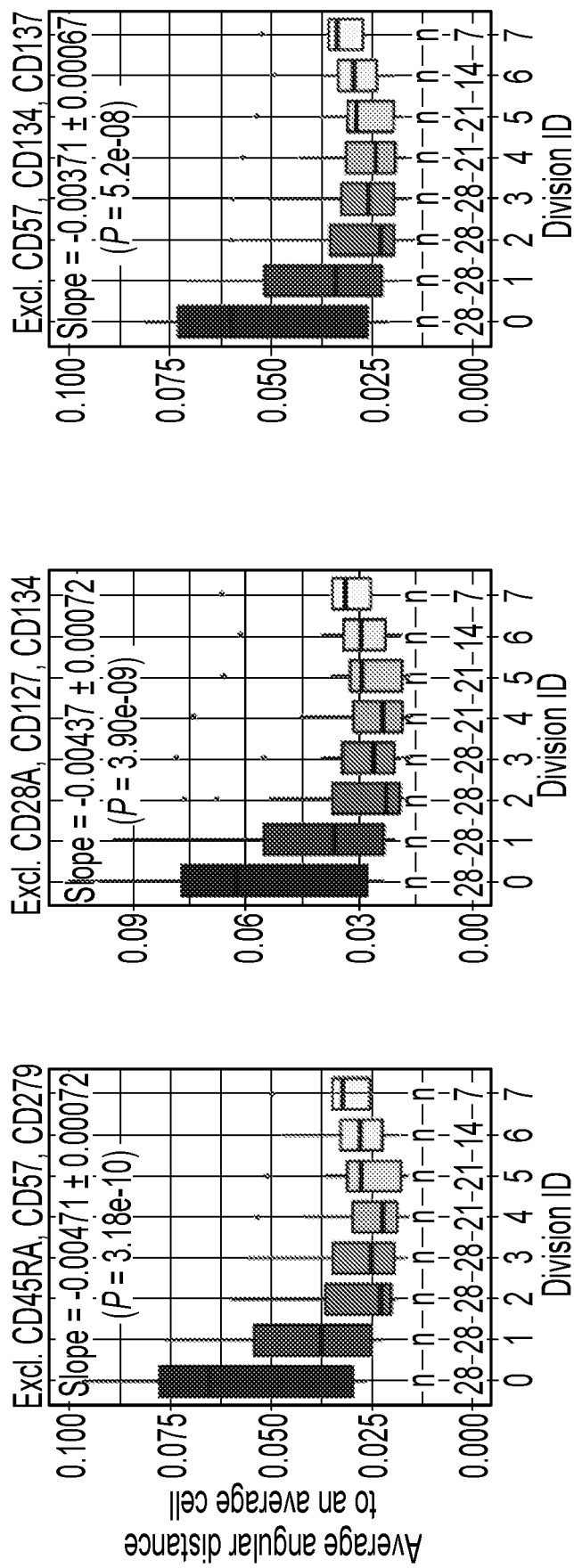
Figure 13A:
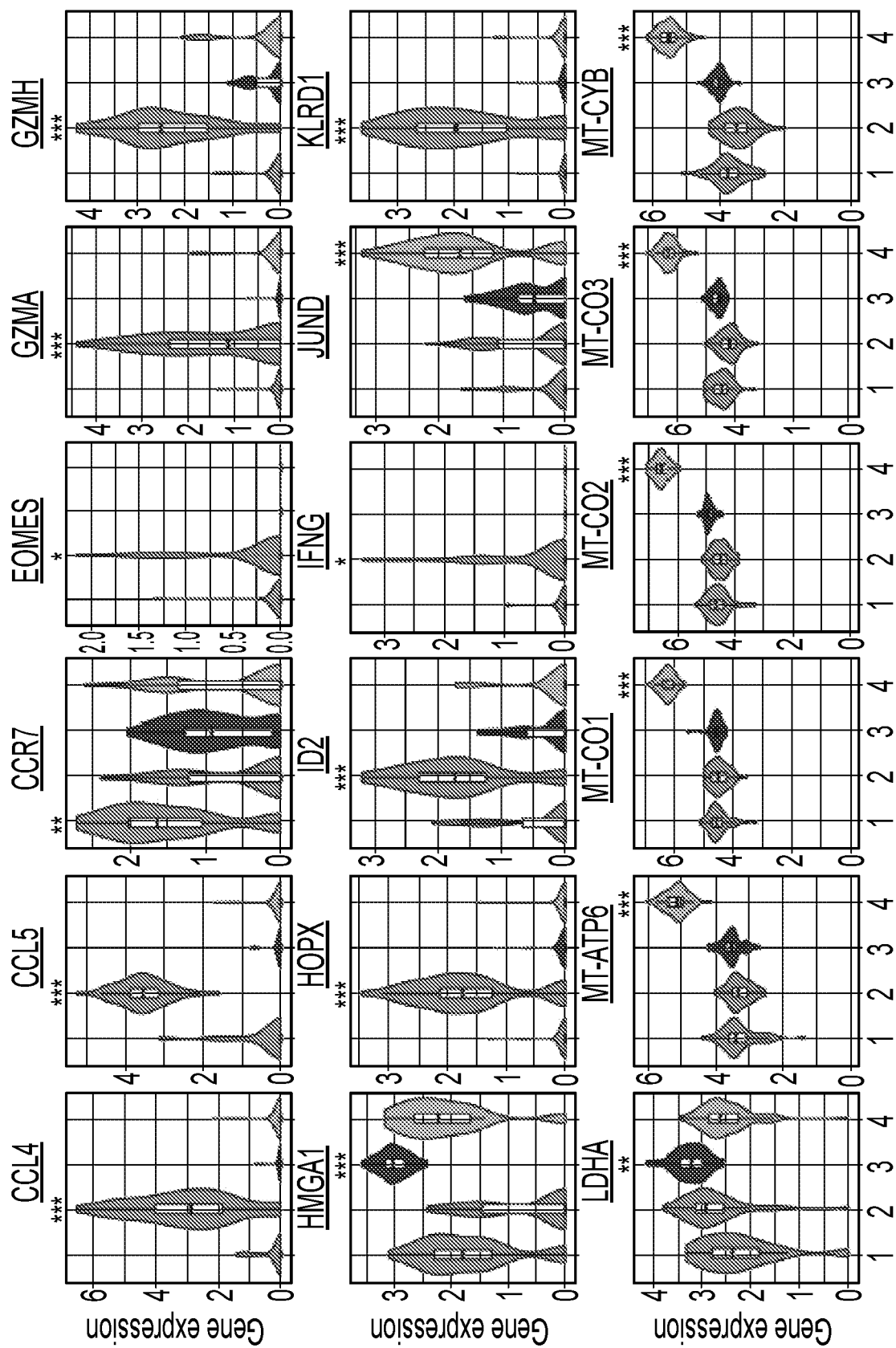
FIG. 13 depicts selected single-cell gene expression in regions 1-4 of a force directed graph showing early divergence of naïve T cells on day 3 of REP. Regions 1-4 were defined in FIG. 9C based on cell coordinates in a force-directed graph constructed using expression of 1,000 most variably expressed genes in CFSE+ CD8+ T cells on day 3 of REP. n=50 cells from each region were then selected based on DPT values: $DPT^{Low}$ for regions 1 and 4, $DPT2^{High}$ for region 2, and $DPT1^{High}$ for region 3. Individual gene expression is shown as a violin plot with a box plot for genes that are significantly enriched in a given region. Kruskal-Wallis H test P<1e-3 for each gene shown; WMW U test comparing the highlighted region to each other region in a pairwise manner is noted as '*' for P<0.05, '' for P<0.01, and '*' for P<0.001. WMW P-values were corrected for multiple hypotheses testing using Bonferroni correction.
Figure 13B:
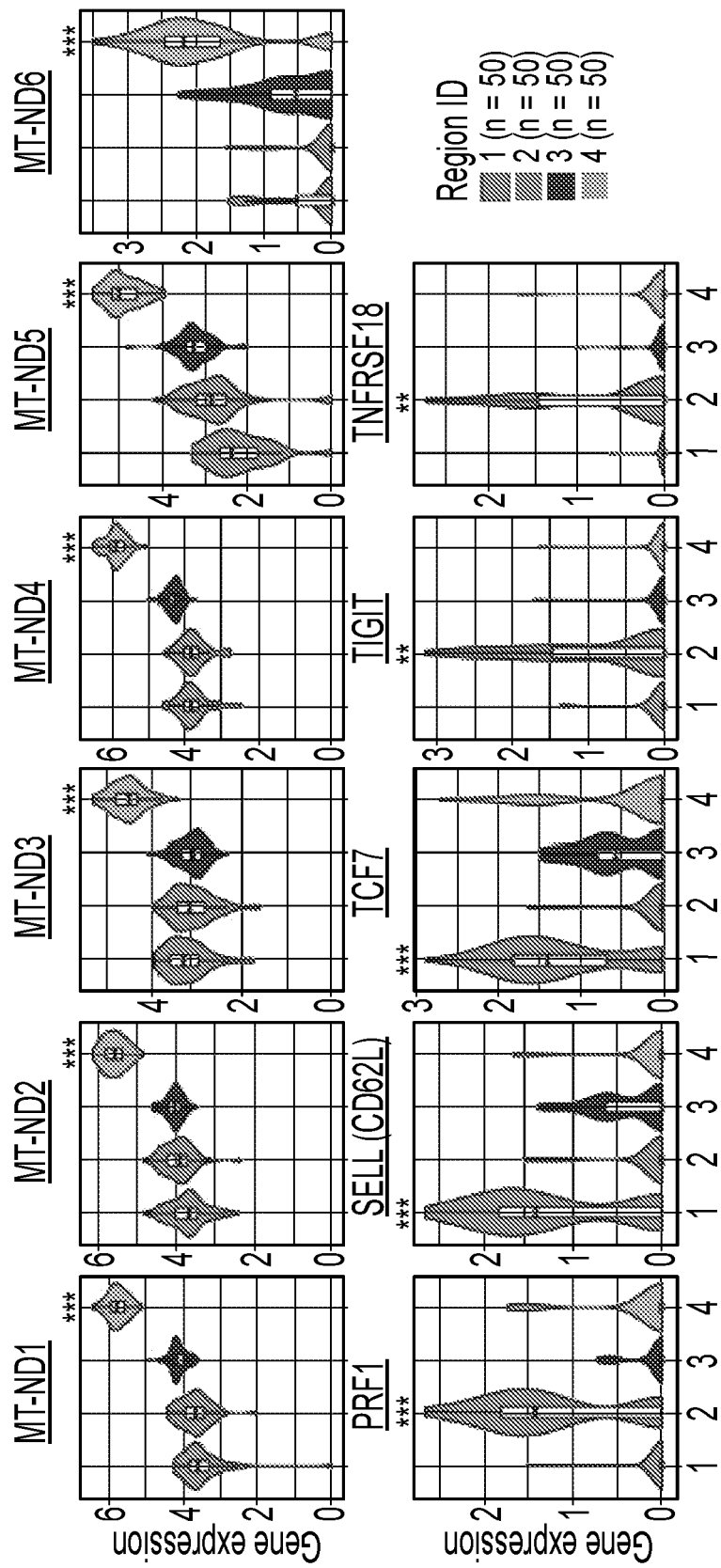
Figure 14:
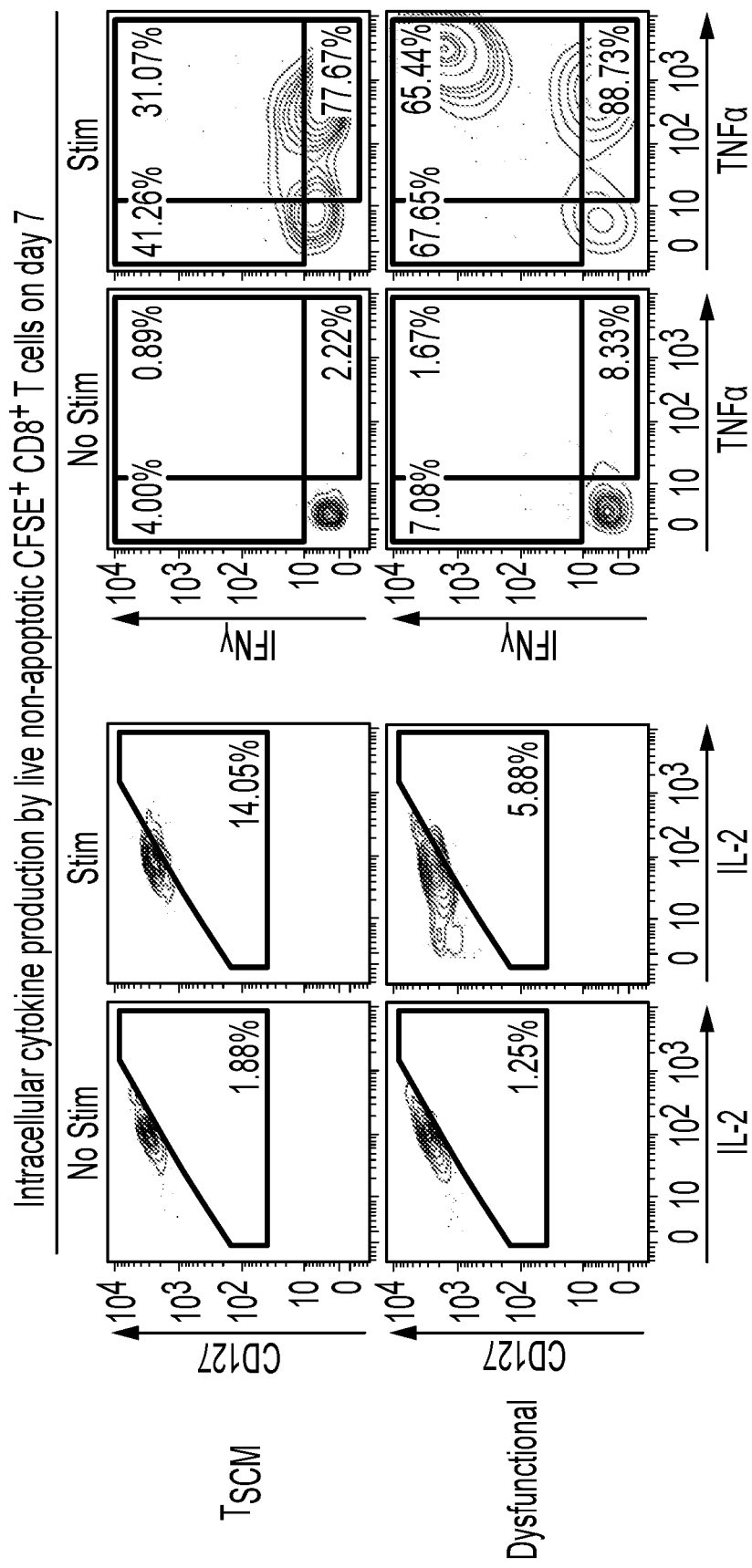
FIG. 14 depicts intracellular cytokine production by putative $T_{SCM}$ and dysfunctional T-cell subsets. Naïve CFSE+ T cells were expanded using REP for 7 days. Next, intracellular production of IL-2, IFN-γ, and TNF-α was assessed by stimulating cells with phorbol 12-myristate 13-acetate (PMA) and ionomycin for 4 hours. Cells were stained using an antibody panel in Table 5 and assessed by mass cytometry. Live non-apoptotic CFSE+ CD8+ T cells were gated as putative $T_{SCM}$ (antigen-experienced CD27+ CD45RA+ CTLA4−) or dysfunctional (antigen-experienced CD27− CTLA4+) cells.

As an independent metric of high-dimensional cellular diversity, average angular distance to an average cell within each division was calculated (FIG. 5F). This approach confirmed that undivided cells had the highest phenotypic diversity and phenotypic diversity significantly decreases with successive division (FIG. 5G). Further, this observation held true on subsequent days (FIG. 5I, FIG. 12A) examined if calculated using Euclidean distance (FIG. 12B), or when sets of 15 markers were randomly sampled to calculate angular distance (FIG. 12B). Together, these data confirm that the largest T-cell diversity occurs prior to the first division in our system.

This observation that T-cell phenotypic diversity is largest in undivided cells suggests that important fate selection decisions may take place before asymmetric cell division could occur. If true, drug treatment may be most effective in changing T-cell fate if applied early in T cell activation process.

Figure 9D:
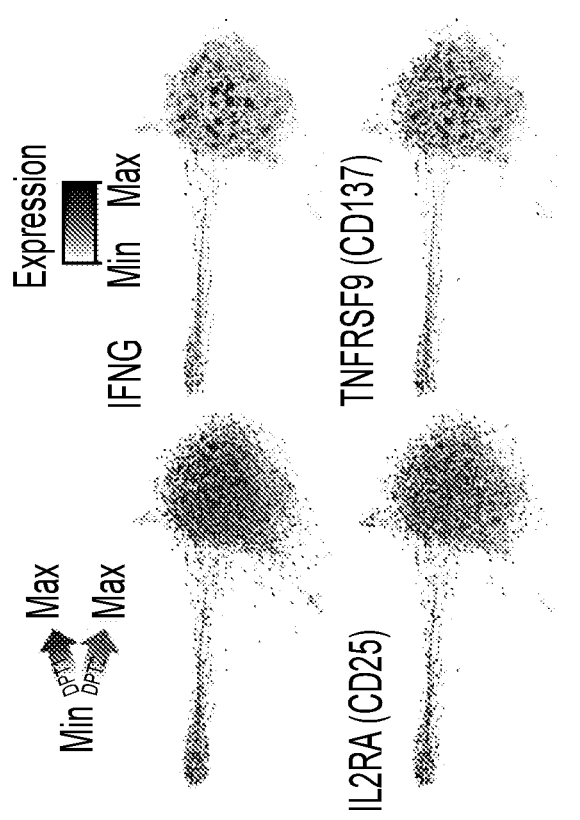
Figure 9E:
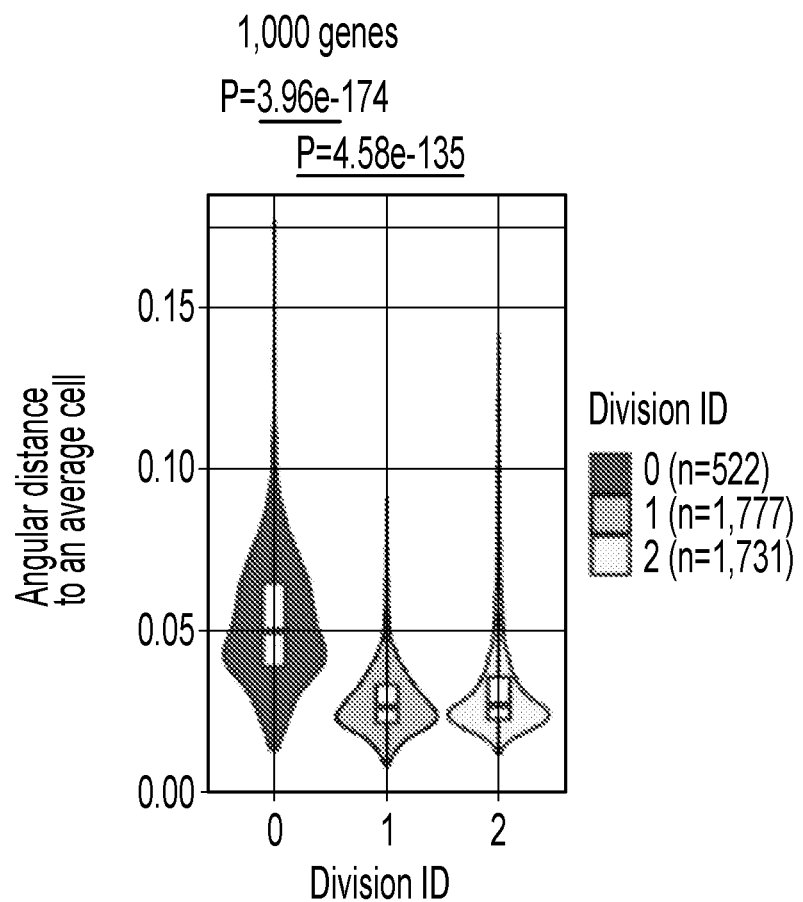
Figure 9F:
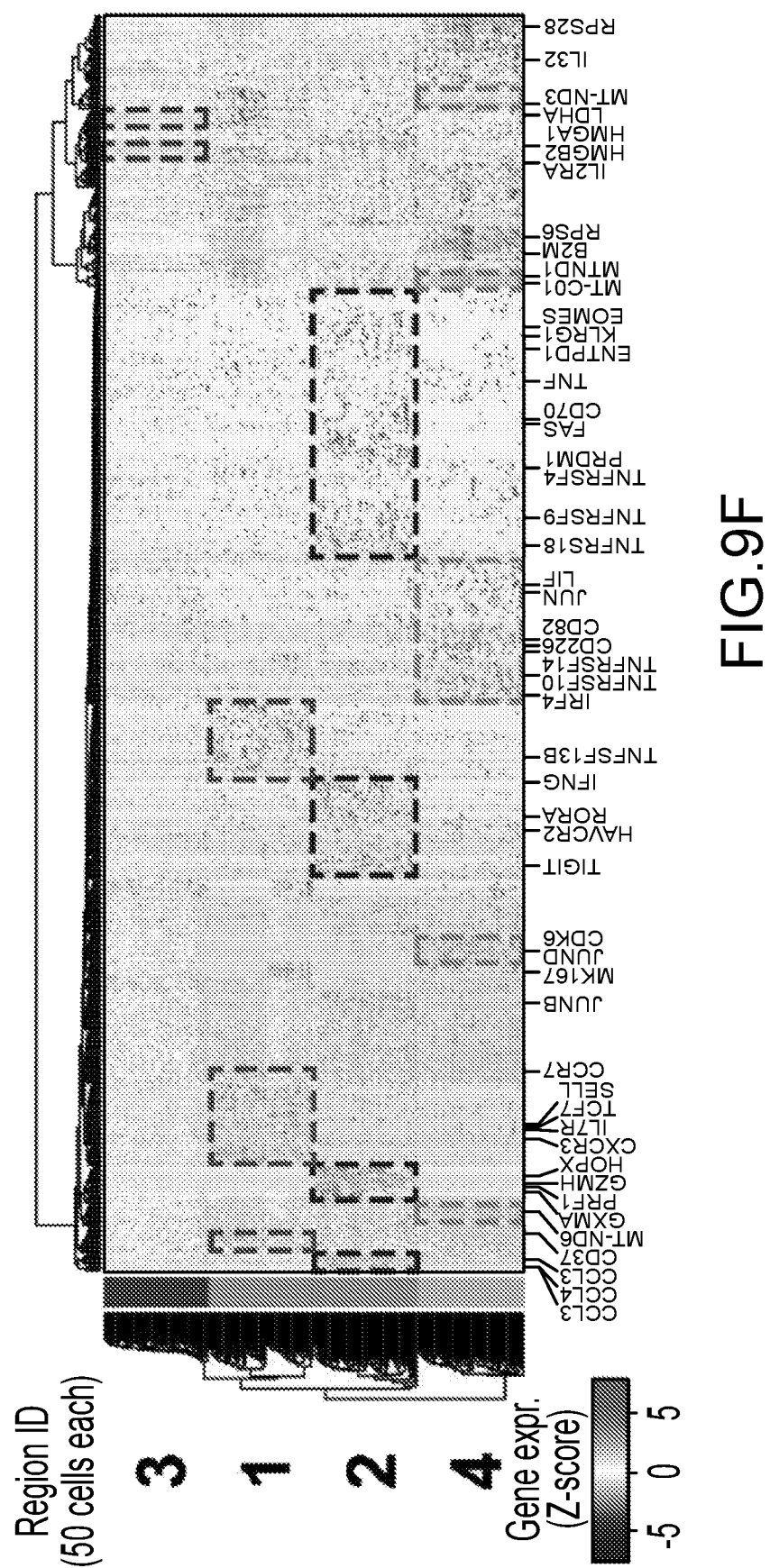

Undivided CD8+ T Cells are the Most Transcriptionally Diverse Following Activation While the phenotypic assessment of cellular diversity by mass cytometry is robust and high-throughput, it is dependent on the selection of targeted cellular features based on prior knowledge. As such, to obtain and orthogonal view of diversity during early CD8+ T-cell differentiation without target bias, droplet-based single-cell RNA-sequencing was performed on CD8+ T cells prospectively isolated from division states 0, 1, or 2 on day 3 of REP (FIGS. 9A-9B). The 1,000 most variably expressed genes were then selected to construct a force-directed graph. Again, undivided cells occupied the majority of cellular niches (FIG. 9C and) and were present in the 4 regions of the graph associated with a complete range of DPT1 and DPT2 values (FIGS. 9C-9D). Further, undivided CD8+ T cells in REP had a significantly higher phenotypic diversity than cells that divided either once or twice, when quantified as an angular distance to an average cell within each division state based on: the 1,000 most variably expressed genes (FIG. 9E), all genes (FIG. 10A), the same genes as assessed by mass cytometry (FIG. 10B), or if quantified based on Euclidean distance (FIG. 10C).

To better understand the basis of undivided cell diversity and early CD8+ T-cell fate decisions, gene expression in 4 regions of our map was further examined (FIGS. 9C-9F). Cells from region 1 (defined as $DPT^{Low}$) contained mostly (78.2%) undivided cells that expressed genes consistent with the least differentiation state (e.g. SELL encoding CD62L). Cells from region 2 ($DPT2^{High}$) were significantly enriched for expression of genes associated with effector function, including cytokines (IFNG), cytolytic molecules (GZMA, GZMH, and PRF1), and transcriptional regulators (EOMES, HOPX, and ID2). Cells from region 3 ($DPT1^{High}$) appeared proliferating and expressed genes associated with glycolytic metabolism (e.g. LDHA), whereas cells from region 4 ($DPT^{Low}$) were the most divided and enriched for genes controlling oxidative phosphorylation (e.g. MT-ATP6, MT-COb, MT-CYB, and MT-ND1). As 100% of cells in region 2 were undivided, these results suggest that activated naïve CD8+ T cells in REP initially express effector genes without division, or proliferate utilizing different metabolic mechanisms that could be tied to the underlying cell function. More broadly, these data confirm that early CD8+ T-cell phenotypic diversity is the largest in undivided cells in REP, and provide insight into the identities of cell states generating transcriptional diversity.

Example 10: Ibrutinib Directs T-Cell Differentiation Towards $T_{SCM}$ Phenotype Given that important cell fate decisions are likely to occur in a T-cell's undivided state, without being bound to any particular theory, it is contemplated that a rationally selected drug treatment could change naïve T-cell fate if applied early in the activation process. By day 7, differentiation of CFSE+ CD8+ T cells expanded into new phenotypic niches and converged onto two main subpopulations. Based on the current nomenclature of human CD8+ T cells in cancer immunotherapy, these subpopulations resembled $T_{SCM}$ and dysfunctional cells. $T_{SCM}$ is a minimally differentiated subset of antigen-experienced T cells that is capable of reconstituting central memory ($T_{CM}$), effector memory ($T_{EM}$), and terminal effector ($T_{TE}$) cells. $T_{SCM}$ cells are clinically favorable for ACT due to their excellent engraftment, persistence, and efficacy against cancer cells. Dysfunctional cells are a subset of (reversibly) cell cycle-arrested and poorly functional (and thus clinically undesirable) T cells that express=2 inhibitory receptors, including PD1, LAG3, and CTLA4. In some embodiments, $T_{SCM}$ phenotype was defined as CD45RA+CD45RO− CD27+CD127+CCR7+PD1− CTLA4− CD57−, and dysfunctional phenotype as PD1+CTLA4+. In some embodiments, $T_{SCM}$ phenotype was defined as antigen-experienced (divided following TCR engagement) $CD45RA^{High}$ $CD45RO^{Low}$ $CD27^{High}$ $CD127^{High}$ $CCR7^{High}$ $CTLA4^{Low}$ $LAG3^{Low}$ $PD1^{Low}$ $CD57^{Low}$, and dysfunctional phenotype as antigen-experienced $CD27^{Low}$ $PD1^{High}$ $LAG3^{High}$ $CTLA4^{High}$ Relative to the $T_{SCM}$ like cells, dysfunctional phenotype cells were $CD45RA^{Low}$ $CD45RO^{High}$ $CD5^{Low}$ $CD7^{Low}$ $CD25^{High}$ $CD27^{Low}$ $CD52^{Low}$ $CD69^{High}$ $CCR7^{Low}$ and phenotypically contained a subpopulation expressing CD57 senescence marker. Since $T_{SCM}$ cells are similar to naïve T cells in their protein expression, allowing connections only among cells in consecutive division states was key to ensuring that true division history, which are defined cell locations in the final force-directed graph. For example, in FIGS. 6B-1, 6B-2, and 6B-3, this prevents naïve T cells (division 0, day 0) from directly connecting to $T_{SCM}$-like cells (divisions 5-7, day 7) without going to the activated cell states (divisions 0-5, days 3-5).

Figure 6A:
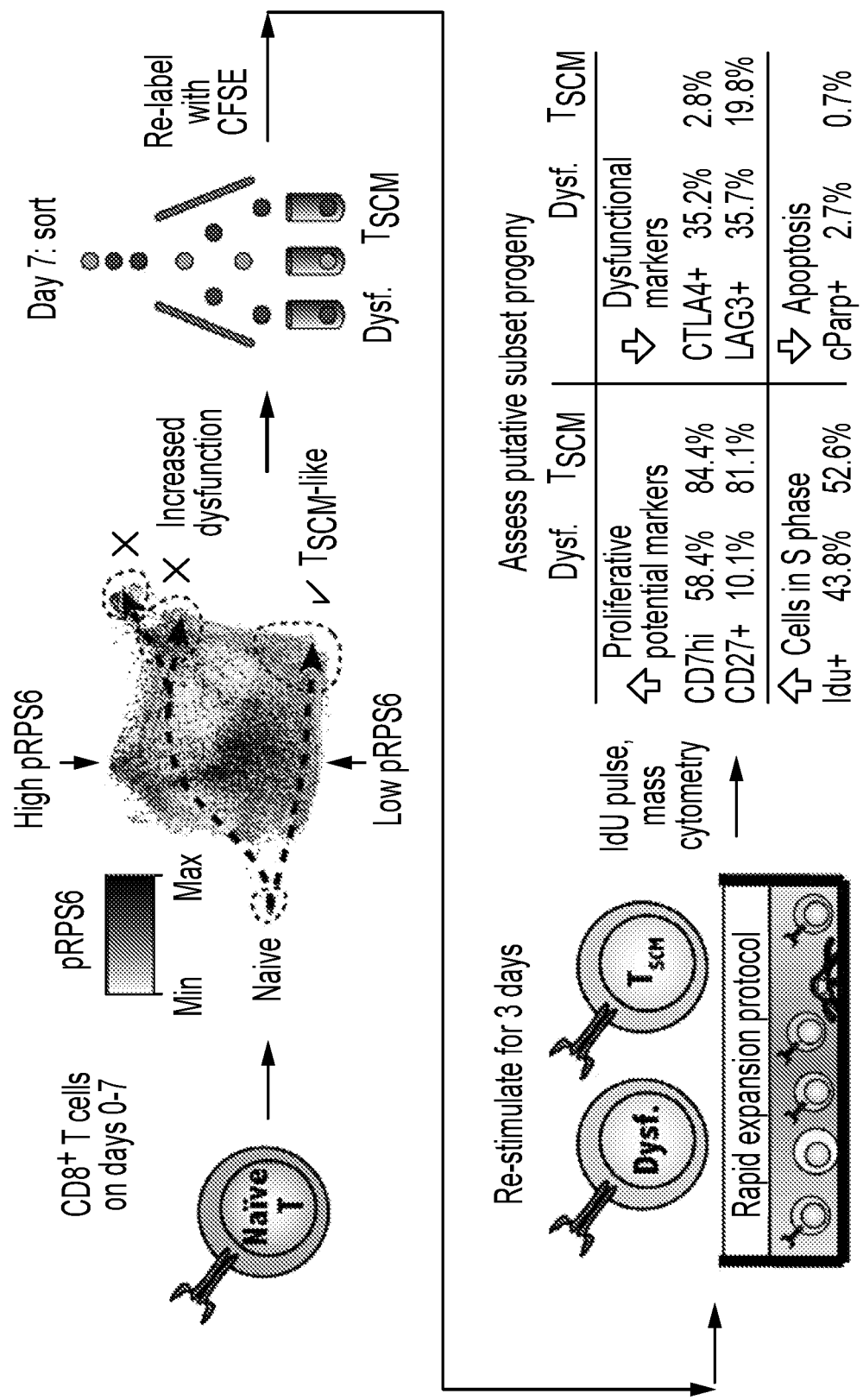
Figures 3, 6B:
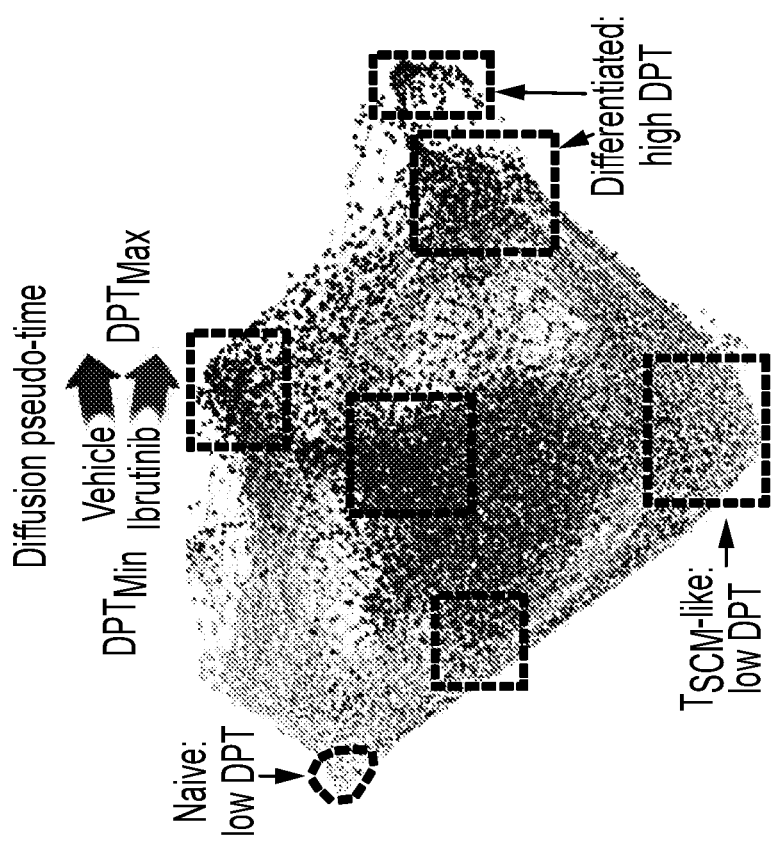
Figure 6C:
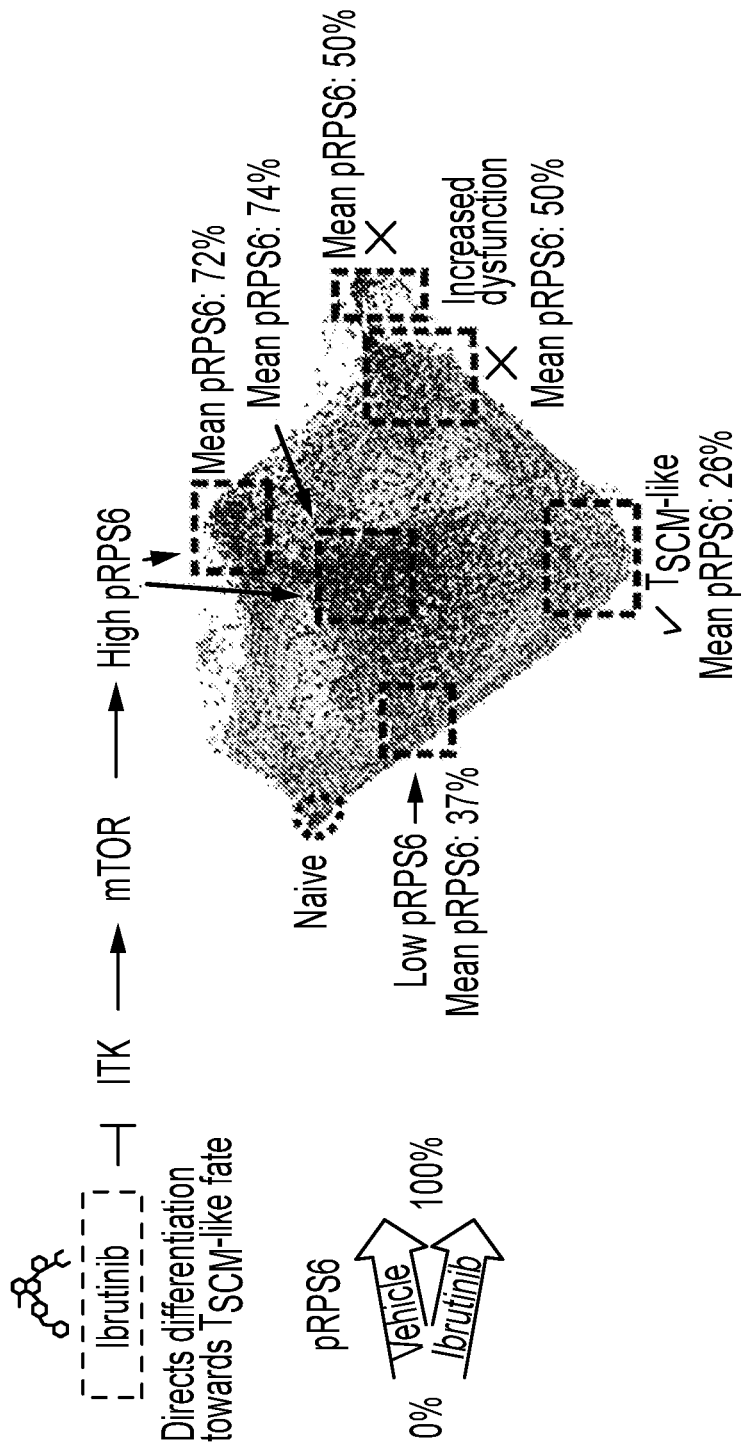
Figure 11C:
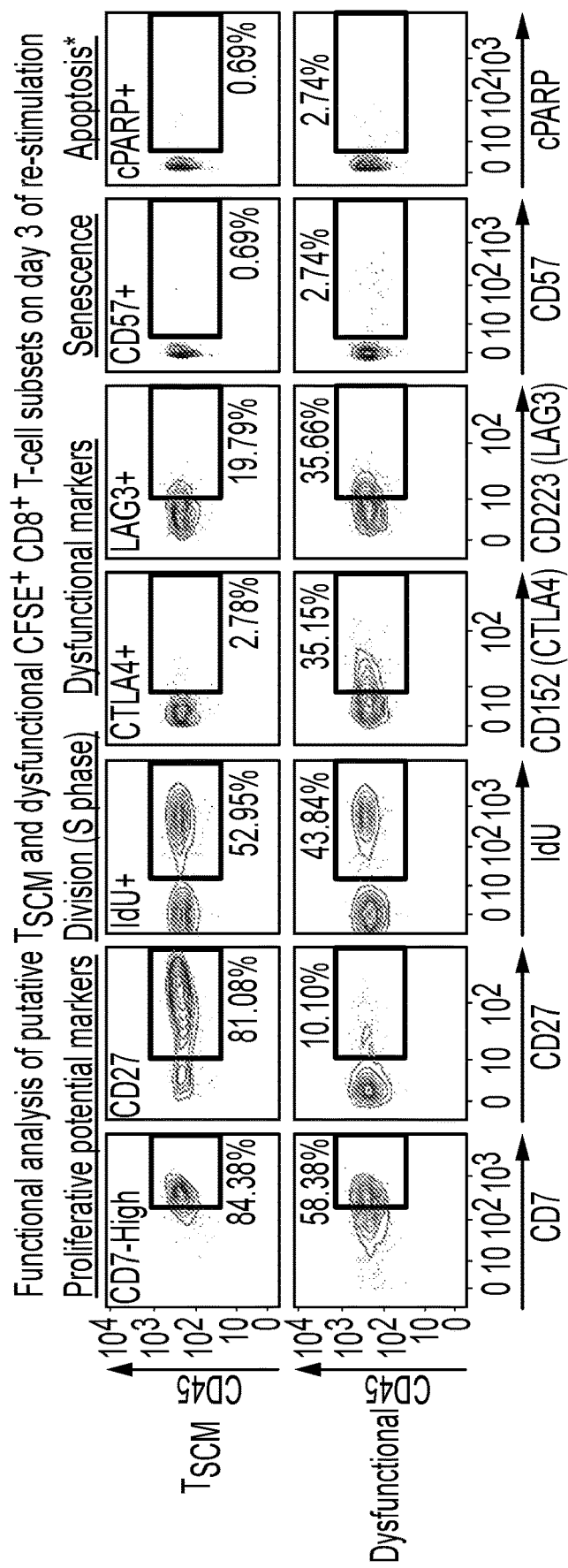

This high-dimensional mass cytometry map allowed to devise a simple fluorescence-activated cell sorting (FACS) scheme to prospectively isolate and test functional properties of our $T_{SCM}$-like and dysfunctional phenotype subsets based on CFSE dilution combined with expression of CD27, CD45RA, and PD1 on day 7 REP CD8+ T cells (FIG. 11). As expected, upon re-stimulation $T_{SCM}$-like cells were superior in their proliferative potential, resistance to apoptosis, and maintenance of beneficial phenotype, such as expression of dysfunctional markers (FIG. 6A, right and FIG. 11). Using intracellular staining, it is further confirmed that $T_{SCM}$-like cells produce more of the proliferation-inducing cytokine IL-2 and less effector cytokines IFN-γ and TNF-α, as expected for $T_{SCM}$-enriched cells in the context of expansion for cancer immunotherapy. While this study is focused on early divergence towards subsets with roles in cancer immunotherapy, $T_{SCM}$ and dysfunctional states could be more distant and not fully represented in our system. Still, given the deep phenotypic definition combined with the multifaceted functional characterization presented here, it is anticipated that the disclosed herein model is a reasonable estimate of the CD8+ T-cell subset potential.

Figure 8A:
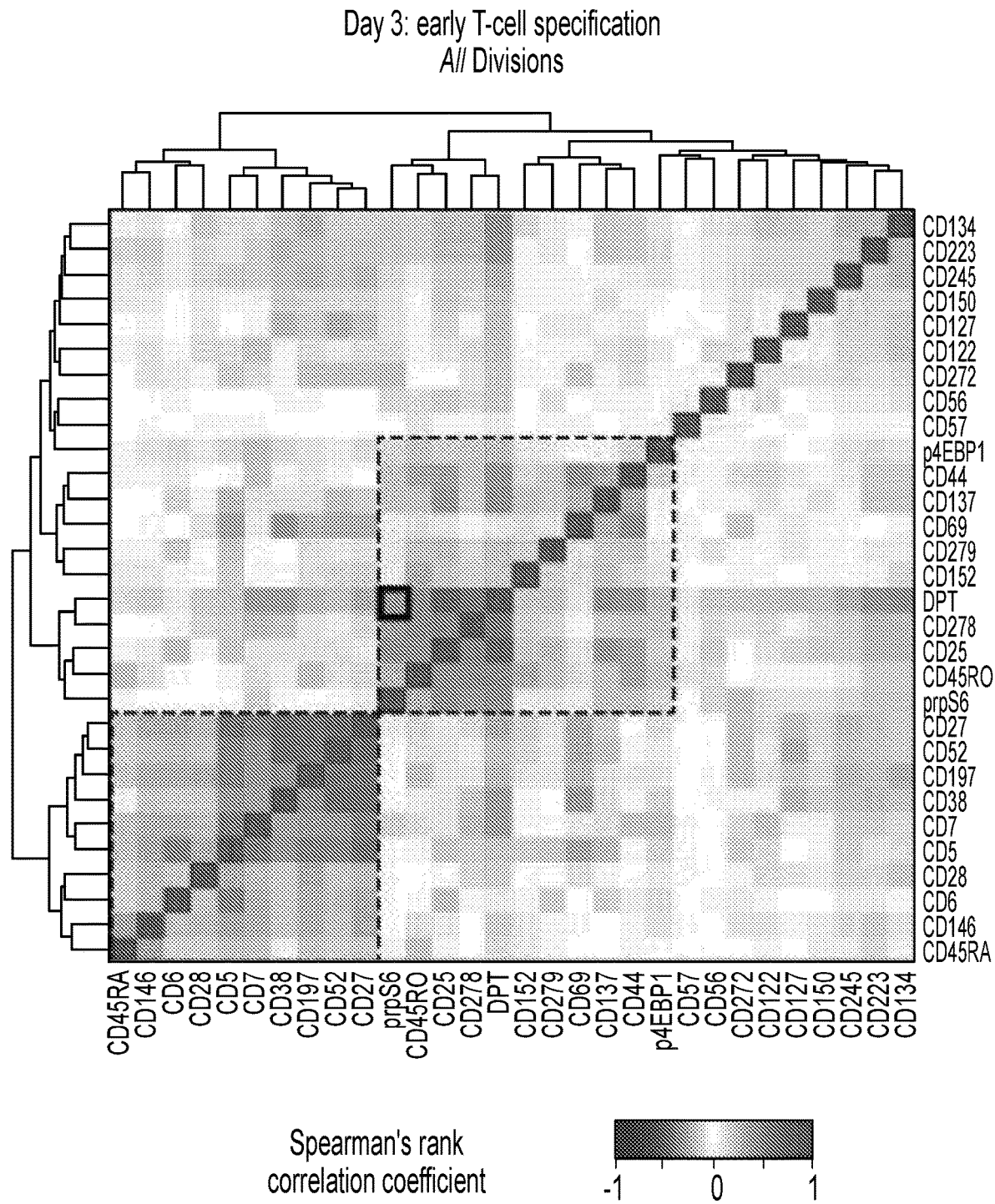
FIG. 8. Single-cell correlation among marker expression and DPT on day 3 of naïve T-cell differentiation. Spearman's rank correlation coefficient was calculated among arsinh-transformed expression of 27 surface proteins, 2 functional markers, and DPT on single CFSE+CD8$^+$ T cells collected on day 3 of naïve T-cell differentiation via REP. This Figure relates to the data presented in FIGS. 6A-6F above.
Figure 8B:
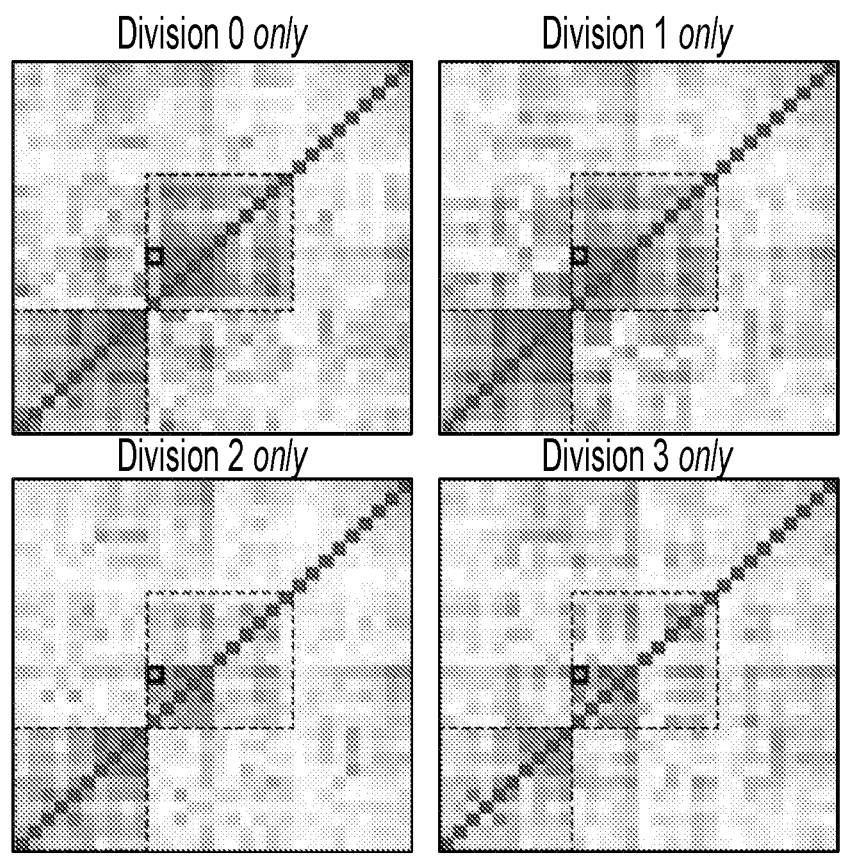

The split between these two CD8+ T-cell fates was also confirmed by DPT analysis, where a minimally differentiated state of $T_{SCM}$-like cells was established as $DPT^{Low}$, and the more differentiated state of dysfunctional phenotype cells was $DPT^{High}$ (FIGS. 6B-1, 6B-2, and 6B-3). Interestingly, DPT was also positively correlated to the mTOR pathway activation markers p4EBP1 and pRPS6 (FIGS. 6A-6B-1, 6B-2, and 6B-3). Notably, pRPS6 was one of the top features correlated with DPT on day 3 of REP, the earliest time point examined (Spearman's rank correlation coefficient to DPT1: 0.72, DPT2: 0.64; Table 6). Further, when correlation analysis was performed within each division state separately, the pattern of T-cell marker correlation changed, but the DPT-pRPS6 connection was maintained irrespective of cell division (FIG. 8). Recalling that pRPS6 had the strongest trend to decrease with time (FIG. 3D), it is hypothesized that interfering with the mTOR pathway directly, or its upstream TCR signaling, during the earliest stages of T-cell activation could skew differentiation towards the minimally differentiated (DPT$^{Low}$) cell state, such as T$_{SCM}$. Without being bound to any theory, it is reasoned that by blocking pRPS6 signaling that is prevalent on a path leading to the increased dysfunction fate during a critical time (e.g., prior to the first division), one would direct naïve T-cell differentiation towards the pRPS6$^{Low}$ path that leads to T$_{SCM}$-like fate (FIG. 6A). Thus naïve T cells were then treated with either ibrutinib, a dual BTK/ITK inhibitor, or rapamycin, an mTOR inhibitor.

Figure 6D:
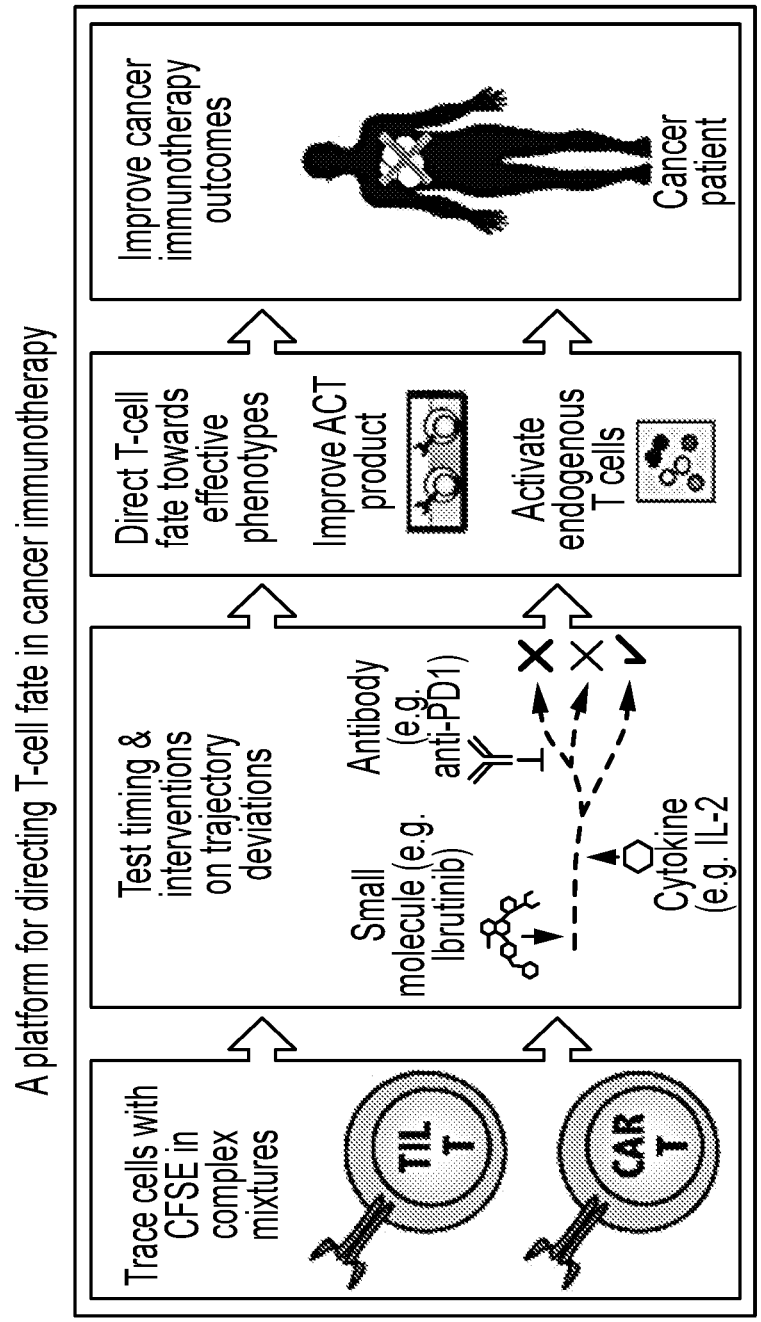

It was observed that ibrutinib skewed T-cell differentiation away from the pRPS6$^{High}$ path terminating at dysfunctional phenotype and towards the pRPS6$^{Low}$ path ending at T$_{SCM}$-like state (FIG. 6A-6D). This reprogramming started early in time (by day 3) and division (all divisions were significantly closer to T$_{SCM}$ phenotype and further from dysfunctional phenotype), and was maintained in the majority of divisions by day 7 (divisions 1-7 were significantly affected) (FIG. 6D-6E). Results were nearly identical when only proteins from the original panel (Table 2) were used instead of the extended panel (Table 4). In contrast to ibrutinib, at the concentration tested rapamycin reduced overall proliferation, subsequently hindering differentiation by locking T cells in a naïve-like CD127$^{++}$ phenotype (FIGS. 6B-1, 6B-2, 6B-3, and 16, and Table 7). As such, it appears that early tuning of TCR and co-receptor signaling during, or prior to, early activation can have pronounced effects on phenotypic output. These results demonstrate that deviations from the reference T-cell specification trajectory can be effectively monitored across time and divisions using our system. Such insights can be used to rationally design timing and type of interventions necessary for guiding differentiation towards desired phenotypes. Our platform is likely to be beneficial for directing T cell fate in ACT, including ex vivo expansion of tumor-infiltrating lymphocytes (TILs) or chimeric antigen receptor (CAR)-engineered T cells, with the goal of improving clinical outcomes for cancer immunotherapy patients.

In light of T-cell engineering for therapeutic application, the ibrutinib-based enhancement of the T$_{SCM}$ phenotype in REP culture was particularly interesting, both because of the simple protocols, and that it could be accomplished entirely ex vivo. Mechanistically, this skewed program started early in time and division, where all divisions were significantly closer to T$_{SCM}$-like subset and further from dysfunctional phenotype on day 3. This pattern was maintained in the majority of divisions by day 7 (divisions 1-7 were significantly affected). If ibrutinib treatment was delayed until day 3, the fate skewing effect was reduced.

Additional data confirmed that ibrutinib had a global effect on naïve CD8+ T-cell expansion, as opposed to selection of a cell subset. By day 7, CFSE-traced CD8+ T cells in the TSCM-like and increased dysfunction regions divided 5-7 times (FIGS. 6B-1, 6B-2, and 6B-3), arguing against expansion of rare clones and indicating that a significant proportion of the initially traced naïve cells contributed to these regions. Apoptosis and cell death in pRPS6+ and pRPS6-fractions were further examined (Table 7). Compared to vehicle control, ibrutinib treatment reduced cell loss in both compartments, whether divided by pRPS6 or cell phenotype. As such, the observed fate skewing effect is due to re-directing a significant proportion of the naïve derived CD8+ cells towards the T$_{SCM}$-like differentiation endpoint and not drug-induced subset selection.

Figure 15A:
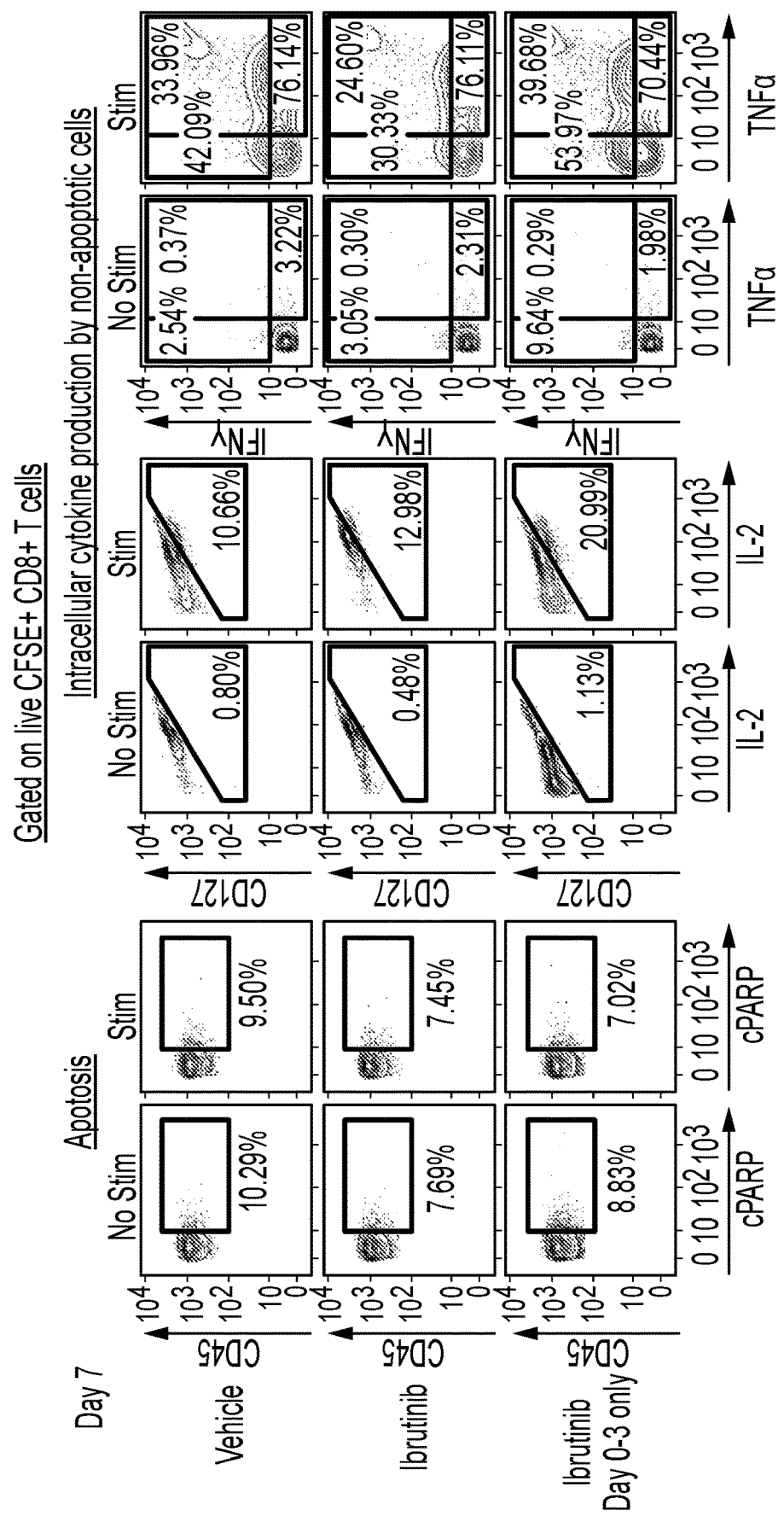
FIGS. 15A-15B depict ibrutinib effect on bulk T-cell intracellular cytokine production and apoptosis. Naïve CFSE+ T cells were treated with (1) vehicle (DMSO) on days 0-7, (2) ibrutinib on days 0-7, or (3) ibrutinib until day 3 only (and vehicle starting on day 3). Next, intracellular production of IL-2, IFN-γ, and TNF-α was assessed by stimulating cells with PMA and ionomycin for 4 hours on either (a) day 7 days of REP culture (FIG. 15A); or (b) after 1 day rest without REP stimulation (with anti-CD3ε antibody and IL-2) and small molecule treatment (FIG. 15B). Cells were stained using an antibody panel in Table 5, examined by mass cytometry, gated on live CFSE+ CD8+ T cells to assess percent of apoptotic (cPARP+) cells, and then gated on non-apoptotic cells to assess intracellular cytokine production.
Figure 15B:
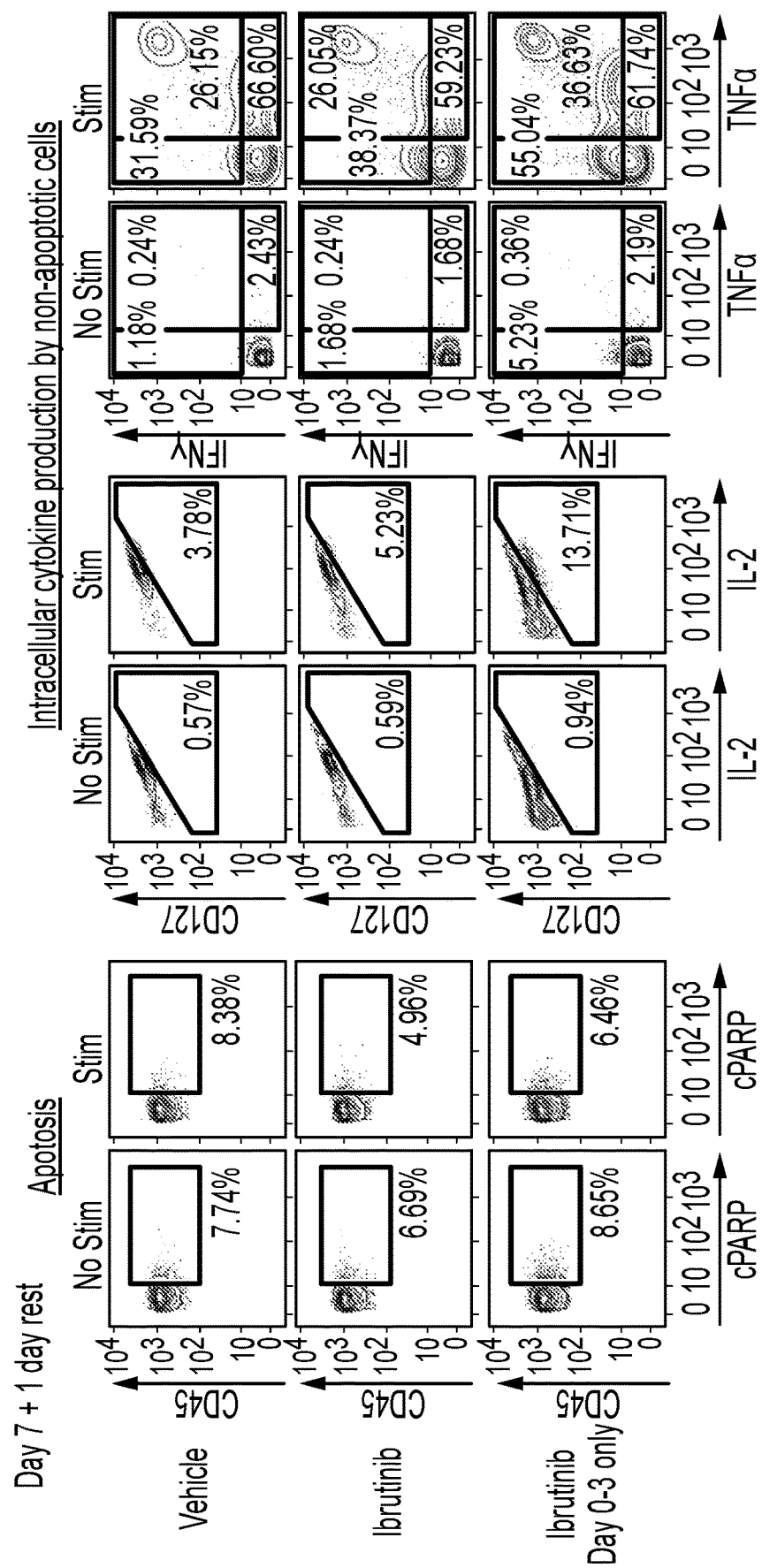
Figure 16A:
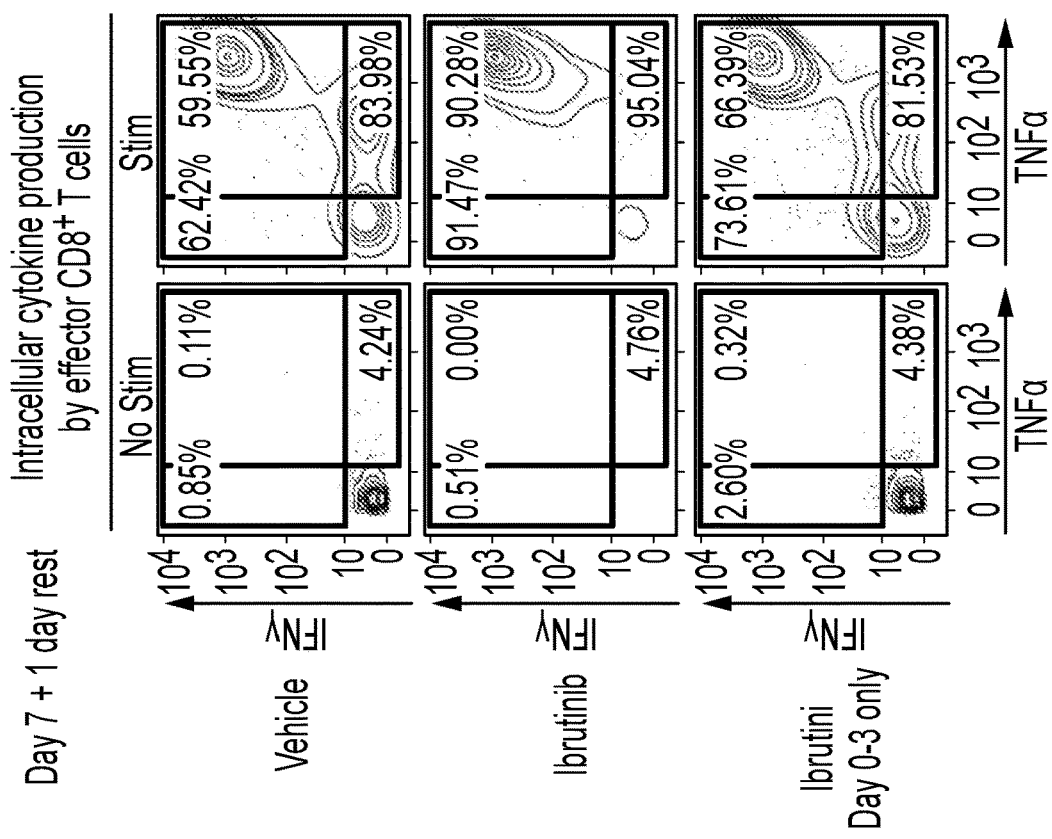
FIGS. 16A-16B depict ibrutinib impact on intracellular IFN-γ and TNF-α production by effector T cells. Naïve CFSE+ T cells were treated with (1) vehicle (DMSO) on days 0-7, (2) ibrutinib on days 0-7, or (3) ibrutinib until day 3 only (and vehicle starting on day 3). Next, intracellular production was assessed by stimulating cells with PMA and ionomycin for 4 hours on either (a) day 7 days of REP culture (FIG. 16A); or (b) after 1 day rest without REP stimulation (with anti-CD3ε antibody and IL-2) and small molecule treatment (FIG. 16B). Cells were stained using an antibody panel in Table 5, examined by mass cytometry, and gated on live nonapoptotic CFSE+ CD8+ effector (CCR7−) T cells to assess intracellular IFN-γ and TNF-α production.
Figure 16B:
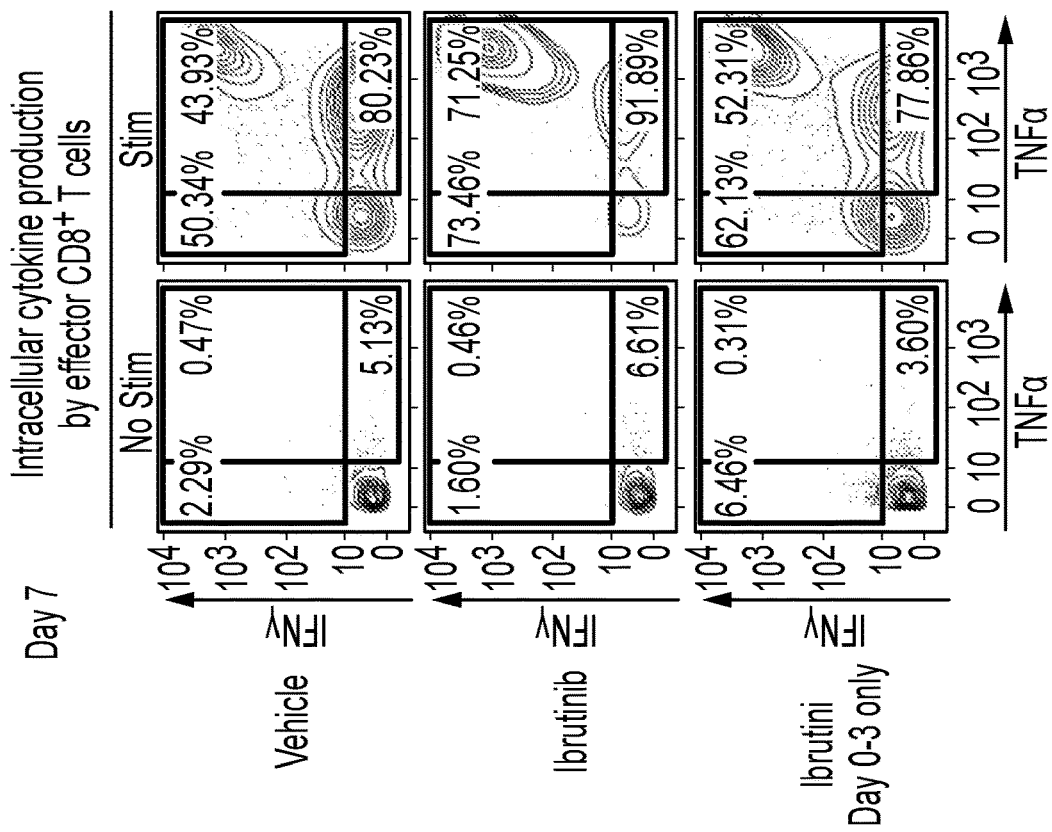
Figure 17A:
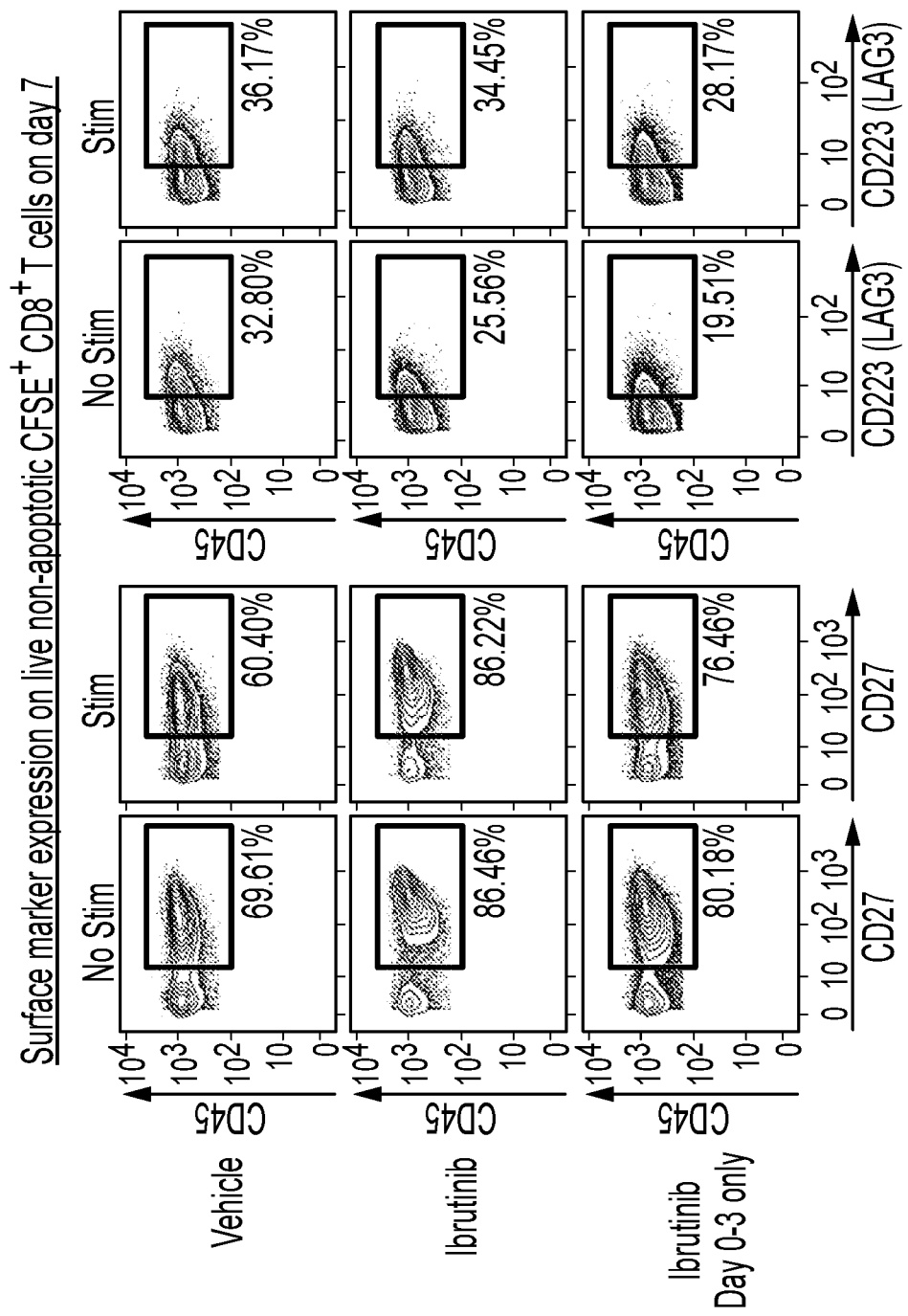
FIG. 17 depicts effect of early ibrutinib treatment on skewing of naïve T-cell differentiation towards $T_{SCM}$-like phenotype. Naïve CFSE+ T cells were treated with (1) vehicle (DMSO) on days 0-7, (2) ibrutinib on days 0-7, or (3) ibrutinib until day 3 only (and vehicle starting on day 3). On day 7 of REP culture, intracellular cytokine production was assessed by stimulating cells with PMA and ionomycin for 4 hours. Cells were analyzed by mass cytometry using an antibody panel in Table 5, and gated on live nonapoptotic CFSE+ CD8+ T cells. Contour plots show expression of a $T_{SCM}$ marker (CD27) and dysfunctional markers (CTLA4 and LAG3) with and without cell stimulation.
Figure 17B:
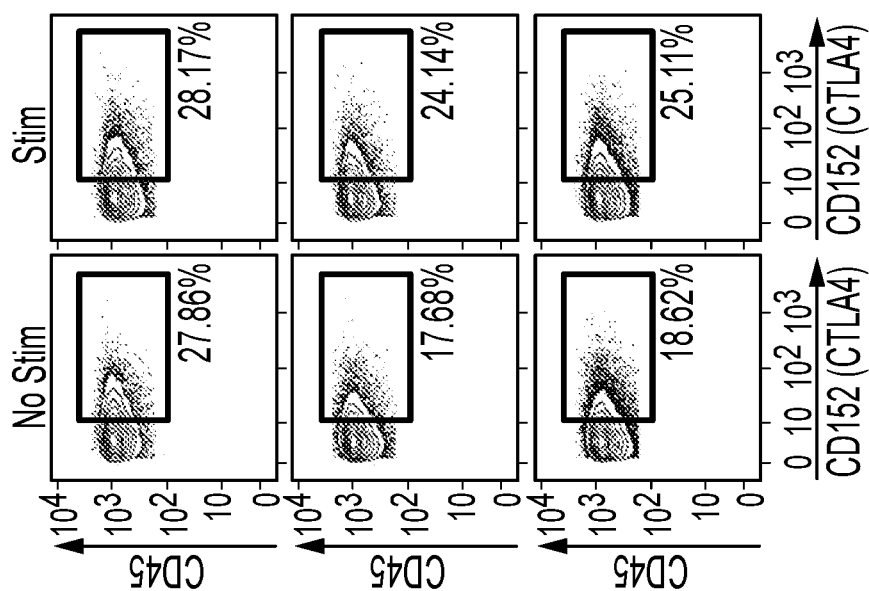

Previously, T$_{SCM}$ subset enrichment in chimeric antigen receptor (CAR)-engineered T cells enhanced intracellular production of IL-2, but not of effector cytokines IFN-γ and TNF-α, when examined in bulk. At the same time, the benefit of TSCM enrichment was enhancement of IFN-γ and TNF-α production by effector (CCR7− CD8+) T cells. Accordingly, here it is observed that ibrutinib enhancement of T$_{SCM}$-like subset improved intracellular IL-2, and not IFN-γ and TNF-α, production in bulk CD8$^+$ T cells (FIG. 15). However, our effector T cells generated in presence of ibrutinib were more potent in IFN-γ and TNF-α production than control effector cells (FIG. 16). Interestingly, adding ibrutinib only before day 3 of REP was sufficient to partially skew cells towards T$_{SCM}$-like fate. Yet, such treatment was also superior for enhancing intracellular production of all 3 cytokines (FIGS. 15 and 17).

TABLE 4

Expanded antibody staining panel for experiments on directing fate of human naïve CFSE+ CD8+ T cells using small molecule inhibitors over REP days 0-7.

| Antibody target and metal | Company | Catalog number | Clone | Isotype | Conjugation & titration | Final concentration |
|---|---|---|---|---|---|---|
| CD45-89Y | Fluidigm | 3089003B | HI30 | Mouse IgG1 | Fluidigm | 1 Test |
| CD235-113In | Biolegend | 306602 | HIR2 | Mouse IgG2b | In-house | 1 pg/mL |
| CD61-113In | BD Biosciences | 555752 | VI-PL2 | Mouse IgG1 | In-house | 2 pg/mL |
| CD44-115In | Biolegend | 103051 | IM7 | Rat IgG2b | In-house | 1 pg/mL |
| CD45RA-139La | Biolegend | 304102 | HI100 | Mouse IgG2b | In-house | 2 pg/mL |
| CD146-140Ce | Biolegend | 342002 | SHM-57 | Mouse IgG2a | In-house | 4 pg/mL |
| cPARP-141Pr* | BD Biosciences | 552597 | F21-852 | Mouse IgG1 | In-house | 1 pg/mL |
| CD28-142Nd | BD Biosciences | 555725 | CD28.2 | Mouse IgG1 | In-house | 2 pg/mL |
| p4EBP1-143Nd* | Cell Sign. Tech. | 2855BF | 236B4 | Rabbit IgG | In-house | 3.5 pg/mL |
| CD5-144Nd | Biolegend | 300602 | UCHT2 | Mouse IgG1 | In-house | 1 pg/mL |
| CD4-145Nd | Fluidigm | 3145001B | RPA-T4 | Mouse IgG1 | Fluidigm | 1 Test |
| CD8a-146Nd | Fluidigm | 3146001B | RPA-T8 | Mouse IgG1 | Fluidigm | 1 Test |
| CD57-147Sm | Biolegend | 322302 | HCD57 | Mouse IgM | In-house | 0.5 pg/mL |
| CD6-148Nd | Fluidigm | 3148013B | BL-CD6 | Mouse IgG1 | Fluidigm | 1 Test |
| CD45RO-149Sm | Biolegend | 304202 | UCHL1 | Mouse IgG2a | In-house | 4 pg/mL |
| CD152-150Nd* | Biolegend | 349916 | L3D10 | Mouse IgG1 | In-house | 7.5 pg/mL |
| CD122-151Eu | Biolegend | 339015 | TU27 | Mouse IgG1 | In-house | 5 pg/mL |

TABLE 4-continued

Expanded antibody staining panel for experiments on directing fate of human
naïve CFSE+ CD8+ T cells using small molecule inhibitors over REP days 0-7.

| Antibody target and metal | Company | Catalog number | Clone | Isotype | Conjugation & titration | Final concentration |
|---|---|---|---|---|---|---|
| TCRyδ-152Sm | Fluidigm | 3152008B | 11F2 | Mouse IgG1 | Fluidigm | 1 Test |
| CD7-153Eu | Fluidigm | 3153014B | CD7-6B7 | Mouse IgG2a | Fluidigm | 1 Test |
| CD278-154Sm | Biolegend | 313502 | C398.4A | Hamster IgG | In-house | 1 pg/mL |
| CD223-155Gd | R&D Systems | AF2319 | Polyclonal | Goat IgG | In-house | 4 pg/mL |
| CD150-156Gd | Biolegend | 306302 | A12(7D4) | Mouse IgG1 | In-house | 2 pg/mL |
| CD134-158Gd | Fluidigm | 3158012B | ACT35 | Mouse IgG1 | Fluidigm | 1 Test |
| CD197-159Tb | Fluidigm | 3159003A | G043H7 | Mouse IgG2a | Fluidigm | 1 Test |
| CD137-160Gd | BD Biosciences | 555955 | 4B4-1 | Mouse IgG1 | In-house | 4 pg/mL |
| CD14-161Dy | BD Biosciences | 555396 | M5E2 | Mouse IgG2a | In-house | 2 pg/mL |
| CD19-161Dy | BD Biosciences | 555410 | HIB19 | Mouse IgG1 | In-house | 0.5 pg/mL |
| CD20-161Dy | BD Biosciences | 555621 | 2H7 | Mouse IgG2b | In-house | 2 pg/mL |
| CD33-161Dy | BD Biosciences | 555449 | WM53 | Mouse IgG1 | In-house | 1 pg/mL |
| CD69-162Dy | Fluidigm | 3162001B | FN50 | Mouse IgG1 | Fluidigm** | 0.5 Test |
| CD272-163Dy | Biolegend | 344502 | MIH2 | Mouse IgG2a | In-house | 5 pg/mL |
| prpS6-164Dy* | BD PhosphoFlow | 624084 | N7-548 | Mouse IgG1 | In-house | 2 pg/mL |
| CD127-165Ho | Fluidigm | 3165008B | A019D5 | Mouse IgG1 | Fluidigm | 1 Test |
| CD52-166Er | Biolegend | 316002 | HI186 | Mouse IgG2b | In-house | 1 pg/mL |
| CD27-167Er | Fluidigm | 3167006B | L128 | Mouse IgG1 | Fluidigm | 1 Test |
| CD38-168Er | Biolegend | 303502 | HIT2 | Mouse IgG1 | In-house | 3 pg/mL |
| CD25-169Tm | Biolegend | 302602 | BC96 | Mouse IgG1 | In-house | 1 pg/mL |
| CD3E-170Er | Fluidigm | 3170001B | UCHT1 | Mouse IgG1 | In-house | 1 Test |
| FITC-172Yb* | Southern Biotech | 6400-01 | Polyclonal | Sheep IgG | In-house | 8 pg/mL |
| CD279-175Lu | Fluidigm | 3175008B | EH12.2H7 | Mouse IgG1 | Fluidigm | 1 Test |
| CD56-176Yb | Fluidigm | 3176008B | NCAM16.2 | Mouse IgG1 | Fluidigm | 1 Test | cPARP, cleaved PARP; prpS6, phosphorylated ribosomal protein S6. Related to FIG. 6.
*These antibodies were used for intracellular staining (post-methanol). Remaining antibodies were used during surface staining (prior to methanol permeabilization).
**Recommended concentrations were adjusted based on in-house titration results.

The origin of $T_{SCM}$ cells is currently of great interest in both immunology and cancer immunotherapy. Our observation that $T_{SCM}$ phenotype cells arise by day 7 of naïve CD8+ T-cell differentiation is consistent with individual marker expression in REP cultures. The data suggest that in the context of REP, $T_{SCM}$ phenotype cells may arise from a subpopulation with the lowest DPT values on days 3-5. These cells had low mTOR pathway activity (prpS6), long proliferative history, remained CD45RA$^{High}$ CD45RO$^{Low}$, and had CD25$^{Low}$ CD27$^{High}$ CD38$^{High}$CD44$^{Low}$ CD52$^{High}$ CD69$^{Low}$ CCR7$^{High}$ phenotype (CD27 and CCR7 were expressed much higher than on naïve cells).

Directing CAR T and TILs towards $T_{SCM}$ fate is an important direction in cancer immunotherapy, exemplified by a recent protocol for generating CD19-CAR $T_{SCM}$ cells. By understanding how T cells transition through phenotypic space across time and divisions, an intervention is selected to modulate our system for therapeutic purposes. It was observed that ibrutinib directed T-cell fate away from dysfunctional and towards $T_{SCM}$ phenotype. In contrast to rapamycin that halted mTOR signaling, ibrutinib-treated cells activated rpS6 by day 5, yet continued advancing towards $T_{SCM}$ phenotype on days 5-7, suggesting that early signaling events may be key in $T_{SCM}$ fate selection. Our results may also help explain the recently observed $T_{SCM}$ expansion in patients with chronic lymphocytic leukemia (CLL) receiving ibrutinib, as well as the improvement in CAR T efficacy when administered after or with ibrutinib for treatment of CLL in the clinic. It would also be interesting to examine whether observed improvement in CD8+ T-cell memory responses after blocking either mTOR39 or ITK43 signaling in vivo were in part due to an expansion of $T_{SCM}$ cells. Going forward, this platform will be used in future lymphocyte-engineering studies to direct fate of TILs or CAR T cells towards $T_{SCM}$ phenotype. The concepts generated by the studies could later be applied to guiding T-cell fate in situ by systemic treatment of cancer immunotherapy patients, with the goal of improving their clinical outcomes (FIG. 6F).

Our results demonstrated that deviations from the reference T-cell differentiation trajectory can be effectively monitored across time and division states using our system. These can be used to rationally design timing and type of interventions necessary for guiding differentiation towards desired phenotypes. Here, ibrutinib was selected to direct naïve T-cell fate away from the increased dysfunction state and towards the T $T_{SCM}$-like state. Importantly, the early divergence of T-cell fate following activation, which appears to be linked to regulatory signaling downstream of TCR, highlights the important role that immune receptor engagement has on dictating downstream cell function. While ibrutinib, which presumably inhibits ITK downstream of the cross-linked TCR, reduced the proportion of pRPS6$^{High}$ cells and enhanced the expansion into our $T_{SCM}$-like cell compartment, one cannot rule out indirect effects of the inhibitor as well. In REP culture, ibrutinib could also affect antigen-presenting cells (APCs), such as monocytes and most likely B cells, through the inhibition of BTK. In particular, this could change interactions of naïve CD8+ T cells with APCs early in REP, when the APCs are still relatively abundant.

In addition, our data suggest that in the context of REP, $T_{SCM}$-like cells may arise from a subpopulation with low mTOR pathway activity (pRPS6) and associated cell surface protein expression on day 3 of activation (region marked 'CD45RA$^{High}$' in FIGS. 6B-1, 6B-2, 6B-3, and 6C; these cells are CD45RO$^{Low}$ CD25$^{Low}$ CD38$^{Low}$ CD69$^{High}$ CD137$^{Low}$). Granted that a limited amount of co-stimulatory signaling is necessary for T-cell memory formation, our data are consistent with prior observations that CD25$^{High}$ CD8+

T cells activate strong IL-2-induced transcriptional programs and give rise to terminally differentiated and short-lived effector cells that are prone to apoptosis, whereas CD25Low cells eventually give rise to functional long-lived memory cells. Going forward, our platform would be appropriate to follow fate of cells in the 'CD45RA$^{High}$' region after sorting and re-labeling with CFSE, and to attempt the identification of potential $T_{SCM}$ precursors during normal T-cell differentiation in a mouse model of infection or cancer.

Example 11: Benefit of Ibrutinib on Phenotype and Function of CD19-Targeted CAR T Cells In Vitro This Example describes experiments performed to assess the benefit of ibrutinib on phenotype and function of CD19-targeted CAR T cells in vitro. In these experiments, CD19-targeted chimeric antigen receptor (CAR) T cells with 2 different co-stimulation domains are cultured with ibrutinib for 10 days to assess surface marker expression by flow cytometry. The cells are then rested for 1 day without inhibitors and assessed for various function, including (1) killing of CD19-expressing Nalm6 leukemia cell line quantified via incucyte assay, and (2) secretion of IFN-γ and IL-2 cytokines by ELISA after 24 h co-culture with Nalm6 cells The following specimens are used in these experiments: (1) Mock T cells (control), (2) CD19.28z CAR T cells containing transmembrane and intracellular domain from CD28, as well as intracellular domain from CD3ζ, (3) CD19.BBz CAR T cells containing transmembrane domain from CD8α and intracellular domain from 4-1BB, as well as intracellular domain from CD3ζ. CAR T cells are prepared according to standard protocols. Briefly, T cells are enriched from healthy donor peripheral blood mononuclear cells (PBMCs) and activated to proliferate using beads coated with antibodies against CD3 and CD28. The cells are engineered using retroviral transduction techniques to deliver DNA constructs encoding each of the above-mentioned CARs on days 2 and 3, and the beads are then removed on day 4. Further information regarding the protocol can be found in, e.g., Mount and Majzner et al. Nature Medicine (2018).

The following conditions are used in these experiments: (1) Vehicle (DMSO; control); (2) ibrutinib (continuous: 1.6 µM on days 0-2, 0.32 µM on days 3-10); (3) ibrutinib (early: 1.6 µM on days 0-2, 0.32 µM on days 3-6, DMSO on days 7-10); and (4) ibrutinib (very early: 1.6 µM on days 0-2, DMSO on days 3-10).

Without being bound to any particular theory, it is expected that ibrutinib treatment facilitates CAR T cell memory formation (as measured by flow cytometry), and augments both the killing capacity and cytokine secretion of CD19 CAR T cells in response to Nalm6 leukemia.

Example 12: Efficacy of CD19-Targeted CAR T Cells Expanded in the Presence of Ibrutinib In Vivo This Example describes experiments performed to assess the efficacy of CD19-targeted CAR T cells expanded in the presence of ibrutinib in vivo. In these experiments, a 'stress test' model is used, where immunodeficient (NSG) mice receive a suboptimal dose of CD19-targeted CAR T cells (e.g., 1 million) that is not sufficient to cure CD19-expressing Nalm6 leukemia cells (1 million cells engrafted 7 days prior). Without being bound to any particular theory, this approach enables to assess the benefit of improvement to the current design and potentially improve CAR T cell efficacy in patients. It is expected that CAR T cells expanded in the presence of ibrutinib more effectively suppress tumor outgrowth compared to those expanded in vehicle (DMSO).

In these experiments, the Nalm6 leukemia cells stably express luciferase and GFP to allow for quantification of tumor burden via bioluminescence imaging and flow cytometry. The following conditions are used: (1) Mock T cells (control); (2) CD19.BBz CAR T cells expanded in vehicle (DMSO); (3) CD19.BBz CAR T cells expanded in continuous ibrutinib as described above; n=5 per group.

While preferred embodiments of the disclosures have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 5

Expanded antibody staining panel for experiments on directing fate of human naïve CFSE+ CD8+ T cells using small molecule inhibitors over REP days 0-7.

| Antibody target and metal | Company | Catalog Number | Clone | Isotype | Conjugation & titration | Final concentration |
|---|---|---|---|---|---|---|
| CD45-89Y | Fluidigm | 3089003B | H130 | Mouse IgG1 | Fluidigm | 1 Test |
| CD235-113In | Biolegend | 306602 | HIR2 | Mouse IgG2b | In-house | 1 g/mL |
| CD61-113In | BD Biosciences | 555752 | VI-PL2 | Mouse IgG1 | In-house | 2 g/mL |
| CD44-115In | Biolegend | 103051 | IM7 | Rat IgG2b | In-house | 1 g/mL |
| CD45RA-139La | Biolegend | 304102 | HI100 | Mouse IgG2b | In-house | 2 g/mL |
| CD146-140Ce | Biolegend | 342602 | SHM-57 | Mouse IgG2a | In-house | 4 g/mL |
| cPARP-141Pr* | BD Biosciences | 552597 | F21-852 | Mouse IgG1 | In-house | 1 g/mL |
| CD11a-142Nd | Biolegend | 301202 | HI111 | Mouse IgG1 | In-house | 3 g/mL |
| CD28-143Nd | Biolegend | 302914 | CD28.2 | Mouse IgG1 | In-house | 4 g/mL |
| CD38-144Nd | Fluidigm | 3144014B | HIT2 | Mouse IgG1 | Fluidigm | 1 Test |
| CD4-145Nd | Fluidigm | 3145001B | RPA-T4 | Mouse IgG1 | Fluidigm | 1 Test |
| CD8α-146Nd | Fluidigm | 3146001B | RPA-T8 | Mouse IgG1 | Fluidigm | 1 Test |
| CD57-147Sm | Biolegend | 322302 | HCD57 | Mouse IgM | In-house | 0.5 g/mL |
| CD6-148Nd | Fluidigm | 3148013B | BL-CD6 | Mouse IgG1 | Fluidigm | 1 Test |
| CD45RO-149Sm | Fluidigm | 3149001B | UCHL1 | Mouse IgG2a | Fluidigm | 1 Test |
| CD152-150Nd* | Biolegend | 349916 | L3D10 | Mouse IgG1 | In-house | 7.5 g/mL |

TABLE 5-continued

Expanded antibody staining panel for experiments on directing fate of human naïve CFSE+ CD8+ T cells using small molecule inhibitors over REP days 0-7.

| Antibody target and metal | Company | Catalog Number | Clone | Isotype | Conjugation & titration | Final concentration |
|---|---|---|---|---|---|---|
| CD122-151Eu | Biolegend | 339015 | TU27 | Mouse IgG1 | In-house | 5 q/mL |
| TCRyδ-152Sm | Fluidigm | 3152008B | 11F2 | Mouse IgG1 | Fluidigm | 1 Test |
| CD7-153Eu | Fluidigm | 3153014B | CD7-6B7 | Mouse IgG2a | Fluidigm | 1 Test |
| CD278-154Sm | Biolegend | 313502 | C398.4A | Hamster IgG | In-house | 2 g/mL |
| CD223-155Gd | R&D Systems | AF2319 | Polyclonal | Goat IgG | In-house | 4 g/mL |
| CD183-156Gd | Fluidigm | 3156004B | G025H7 | Mouse IgG1 | Fluidigm | 1 Test |
| CD245-157Gd | Biolegend | 334402 | DY12 | Mouse IgG1 | In-house | 5 g/mL |
| CD134-158Gd | Fluidigm | 3158012B | ACT35 | Mouse IgG1 | Fluidigm** | 2 Tests |
| CD197-159Tb | Fluidigm | 3159003A | G043H7 | Mouse IgG2a | Fluidigm** | 2 Tests |
| CD137-160Gd | BD Biosciences | 555955 | 4134-1 | Mouse IgG1 | In-house | 4 g/mL |
| CD14-161Dy | BD Biosciences | 555396 | M5E2 | Mouse IgG2a | In-house | 2 g/mL |
| CD19-161Dy | BD Biosciences | 555410 | HIB19 | Mouse IgG1 | In-house | 1 g/mL |
| CD20-161Dy | BD Biosciences | 555621 | 2H7 | Mouse IgG2b | In-house | 2 g/mL |
| CD33-161Dy | BD Biosciences | 555449 | WM53 | Mouse IgG1 | In-house | 1 g/mL |
| CD69-162Dy | Fluidigm | 31620016 | FN50 | Mouse IgG1 | Fluidigm** | 0.5 Test |
| TNFα-163Dy* | Biolegend | 502901 | MAb11 | Mouse IgG | In-house | 2 g/mL |
| CD95-164Dy | Fluidigm | 3164008B | DX2 | Mouse IgG1 | Fluidigm** | 2 Tests |
| CD127-165Ho | Fluidigm | 3165008B | A019D5 | Mouse IgG1 | Fluidigm** | 2 Tests |
| IL2-166Er* | Fluidigm | 3166002B | MQ1-17H12 | Rat IgG2a | Fluidigm | 1 Test |
| CD27-167Er | Fluidigm | 31670066 | L128 | Mouse IgG1 | Fluidigm | 1 Test |
| IFNy-168Er* | Fluidigm | 3168005B | B27 | Mouse IgG1 | Fluidigm | 1 Test |
| CD25-169Tm | Biolegend | 302602 | BC96 | Mouse IgG1 | In-house | 1 g/mL |
| CD3ε-170Er | Fluidigm | 31700016 | UCHT1 | Mouse IgG1 | Fluidigm** | 2 Tests |
| FITC-172Yb* | Southern Biotech | 6400-01 | Polyclonal | Sheep IgG | In-house | 16 g/mL |
| CD279-175Lu | Fluidigm | 31750086 | EH12.2H7 | Mouse IgG1 | Fluidigm** | 2 Tests |
| CD58-176Yb | Fluidigm | 31760176 | TS2/9 | Mouse IgG1 | Fluidigm** | 2 Tests |
| pRPS6-209Bi* | BD PhosphoFlow | 560433 | N7-548 | Mouse IgG1 | In-house | 2 g/mL | cPARP, cleaved PARP; pRPS6, phosphorylated ribosomal protein S6 (pS235/236).
This antibody panel was used to generate data for FIGS. 14 and 15-17.
*These antibodies were used for intracellular staining (post-methanol). Remaining antibodies were used during surface staining (prior to methanol permeabilization).
**Recommended concentrations were adjusted based on in-house titration results.

TABLE 6

Predictive lasso coefficients and correlation coefficients for DPT1 and DPT2 in naïve T-cell differentiation on day 3 of REP.

| Name | Alias | Coefficient (DPT1) | Correlation (DPT1) | Coefficient (DPT2) | Correlation (DPT2) |
|---|---|---|---|---|---|
| CD3ε | | NA | 0.579951616 | NA | 0.480890421 |
| CD8α | | NA | 0.608354089 | NA | 0.516986583 |
| CD45 | PTPRC | NA | 0.565415049 | NA | 0.510838055 |
| CD45RA | | −0.005754538 | 0.139759482 | −0.002034742 | 0.141754074 |
| CD45RO | | 0.00273804 | 0.442649016 | 0.001941521 | 0.387503167 |
| CD95 | FAS | 0.006962264 | 0.574683676 | 0.002475872 | 0.487901948 |
| CD127 | IL7Ra | −0.001302581 | 0.433725998 | −0.001434864 | 0.373487378 |
| CD197 | CCR7 | −0.000995324 | 0.328136591 | −0.00341218 | 0.256464262 |
| CO25 | I L2Ra | 0.073173286 | 0.868175998 | 0.074630946 | 0.765065249 |
| CD38 | ADPRC1 | 0.047249373 | 0.552118076 | 0.029508861 | 0.491177566 |
| CD69 | | 0.013244034 | 0.090421288 | 0.009773978 | 0.150104989 |
| CD183 | CXCR3 | 0.027040402 | 0.66396105 | 0.022980671 | 0.562724652 |
| CD7 | | 0.00432812 | 0.594435332 | 0.00031486 | 0.491600021 |
| CD27 | | 0.003393761 | 0.682218896 | 0.008129403 | 0.637464711 |
| CD28 | | 0.005951581 | 0.399060074 | 0.002069433 | 0.361930526 |
| CD134 | OX40 | 0.004264069 | 0.474010263 | 0.004405973 | 0.46542505 |
| C0137 | 4-IBB | 0.037415795 | 0.592418519 | 0.094613705 | 0.726790688 |
| CD278 | ICOS | 0.010142023 | 0.654076733 | 0.003183394 | 0.550228558 |
| CD150 | SLAMF1 | 0 | 0.352960211 | −1.43E-05 | 0.33098942 |
| CD223 | LAG3 | 0.003232165 | 0.607660671 | 0.002734663 | 0.546042218 |
| CD272 | BTLA | −0.001845931 | 0.28375831 | −0.002647317 | 0.228440265 |
| CD279 | PD1 | 0.002210133 | 0.564524481 | 0.003901794 | 0.505669356 |
| CD366 | TIM3 | 0.003630764 | 0.480003481 | 0.003605168 | 0.439035806 |
| CD57 | HNK1 | −0.003261835 | 0.355343446 | −0.003350716 | 0.295355101 |

TABLE 6-continued

Predictive lasso coefficients and correlation coefficients for DPT1 and DPT2 in naïve T-cell differentiation on day 3 of REP.

| Name | Alias | Coefficient (DPT1) | Correlation (DPT1) | Coefficient (DPT2) | Correlation (DPT2) |
|---|---|---|---|---|---|
| Ki-67 | | −0.002577621 | 0.570240939 | −0.001548349 | 0.501808956 |
| pRPS6 | | −0.006527334 | 0.715235641 | −0.008286249 | 0.635583061 |

This table is related to Fig. 5A.

*Lasso models were fit using 5-fold cross-validation on training data (80% of cells), and then applied to test data (20% of cells) to assess the accuracy of model performance. Mean errors were: 4.5% (train) and 4.6% (test) for DPT1, 4.3% (train) and 4.3% (test) for DPT2. Protein markers with the highest (by absolute value) lasso coefficients for DPT prediction and their Spearman correlation to DPT are highlighted in bold. For both DPT1 and DPT2, top 3 predictive coefficients were for CD25, CD38, and CD137.

TABLE 7

Effects of ibrutinib and rapamycin on total cell counts and fractions on apoptotic or dead cells during naïve T-cell differentiation in REP.

| Treatment | Day | Total cells (×10$^6$) | CFSE$^+$ CD8$^+$ T cells (%)* | Total CFSE$^+$ CD8$^+$ T cells | Apoptotic cells (% cPARP$^+$ cells in CFSE$^+$ CD8$^+$T cells | Dead cells (1% cisplatin$^+$ cells in CFSE$^+$ CD8$^+$ T cells |
|---|---|---|---|---|---|---|
| — | 0 | 13.58 | 0.35 | 0.05 | 0.00 | 0.00 |
| Vehicle | 3 | 5.70 | 4.03 | 0.23 | 5.21 | 0.65 |
| Ibrutinib | 3 | 5.24 | 1.31 | 0.07 | 0.17 | 0.17 |
| Rapamycin | 3 | 6.48 | 2.14 | 0.14 | 0.43 | 0.26 |
| Vehicle | 4 | 8.30 | 9.76 | 0.81 | 3.63 | 0.95 |
| Ibrutinib | 4 | 4.98 | 1.57 | 0.08 | 0.45 | 0.76 |
| Rapamycin | 4 | 9.96 | 3.07 | 0.31 | 0.85 | 0.38 |
| Vehicle | 5 | 12.45 | 23.07 | 2.87 | 5.04 | 1.07 |
| Ibrutinib | 5 | 14.58 | 3.62 | 0.53 | 3.10 | 0.58 |
| Rapamycin | 5 | 13.91 | 5.14 | 0.71 | 1.07 | 0.21 |
| Vehicle | 7 | 35.15 | 16.25 | 5.71 | 4.57 | 4.75 |
| Ibrutinib | 7 | 75.09 | 11.37 | 8.53 | 3.53 | 0.88 |
| Rapamycin | 7 | 28.03 | 6.49 | 1.82 | 2.16 | 1.13 |

(Continued) Gated on CFSE$^+$CD8$^+$T cells

| Treatment | Day | CD45RA$^{High}$ CD25$^{Low}$ (%) | Apoptotic Cell (%) | Dead cells (%) | CD45RA$^{Low}$ CD25$^{High}$ (%) | Apoptotic Cells (%) | Dead cells (%) |
|---|---|---|---|---|---|---|---|
| — | 0 | 28.63 | 0.00 | 0.00 | 0.00 | NA | NA |
| Vehicle | 3 | 13.98 | 5.50 | 0.17 | 35.85 | 5.02 | 0.87 |
| Ibrutinib | 3 | 38.49 | 0.44 | 0.00 | 1.68 | 0.00 | 0.00 |
| Rapamycin | 3 | 16.11 | 0.53 | 0.00 | 27.34 | 0.31 | 0.63 |
| Vehicle | 4 | 14.93 | 4.49 | 1.19 | 25.56 | 3.61 | 0.64 |
| Ibrutinib | 4 | 32.02 | 0.47 | 0.00 | 6.95 | 0.00 | 0.00 |
| Rapamycin | 4 | 16.03 | 0.59 | 0.39 | 30.19 | 0.84 | 0.21 |
| Vehicle | 5 | 13.92 | 5.88 | 0.31 | 26.56 | 6.12 | 1.42 |
| Ibrutinib | 5 | 39.72 | 2.94 | 0.18 | 13.00 | 3.65 | 0.28 |
| Rapamycin | 5 | 8.87 | 2.33 | 0.00 | 43.80 | 0.79 | 0.24 |
| Vehicle | 7 | 13.96 | 8.06 | 1.48 | 6.96 | 4.43 | 5.10 |
| Ibrutinib | 7 | 31.67 | 5.43 | 0.22 | 6.73 | 2.86 | 2.67 |
| Rapamycin | 7 | 9.00 | 3.47 | 0.69 | 21.79 | 1.15 | 0.72 |

(Continued) Gated on CFSE$^+$CD8$^+$T cells

| Treatment | Day | pRPS6$^+$ (%) | Apoptotic cells (%) | Dead cells (%) | pRPS6$^+$ (%) | Apoptotic cells (%) | Dead cells (%) |
|---|---|---|---|---|---|---|---|
| — | 0 | 99.59 | 0.00 | 0.00 | 0.41 | 0.00 | 0.00 |
| Vehicle | 3 | 71.61 | 4.39 | 0.67 | 28.39 | 7.28 | 0.59 |
| Ibrutinib | 3 | 96.64 | 0.17 | 0.17 | 3.36 | 0.00 | 0.00 |
| Rapamycin | 3 | 99.49 | 0.43 | 0.26 | 0.51 | 0.00 | 0.00 |
| Vehicle | 4 | 63.24 | 3.08 | 1.06 | 36.76 | 4.57 | 0.76 |
| Ibrutinib | 4 | 86.25 | 0.53 | 0.53 | 13.75 | 0.00 | 2.20 |
| Rapamycin | 4 | 99.15 | 0.86 | 0.38 | 0.85 | 0.00 | 0.00 |
| Vehicle | 5 | 79.00 | 4.36 | 1.26 | 21.00 | 7.62 | 0.35 |
| Ibrutinib | 5 | 66.56 | 1.81 | 0.49 | 33.44 | 5.68 | 0.76 |
| Rapamycin | 5 | 99.28 | 1.04 | 0.21 | 0.72 | 4.76 | 0.00 |
| Vehicle | 7 | 93.93 | 4.42 | 4.99 | 6.07 | 6.91 | 1.07 |

TABLE 7-continued

Effects of ibrutinib and rapamycin on total cell counts and fractions on apoptotic or dead cells during naïve T-cell differentiation in REP.

| Ibrutinib | 7 | 91.71 | 3.30 | 0.90 | 8.29 | 5.96 | 0.62 |
| Rapamycin | 7 | 99.44 | 2.14 | 1.13 | 0.56 | 5.56 | 0.00 |

Cell viability was >90% in all samples based on trypan blue counts. CFSE+ CD8+ T cells cells on the path toward dysfunctional phenotype were gated as either $CD45RA^{Low}\ CD5^{High}$ or $pRPS6^+$, whereas cells on the path towards $T_{SCM}$-like phenotype were $CD45RA^{High}\ CD25^{Low}$ or pRPS6-(these gates are most relevant on day 3 and possibly 4).

*Live (cisplatin-) and non-apoptotic (cPARP-) gates were not applied here (unlike throughout the manuscript) in order to assess fractions of apoptotic and dead cells among CFSE+ CD8+ T cells and its subpopulations.

TABLE 8

Adjusted mass cytometry antibody staining panel for experiments on directing fate of human naïve CFSE+ CD8+ T cells using ibrutinib over REP days 0-7.

| Treatment | Day | Total cells ($\times 10^6$) | $CFSE^+$ $CD8^+$ T cells (%)* | Total $CFSE^+$ $CD8^+$ T cells | Apoptotic cells (% $cPARP^+$ cells in $CFSE^+$ $CD8^+$ T cells | Dead cells (1% $cisplatin^+$ cells in $CFSE^+$ $CD8^+$ T cells |
|---|---|---|---|---|---|---|
| — | 0 | 13.58 | 0.35 | 0.05 | 0.00 | 0.00 |
| Vehicle | 3 | 5.70 | 4.03 | 0.23 | 5.21 | 0.65 |
| Ibrutinib | 3 | 5.24 | 1.31 | 0.07 | 0.17 | 0.17 |
| Rapamycin | 3 | 6.48 | 2.14 | 0.14 | 0.43 | 0.26 |
| Vehicle | 4 | 8.30 | 9.76 | 0.81 | 3.63 | 0.95 |
| Ibrutinib | 4 | 4.98 | 1.57 | 0.08 | 0.45 | 0.76 |
| Rapamycin | 4 | 9.96 | 3.07 | 0.31 | 0.85 | 0.38 |
| Vehicle | 5 | 12.45 | 23.07 | 2.87 | 5.04 | 1.07 |
| Ibrutinib | 5 | 14.58 | 3.62 | 0.53 | 3.10 | 0.58 |
| Rapamycin | 5 | 13.91 | 5.14 | 0.71 | 1.07 | 0.21 |
| Vehicle | 7 | 35.15 | 16.25 | 5.71 | 4.57 | 4.75 |
| Ibrutinib | 7 | 75.09 | 11.37 | 8.53 | 3.53 | 0.88 |
| Rapamycin | 7 | 28.03 | 6.49 | 1.82 | 2.16 | 1.13 |

(Continued) Gated on $CFSE^+CD8^+T$ cells

| Treatment | Day | $CD45RA^{High}$ $CD25^{Low}$ (%) | Apoptotic Cell (%) | Dead cells (%) | $CD45RA^{Low}$ $CD25^{High}$ (%) | Apoptotic Cells (%) | Dead cells (%) |
|---|---|---|---|---|---|---|---|
| — | 0 | 28.63 | 0.00 | 0.00 | 0.00 | NA | NA |
| Vehicle | 3 | 13.98 | 5.50 | 0.17 | 35.85 | 5.02 | 0.87 |
| Ibrutinib | 3 | 38.49 | 0.44 | 0.00 | 1.68 | 0.00 | 0.00 |
| Rapamycin | 3 | 16.11 | 0.53 | 0.00 | 27.34 | 0.31 | 0.63 |
| Vehicle | 4 | 14.93 | 4.49 | 1.19 | 25.56 | 3.61 | 0.64 |
| Ibrutinib | 4 | 32.02 | 0.47 | 0.00 | 6.95 | 0.00 | 0.00 |
| Rapamycin | 4 | 16.03 | 0.59 | 0.39 | 30.19 | 0.84 | 0.21 |
| Vehicle | 5 | 13.92 | 5.88 | 0.31 | 26.56 | 6.12 | 1.42 |
| Ibrutinib | 5 | 39.72 | 2.94 | 0.18 | 13.00 | 3.65 | 0.28 |
| Rapamycin | 5 | 8.87 | 2.33 | 0.00 | 43.80 | 0.79 | 0.24 |
| Vehicle | 7 | 13.96 | 8.06 | 1.48 | 6.96 | 4.43 | 5.10 |
| Ibrutinib | 7 | 31.67 | 5.43 | 0.22 | 6.73 | 2.86 | 2.67 |
| Rapamycin | 7 | 9.00 | 3.47 | 0.69 | 21.79 | 1.15 | 0.72 |

(Continued) Gated on $CFSE^+CD8^+T$ cells

| Treatment | Day | $pRPS6^+$ (%) | Apoptotic cells (%) | Dead cells (%) | $pRPS6^+$ (%) | Apoptotic cells (%) | Dead cells (%) |
|---|---|---|---|---|---|---|---|
| — | 0 | 99.59 | 0.00 | 0.00 | 0.41 | 0.00 | 0.00 |
| Vehicle | 3 | 71.61 | 4.39 | 0.67 | 28.39 | 7.28 | 0.59 |
| Ibrutinib | 3 | 96.64 | 0.17 | 0.17 | 3.36 | 0.00 | 0.00 |
| Rapamycin | 3 | 99.49 | 0.43 | 0.26 | 0.51 | 0.00 | 0.00 |
| Vehicle | 4 | 63.24 | 3.08 | 1.06 | 36.76 | 4.57 | 0.76 |
| Ibrutinib | 4 | 86.25 | 0.53 | 0.53 | 13.75 | 0.00 | 2.20 |
| Rapamycin | 4 | 99.15 | 0.86 | 0.38 | 0.85 | 0.00 | 0.00 |
| Vehicle | 5 | 79.00 | 4.36 | 1.26 | 21.00 | 7.62 | 0.35 |
| Ibrutinib | 5 | 66.56 | 1.81 | 0.49 | 33.44 | 5.68 | 0.76 |
| Rapamycin | 5 | 99.28 | 1.04 | 0.21 | 0.72 | 4.76 | 0.00 |
| Vehicle | 7 | 93.93 | 4.42 | 4.99 | 6.07 | 6.91 | 1.07 |

TABLE 8-continued

Adjusted mass cytometry antibody staining panel for experiments on directing fate of human naïve CFSE+ CD8+ T cells using ibrutinib over REP days 0-7.

| Ibrutinib | 7 | 91.71 | 3.30 | 0.90 | 8.29 | 5.96 | 0.62 |
| Rapamycin | 7 | 99.44 | 2.14 | 1.13 | 0.56 | 5.56 | 0.00 | cPARP, cleaved PARP; pRPS6, phosphorylated ribosomal protein S6 (pS235/236).
*These antibodies were used for intracellular staining (post-methanol). Remaining antibodies were used during surface staining (prior to methanol permeabilization).
**Recommended concentrations were adjusted based on in-house titration results.

REFERENCES

1. Chang, J. T. et al. Asymmetric T lymphocyte division in the initiation of adaptive immune responses. *Science* 315, 1687-1691 (2007).
2. Oliaro, J. et al. Asymmetric cell division of T cells upon antigen presentation uses multiple conserved mechanisms. *Journal of immunology* 185, 367-375 (2010).
3. Gerlach, C. et al. One naïve T cell, multiple fates in CD8+ T cell differentiation. *The Journal of experimental medicine* 207, 1235-1246 (2010).
4. Gerlach, C. et al. Heterogeneous differentiation patterns of individual CD8+ T cells. *Science* 340, 635-639 (2013).
5. Tubo, N. J. et al. Most microbe-specific naïve CD4(+) T cells produce memory cells during infection. *Science* 351, 511-514 (2016).
6. Woodworth, M. B., Girskis, K. M. & Walsh, C. A. Building a lineage from single cells: genetic techniques for cell lineage tracking. *Nature reviews. Genetics* 18, 230-244 (2017).
7. Quah, B. J., Lyons, A. B. & Parish, C. R. The use of CFSE-like dyes for measuring lymphocyte proliferation: experimental considerations and biological variables. 790 *Mathematical Modelling of Natural Phenomena* 7, 53-64 (2012).
8. Quah, B. J. & Parish, C. R. New and improved methods for measuring lymphocyte proliferation in vitro and in vivo using CFSE-like fluorescent dyes. *Journal of immunological methods* 379, 1-14 (2012).
9. Heinzel, S. et al. A Myc-dependent division timer complements a cell-death timer to regulate T cell and B cell responses. *Nature immunology* 18, 96-103 (2017).
10. Bandura, D. R. et al. Mass cytometry: technique for real time single cell multitarget immunoassay based on inductively coupled plasma time-of-flight mass spectrometry. *Analytical chemistry* 81, 6813-6822 (2009).
11. Bendall, S. C. et al. Single-cell mass cytometry of differential immune and drug responses across a human hematopoietic continuum. *Science* 332, 687-696 (2011).
12. Lyons, A. B. & Parish, C. R. Determination of lymphocyte division by flow cytometry. *Journal of immunological methods* 171, 131-137 (1994).
13. Rosenberg, S. A. & Restifo, N. P. Adoptive cell transfer as personalized immunotherapy for human cancer. *Science* 348, 62-68 (2015).
14. Gattinoni, L., Speiser, D. E., Lichterfeld, M. & Bonini, C. T memory stem cells in health and disease. *Nature medicine* 23, 18-27 (2017).
15. Li, Y. & Kurlander, R. J. Comparison of anti-CD3 and anti-CD28-coated beads with soluble anti-CD3 for expanding human T cells: differing impact on CD8 T cell phenotype and responsiveness to restimulation. *Journal of translational medicine* 8, 104 (2010).
16. Dubovsky, J. A. et al. Ibrutinib is an irreversible molecular inhibitor of ITK driving a Th1-selective pressure in T lymphocytes. *Blood* 122, 2539-2549 (2013).
17. Apetoh, L. et al. Consensus nomenclature for CD8+ T cell phenotypes in cancer. *Oncoimmunology* 4, e998538 (2015).
18. Quah, B. J. & Parish, C. R. The use of carboxyfluorescein diacetate succinimidyl ester (CFSE) to monitor lymphocyte proliferation. *Journal of visualized experiments: JoVE* (2010).
19. Fleischer, J. et al. Differential expression and function of CD80 (B7-1) and CD86 (B7-2) on human peripheral blood monocytes. *Immunology* 89, 592-598 (1996).
20. Ju, S. W. et al. A functional anti-human 4-1BB ligand monoclonal antibody that enhances proliferation of monocytes by reverse signaling of 4-1BBL. *Hybridoma and hybridomics* 22, 333-338 (2003).
21. Rosenberg, S. A. & Dudley, M. E. Cancer regression in patients with metastatic melanoma after the transfer of autologous antitumor lymphocytes. *Proceedings of the National Academy of Sciences of the United States of America* 101 Suppl 2, 14639-14645 (2004).
22. Chacon, J. A. et al. Co-stimulation through 4-1BB/CD137 improves the expansion and function of CD8(+) melanoma tumor-infiltrating lymphocytes for adoptive T-cell therapy. *PloS one* 8, e60031 (2013).
23. Forget, M. A. et al. Activation and Propagation of Tumor-infiltrating Lymphocytes on Clinical-grade Designer Artificial Antigen-presenting Cells for Adoptive Immunotherapy of Melanoma. *Journal of immunotherapy* 37, 448-460 (2014).
24. Mellman, I., Coukos, G. & Dranoff, G. Cancer immunotherapy comes of age. *Nature* 480, 480-489 (2011).
25. Kono, K. Current status of cancer immunotherapy. *Journal of stem cells & regenerative medicine* 10, 8-13 (2014).
26. Mackall, C. L., Merchant, M. S. & Fry, T. J. Immune-based therapies for childhood cancer. *Nature reviews. Clinical oncology* 11, 693-703 (2014).
27. Brenchley, J. M. et al. Expansion of activated human naïve T-838 cells precedes effector function. *Clin Exp Immunol* 130, 432-440 (2002).
28. Lin, W. W. et al. CD8+ T Lymphocyte Self-Renewal during Effector Cell Determination. *Cell reports* 17, 1773-1782 (2016).
29. Nish, S. A. et al. CD4+ T cell effector commitment coupled to self-renewal by asymmetric cell divisions. *The Journal of experimental medicine* 214, 39-47 (2017).
30. Samusik, N., Good, Z., Spitzer, M. H., Davis, K. L. & Nolan, G. P. Automated mapping of phenotype space with single-cell data. *Nature methods* 13, 493-496 (2016).
31. Jacomy, M., Venturini, T., Heymann, S. & Bastian, M. ForceAtlas2, a continuous graph layout algorithm for handy network visualization designed for the Gephi software. *PloS one* 9, e98679 (2014).
32. Zunder, E. R., Lujan, E., Goltsev, Y., Wernig, M. & Nolan, G. P. A continuous molecular roadmap to iPSC reprogramming through progression analysis of single-cell mass cytometry. *Cell stem cell* 16, 323-337 (2015).

33. Coifman, R. R. et al. Geometric diffusions as a tool for harmonic analysis and structure definition of data: diffusion maps. *Proceedings of the National Academy of Sciences of the United States of America* 102, 7426-7431 (2005).
34. Angerer, P. et al. destiny: diffusion maps for large-scale single-cell data in R. *Bioinformatics* 32, 1241-1243 (2016).
35. Nestorowa, S. et al. A single-cell resolution map of mouse hematopoietic stem and progenitor cell differentiation. *Blood* 128, e20-31 (2016).
36. Tibshirani, R. Regression shrinkage and selection via the lasso. *Journal of the Royal Statistical Society*, Series B, 267-288 (1996).
37. Friedman, J., Hastie, T. & Tibshirani, R. Regularization Paths for Generalized Linear Models via Coordinate Descent. *J Stat Softw* 33, 1-22 (2010).
38. Xu, L., Zhang, Y., Luo, G. & Li, Y. The roles of stem cell memory T cells in hematological malignancies. *J Hematol Oncol* 8, 113 (2015).
39. Sabatino, M. et al. Generation of clinical-grade CD19-specific CAR-modified CD8+ memory stem cells for the treatment of human B-cell malignancies. *Blood* 128, 519-528 (2016).
40. Advani, R. H. et al. Bruton tyrosine kinase inhibitor ibrutinib (PCI-32765) has significant activity in patients with relapsed/refractory B-cell malignancies. *Journal of clinical oncology: official journal of the American Society of Clinical Oncology* 31, 88-94 (2013).
41. Marostica, E. et al. Population pharmacokinetic model of ibrutinib, a Bruton tyrosine kinase inhibitor, in patients with B cell malignancies. *Cancer chemotherapy and pharmacology* 75, 111-121 (2015).
42. Araki, K. et al. mTOR regulates memory CD8 T-cell differentiation. *Nature* 460, 108-112 (2009).
43. Stenton, S. B., Partovi, N. & Ensom, M. H. Sirolimus: the evidence for clinical pharmacokinetic monitoring. *Clinical pharmacokinetics* 44, 769-786 (2005).
44. Begum, J. et al. A method for evaluating the use of fluorescent dyes to track proliferation in cell lines by dye dilution. *Cytometry. Part A: the journal of the International Society for Analytical Cytology* 83, 1085-1095 (2013).
45. Rambold, A. S. & Pearce, E. L. Mitochondrial Dynamics at the Interface of Immune Cell Metabolism and Function. *Trends in immunology* 39, 6-18 (2018).
46. Battich, N., Stoeger, T. & Pelkmans, L. Control of Transcript Variability in Single Mammalian Cells. *Cell* 163, 1596-1610 (2015).
47. Reiner, S. L. & Adams, W. C. Lymphocyte fate specification as a deterministic but highly plastic process. *Nature reviews. Immunology* 14, 699-704 (2014).
48. Marchingo, J. M. et al. T cell signaling. Antigen affinity, costimulation, and cytokine inputs sum linearly to amplify T cell expansion. *Science* 346, 1123-1127 (2014). receptor signaling reveals kinetic and quantitative differences that affect cell function. *Science signaling* 11 (2018).
50. Klein Geltink, R. I. et al. Mitochondrial Priming by CD28. *Cell* 171, 385-397 e311 (2017).
51. Kalia, V. et al. Prolonged interleukin-2Ralpha expression on virus-specific CD8+ T cells favors terminal-effector differentiation in vivo. Immunity 32, 91-103 (2010).
52. Pipkin, M. E. et al. Interleukin-2 and inflammation induce distinct transcriptional programs that promote the differentiation of effector cytolytic T cells. *Immunity* 32, 79-90 (2010).
53. Long, M. et al. Ibrutinib treatment improves T cell number and function in CLL patients. *The Journal of clinical investigation* 127, 3052-3064 (2017).
54. Turtle, C. J. et al. Durable Molecular Remissions in Chronic Lymphocytic Leukemia Treated With CD19-Specific Chimeric Antigen Receptor-Modified T Cells After Failure of Ibrutinib. *Journal of clinical oncology: official journal of the American Society of Clinical Oncology* 35, 3010-3020 (2017).
55. Fraietta, J. A. et al. Ibrutinib enhances chimeric antigen receptor T-cell engraftment and efficacy in leukemia. *Blood* 127, 1117-1127 (2016).
56. Gill, S. et al. CD19 CAR-T cells combined with ibrutinib to induce complete remission in CLL. *Journal of clinical oncology: official journal of the American Society of Clinical Oncology* 35, suppl; abstr 7509 (2017).
57. Huang, F. et al. The tyrosine kinase Itk suppresses CD8+ memory T cell development in response to bacterial infection. *Scientific reports* 5, 7688 (2015).
58. Fienberg, H. G., Simonds, E. F., Fantl, W. J., Nolan, G. P. & Bodenmiller, B. A platinum based covalent viability reagent for single-cell mass cytometry. *Cytometry. Part A: the journal of the International Society for Analytical Cytology* 81, 467-475 (2012).
59. Zunder, E. R. et al. Palladium-based mass tag cell barcoding with a doublet-filtering scheme and single-cell deconvolution algorithm. *Nature protocols* 10, 316-333 (2015).
60. Finck, R. et al. Normalization of mass cytometry data with bead standards. *Cytometry. Part A: the journal of the International Society for Analytical Cytology* 83, 483-494 (2013).
61. Zheng, G. X. et al. Massively parallel digital transcriptional profiling of single cells. *Nature communications* 8, 14049 (2017).
62. Bates, D., Machler, M., Bolker, B. M. & Walker, S. C. Fitting Linear Mixed-Effects Models Using lme4. *Journal of Statistical Software* 67, 1-48 (2015).
63. James, G., Witten, D., Hastie, T. & Tibshirani, R. An Introduction to Statistical Learning with Applications in R, Edn. 6th. (Springer Texts in Statistics, 2015).

What is claimed is:

1. A method of producing a population of lymphocytes enriched in T stem cell memory cells ($T_{SCM}$ cells), the method comprising contacting a sample comprising naturally occurring T cells or engineered T cells with an agent comprising PCI-32765 (ibrutinib),
    wherein the sample is in contact with the agent during Day 0-3 of the culturing in an amount sufficient to produce a population of lymphocytes enriched in $T_{SCM}$ cells.

2. The method of claim 1, wherein the sample is a biological sample isolated from a subject.

3. The method of claim 2, wherein the biological sample comprises one or more of the following: tumor-infiltrating lymphocytes (TILs), peripheral blood mononuclear cells (PBMCs), human naïve T cells, human primary T cells.

4. The method of claim 1, wherein the sample comprises engineered T cells expressing chimeric antigen receptors (CARs) and/or T cell receptors (TCRs).

5. The method of claim 1, wherein the percentage of $T_{SCM}$ cells in the total cells is increased by about 0.5-fold to about 200-fold after said contacting with the agent when compared to the percentage of $T_{SCM}$ cells in the total cells prior to said contacting.

6. The method of claim 1, wherein the percentage of non-$T_{SCM}$ cells in the total cells is decreased by about 0.5-fold to about 200-fold after said contacting with the agent when compared to the percentage of non-$T_{SCM}$ cells in the total cells prior to said contacting.

7. The method of claim 1, wherein the agent decreases the activity of the Bruton's tyrosine kinase (BTK) signaling pathway and/or the activity of the inducible T cell kinase (ITK) signaling pathway.

8. The method of claim 2, wherein the subject has cancer.

9. The method of claim 8, where said cancer is selected from the group consisting of chronic lymphocytic leukemia (CLL), acute lymphoblastic leukemia (ALL), acute myeloid leukemia (AML), chronic myeloid leukemia (CMIL), lymphomas, brain cancers, blood cancers and melanomas.

10. The method of claim 1, wherein the $T_{SCM}$ cells express one or more of the following: CD7, CD11a, CD27, CD45RA, CD58, CD95, CD127 and CCR7; and/or wherein the $T_{SCM}$ cells do not express one or more of the following: CD45RO, CD57, LAG3, CTLA4 and PD1.

11. The method of claim 1, wherein the $T_{SCM}$ cells produce more effector cytokines IFN-γ and TNF-α as compared to control effector cells.

12. The method of claim 1, wherein the sample is contacted with the agent prior to expansion of the T cells.

13. The method of claim 1, wherein the sample is contacted with the agent less than about 24 hours after T cell expansion initiation.

14. The method of claim 1, further comprising culturing the sample and agent in a culture medium for about 1, 2, 3, 4, 5, 6, 7, 8, 9, or 10 days.

15. The method of claim 13, wherein the sample is in contact with the agent only during days 0-2 or days 0-3 of the culturing.

16. The method of claim 13, wherein the agent is present during days 0-2 or days 0-3 of the culturing at a concentration sufficient to produce a population of lymphocytes enriched in $T_{SCM}$ cells, followed by a decrease of the agent concentration in the culture.

17. The method of claim 14, wherein the agent comprises ibrutinib and is present at a concentration of about 1.6 μM during days 0-2, and at a concentration of about 0.32 μM during days 3-10 of the culturing.

18. The method of claim 14, wherein the agent comprises ibrutinib and is present at a concentration of about 1.6 μM during days 0-2, about 0.32 μM during days 3-6, and about 0 μM during days 7-10 of the culturing.

19. The method of claim 1, wherein the $T_{SCM}$ cells produce more of the proliferation-inducing cytokine IL-2 and less effector cytokines IFN-7 and TNF-α as compared to control effector cells.

* * * * *